United States Patent
Fontaine et al.

(10) Patent No.: US 10,526,431 B2
(45) Date of Patent: Jan. 7, 2020

(54) CATALYST SYSTEMS FOR OLEFIN POLYMERIZATION

(71) Applicant: Dow Global Technologies LLC, Midland, MI (US)

(72) Inventors: Philip P. Fontaine, Alvin, TX (US); Jerzy Klosin, Midland, MI (US); Endre Szuromi, Richwood, TX (US); Carl N. Iverson, Houston, TX (US); Zach T. Rickaway, Rosharon, TX (US); Andrew J. Young, Houston, TX (US); Susan G. Brown, Pearland, TX (US); Ruth Figueroa, Midland, MI (US)

(73) Assignee: Dow Global Technologies LLC, Midland, MI (US)

(*) Notice: Subject to any disclaimer, the term of this patent is extended or adjusted under 35 U.S.C. 154(b) by 0 days.

(21) Appl. No.: 15/310,460

(22) PCT Filed: Jun. 29, 2015

(86) PCT No.: PCT/US2015/038269
§ 371 (c)(1),
(2) Date: Nov. 11, 2016

(87) PCT Pub. No.: WO2016/003878
PCT Pub. Date: Jan. 7, 2016

(65) Prior Publication Data
US 2017/0101493 A1    Apr. 13, 2017

Related U.S. Application Data

(60) Provisional application No. 62/018,841, filed on Jun. 30, 2014.

(51) Int. Cl.
| | | |
|---|---|---|
| C08F 210/16 | (2006.01) |
| C07F 7/00 | (2006.01) |
| C07F 7/28 | (2006.01) |
| B01J 31/22 | (2006.01) |
| C08F 4/659 | (2006.01) |

(52) U.S. Cl.
CPC ......... C08F 210/16 (2013.01); B01J 31/2226 (2013.01); C07F 7/00 (2013.01); C07F 7/28 (2013.01); C08F 4/659 (2013.01); *C08F 4/65908* (2013.01); *C08F 4/65912* (2013.01); *Y02P 20/582* (2015.11)

(58) Field of Classification Search
None
See application file for complete search history.

(56) References Cited

U.S. PATENT DOCUMENTS

| 7,951,882 B2 | 5/2011 | Arriola et al. |
| 8,609,794 B2 * | 12/2013 | Klosin ............... C08F 10/00 526/172 |
| 9,200,185 B2 | 12/2015 | Knutson et al. |
| 9,511,567 B2 | 12/2016 | Hu et al. |
| 2004/0127614 A1 | 7/2004 | Jiang et al. |
| 2005/0288412 A1 | 12/2005 | Hohner et al. |
| 2010/0036069 A1* | 2/2010 | Konze ............... C08F 10/00 526/155 |
| 2011/0313106 A1 | 12/2011 | Shan et al. |
| 2013/0030135 A1 | 1/2013 | Hagadorn et al. |
| 2013/0090430 A1 | 4/2013 | Robert et al. |
| 2013/0144018 A1 | 6/2013 | Klosin et al. |
| 2017/0101494 A1 | 4/2017 | Fontaine et al. |
| 2017/0101495 A1 | 4/2017 | Kapur et al. |

FOREIGN PATENT DOCUMENTS

| WO | 2005/108406 A1 | 11/2005 |
| WO | 2007/136493 A2 | 11/2007 |
| WO | 2012004676 A2 | 1/2012 |
| WO | 2012013699 A1 | 2/2012 |
| WO | 2012/027448 A1 | 3/2012 |
| WO | 2012068576 A2 | 5/2012 |
| WO | 2012069428 A1 | 5/2012 |
| WO | 2012071459 A1 | 5/2012 |
| WO | 2014/058639 A1 | 4/2014 |

OTHER PUBLICATIONS

Kiesewetter, Elizabeth T. "Stereospecific Octahedral Group 4 Bis (phenolate) Ether Complexes for Olefin Polymerization" JACS, 132(16) Apr. 28, 2010.

Rondoll, Soren et al: stereoselective and regioselective propylene polymerization with group 4 bisphenolate ether complexes: Journal of Polymer Sceience Part A: Polymer Chemistry, 50(13) p. 2604-11, Jul. 1, 2012.

PCT/ US2015/038269, International Search Report and Written Opinion dated Sep. 14, 2015.

PCT/ US2015/038269, International Preliminary Report on Patentability. dated Jan. 12, 2017.

(Continued)

*Primary Examiner* — Yun Qian

(74) *Attorney, Agent, or Firm* — Dinsmore & Shohl LLP

(57) ABSTRACT

The instant invention provides a procatalyst comprising a metal-ligand complex of Formula (I): (Formula I), wherein M, X, n, each Z, L, $R^{21}$, $R^{22}$ and $R^1$ through $R^{20}$ are each described herein.

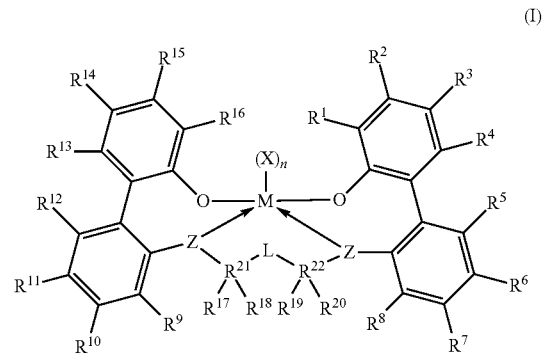

3 Claims, No Drawings

(56) References Cited

OTHER PUBLICATIONS

PCT/ US2015/038269, International Preliminary Report on Patentability. dated Jan. 3, 2017.
PCT/US2015/046008 International Search Report and Written Opinion of the International Searching Authority, dated Nov. 25, 2015.
PCT/US2015/046008, International Preliminary Report on Patentability, dated Mar. 2, 2017.
Office Action dated Nov. 15, 2016 pertaining to U.S. Appl. No. 15/311,299, 5 Pages.
Japanese Office Action dated Mar. 5, 2019 relating to Japanese Patent Application No. 2016-573779.
Chinese Office Action pertaining to Chinese Patent Application No. 201580033387.3, dated Sep. 3, 2019.

* cited by examiner

CATALYST SYSTEMS FOR OLEFIN POLYMERIZATION

REFERENCE TO RELATED APPLICATIONS

The present application claims the benefit of U.S. Provisional Application No. 62/018,841, filed Jun. 30, 2014, and incorporated herein by reference.

BACKGROUND

Olefin-based polymers such as ethylene-based polymers and/or propylene-based polymers are produced via various catalyst systems. Selection of such catalyst systems used in the polymerization process of the olefin based polymers is an important factor contributing to the characteristics and properties of such olefin-based polymers.

Ethylene-based polymers, such as, polyethylene is known for use in the manufacture of a wide a variety of articles. The polyethylene polymerization process can be varied in a number of ways to produce a wide variety of resultant polyethylene resins, having different physical properties that render the various resins suitable for use in different applications. It is generally known that ethylene-based polymers can be produced in solution phase loop reactors, in which ethylene monomer, and optionally one or more alpha olefin comonomers, typically having from 3 to 10 carbon atoms, are circulated in the presence of one or more catalyst systems, under pressure, around a loop reactor, by a circulation pump. The ethylene monomers, and optionally one or more comonomers, are present in a liquid diluent, such as an alkane or isoalkane. Hydrogen may also be added to the reactor. The catalyst systems for producing ethylene-based polymers may typically comprise a chromium-based catalyst system, a Ziegler Natta catalyst system, and/or a molecular (either metallocene or non-metallocene) catalyst system. The reactants in the diluents, and the catalyst system, are circulated, at an elevated polymerization temperature, around the loop reactor, thereby producing polyethylene homopolymer and/or copolymer, depending on whether or not one or more comonomers are present. Either periodically, or continuously, part of the reaction mixture, including the polyethylene product dissolved in the diluent, together with unreacted ethylene and one or more optional comonomers, is removed from the loop reactor. The reaction mixture, when removed from the loop reactor, may be processed to remove the ethylene-based polymer product from the diluent and the unreacted reactants, with the diluent and unreacted reactants typically being recycled back into the loop reactor. Alternatively, the reaction mixture may be sent to a second reactor, e.g., a loop reactor, serially connected to the first loop reactor, where a second polyethylene fraction may be produced.

Despite the research efforts in developing catalyst systems suitable for polyolefin, such as polyethylene and/or polypropylene, polymerization, there is still a need for a procatalyst and a catalyst system, exhibiting high reactivity toward hydrogen, and capacity for producing higher molecular weight polymers; thus, facilitating the production of highly linear polymers under optimum polymerization conditions. Additionally, despite the research efforts in developing polyolefins, such as polyethylene and/or polypropylene, with improved properties, there is still a need for a polyethylene having improved properties. These needs have been met by the following invention.

SUMMARY OF THE INVENTION

The instant invention provides a procatalyst comprising a metal-ligand complex of Formula (I):

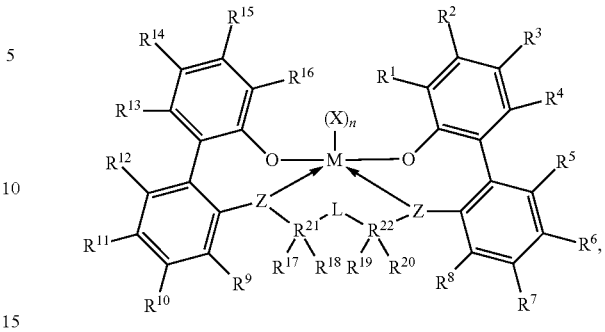

(Formula I)

wherein:

M is titanium, zirconium, or hafnium, each independently being in a formal oxidation state of +2, +3, or +4; and n is an integer of from 0 to 3, and wherein when n is 0, X is absent; and Each X, independently, is a $(C_1$-$C_{40})$ hydrocarbyl, a $(C_1$-$C_{40})$ heterohydrocarbyl, or a halide, and wherein each X, independently, is a monodentate ligand that is neutral, monoanionic, or dianionic; or wherein two Xs are taken together to form a bidentate ligand that is neutral, monoanionic, or dianionic; and wherein X and n are chosen, in such a way, that the metal-ligand complex of Formula (I) is, overall, neutral; and Each Z independently is an oxygen atom, a sulfur atom, —N[$(C_1$-$C_{40})$ hydrocarbyl]-, or —P[$(C_1$-$C_{40})$ hydrocarbyl]-; and L is a substituted or unsubstituted $(C_1$-$C_{40})$hydrocarbylene, or a substituted or unsubstituted $(C_1$-$C_{40})$heterohydrocarbylene, and wherein, for L, the $(C_1$-$C_{40})$ hydrocarbylene has a portion that comprises a 1-carbon atom to 10-carbon atom linker backbone linking $R^{21}$ and $R^{22}$ in Formula (I) (to which L is bonded), or wherein, for L, the $(C_1$-$C_{40})$ heterohydrocarbylene has a portion that comprises a 1-atom to 10-atom linker backbone linking $R^{21}$ and $R^{22}$ in Formula (I), wherein each of the 1 to 10 atoms of the 1-atom to 10-atom linker backbone of the $(C_1$-$C_{40})$ heterohydrocarbylene, independently, is one of the following: i) a carbon atom, ii) a heteroatom, wherein each heteroatom independently is O or S, or iii) a substituent selected from —S(O)—, —S(O)$_2$—, —Si($R^C$)$_2$—, —Ge($R^C$)$_2$—, —P($R^C$)—, or —N($R^C$)—, and wherein each $R^c$ is, independently, a substituted or unsubstituted $(C_1$-$C_{30})$ hydrocarbyl, or a substituted or unsubstituted $(C_1$-$C_{30})$heterohydrocarbyl; and $R^{21}$ and $R^{22}$ are each, independently, C or Si; and $R^1$ through $R^{20}$ are each, independently, selected from the group consisting of following: a substituted or unsubstituted $(C_1$-$C_{40})$ hydrocarbyl, a substituted or unsubstituted $(C_1$-$C_{40})$ heterohydrocarbyl, —Si($R^C$)$_3$, —Ge($R^C$)$_3$, —P($R^C$)$_2$, —N($R^C$)$_2$, —O$R^C$, —S$R^C$, —NO$_2$, —CN, —CF$_3$, —S(O)$R^C$, —S(O)$_2R^C$, —N═C($R^C$)$_2$, —OC(O)$R^C$, —C(O)O$R^C$, —N(R)C(O)$R^C$, —C(O)N($R^C$)$_2$, a halogen atom, and a hydrogen atom; and wherein each $R^c$ is independently a substituted or unsubstituted $(C_1$-$C_{30})$ hydrocarbyl, or a substituted or unsubstituted $(C_1$-$C_{30})$ heterohydrocarbyl; and wherein, when $R^{17}$ is a hydrogen atom, then $R^{18}$ is a substituted or unsubstituted $(C_1$-$C_{40})$ hydrocarbyl, a substituted or unsubstituted $(C_1$-$C_{40})$ heterohydrocarbyl, —Si($R^C$)$_3$, —Ge($R^C$)$_3$, —P($R^C$)$_2$, —N($R^C$)$_2$, —O$R^C$, —S$R^C$, —NO$_2$, —CN, —CF$_3$, —S(O)$R^C$, —S(O)$_2R^C$, —N═C(R$^C$)$_2$, —OC(O)R$^C$, —C(O)OR$^C$, —N(R)C(O)R$^C$, —C(O)N(R$^C$)$_2$, a halogen atom, or a hydrogen atom; and wherein each R$^c$ is independently a substituted or unsubstituted (C$_1$-C$_{30}$) hydrocarbyl, or a substituted or unsubstituted (C$_1$-C$_{30}$) heterohydrocarbyl; or wherein, when R$^{18}$ is a hydrogen atom, then R$^{17}$ is a substituted or unsubstituted (C$_1$-C$_{40}$) hydrocarbyl, a substituted or unsubstituted (C$_1$-C$_{40}$) heterohydrocarbyl, —Si(R$^C$)$_3$, —Ge(R$^C$)$_3$, —P(R$^C$)$_2$, —N(R$^C$)$_2$, —OR$^C$, —SR$^C$, —NO$_2$, —CN, —CF$_3$, —S(O)R$^C$, —S(O)$_2$R$^C$, —N═C(R$^C$)$_2$, —OC(O)R$^C$, —C(O)OR$^C$, —N(R)C(O)R$^C$, —C(O)N(R$^C$)$_2$, a halogen atom, or a hydrogen atom; and wherein each R$^c$ is independently a substituted or unsubstituted (C$_1$-C$_{30}$)hydrocarbyl, or a substituted or unsubstituted (C$_1$-C$_{30}$) heterohydrocarbyl; and/or wherein, when R$^{19}$ is a hydrogen atom, then R$^{20}$ is a substituted or unsubstituted (C$_1$-C$_{40}$) hydrocarbyl, a substituted or unsubstituted (C$_1$-C$_{40}$) heterohydrocarbyl, —Si(R$^C$)$_3$, —Ge(R$^C$)$_3$, —P(R$^C$)$_2$, —N(R$^C$)$_2$, —OR$^S$, —SR$^C$, —NO$_2$, —CN, —CF$_3$, —S(O)R$^B$, —S(O)$_2$R$^C$, —N═C(R$^C$)$_2$, —OC(O)R$^C$, —C(O)OR$^C$, —N(R)C(O)R$^C$, —C(O)N(R$^C$)$_2$, a halogen atom, or a hydrogen atom; and wherein each R$^c$ is independently a substituted or unsubstituted (C$_1$-C$_{30}$) hydrocarbyl, or a substituted or unsubstituted (C$_1$-C$_{30}$) heterohydrocarbyl; or wherein, when R$^{20}$ is a hydrogen atom, then R$^{19}$ is a substituted or unsubstituted (C$_1$-C$_{40}$) hydrocarbyl, a substituted or unsubstituted (C$_1$-C$_{40}$) heterohydrocarbyl, —Si(R$^C$)$_3$, —Ge(R$^C$)$_3$, —P(R$^C$)$_2$, —N(R$^C$)$_2$, —OR$^C$, —SR$^C$, —NO$_2$, —CN, —CF$_3$, —S(O)R$^C$, —S(O)$_2$R$^C$, —N═C(R$^C$)$_2$, —OC(O)R$^C$, —C(O)OR$^C$, —N(R)C(O)R$^C$, —C(O)N(R$^C$)$_2$, a halogen atom, or a hydrogen atom; and wherein each R$^c$ is independently a substituted or unsubstituted (C$_1$-C$_{30}$) hydrocarbyl, or a substituted or unsubstituted (C$_1$-C$_{30}$) heterohydrocarbyl; and wherein, for Formula I, two or more of R$^1$ through R$^{22}$, optionally, may form one or more ring structures, and wherein each ring structures has from 3 to 50 atoms in the ring, excluding any hydrogen atoms; and wherein, for Formula I, one or more hydrogen atoms may optionally be substituted with one or more deuterium atoms.

DETAILED DESCRIPTION OF THE INVENTION

The instant invention provides procatalysts and catalyst systems for olefin polymerization, olefin based polymers polymerized therewith, and process for producing the same.

As discussed above, the invention provides a procatalyst comprising a metal-ligand complex of Formula (I), as described above:

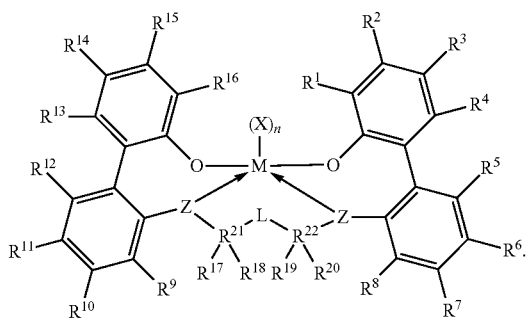

(Formula I)

The procatalyst may comprise a combination of two or more embodiments as described herein.

As used herein, R1═R$^1$, R2═R$^2$, R3═R$^3$, and so forth. As known in the art, O is oxygen, S is sulfur, Si is silicon, and so forth.

In one embodiment, for Formula I, when R$^{17}$ is a hydrogen atom, then R$^{18}$ is a substituted or unsubstituted (C$_1$-C$_{40}$) hydrocarbyl, a substituted or unsubstituted (C$_1$-C$_{40}$) heterohydrocarbyl, —Si(R$^C$)$_3$, —Ge(R$^C$)$_3$, —P(R$^C$)$_2$, —N(R$^C$)$_2$, —OR$^C$, —SR$^C$, —NO$_2$, —CN, —CF$_3$, —S(O)R$^C$, —S(O)$_2$R$^C$, —N═C(R$^C$)$_2$, —OC(O)R$^C$, —C(O)OR$^C$, —N(R)C(O)R$^C$, —C(O)N(R$^C$)$_2$, or a halogen atom; and wherein each R$^c$ is independently a substituted or unsubstituted (C$_1$-C$_{30}$) hydrocarbyl, or a substituted or unsubstituted (C$_1$-C$_{30}$) heterohydrocarbyl; or wherein, when R$^{18}$ is a hydrogen atom, then R$^{17}$ is a substituted or unsubstituted (C$_1$-C$_{40}$) hydrocarbyl, a substituted or unsubstituted (C$_1$-C$_{40}$) heterohydrocarbyl, —Si(R$^C$)$_3$, —Ge(R$^C$)$_3$, —P(R$^C$)$_2$, —N(R$^C$)$_2$, —OR$^C$, —SR$^C$, —NO$_2$, —CN, —CF$_3$, —S(O)R$^C$, —S(O)$_2$R$^C$, —N═C(R$^C$)$_2$, —OC(O)R$^C$, —C(O)OR$^C$, —N(R)C(O)R$^C$, —C(O)N(R$^C$)$_2$, or a halogen atom; and wherein each R$^c$ is independently a substituted or unsubstituted (C$_1$-C$_{30}$) hydrocarbyl, or a substituted or unsubstituted (C$_1$-C$_{30}$) heterohydrocarbyl; and/or wherein, when R$^{19}$ is a hydrogen atom, then R$^{20}$ is a substituted or unsubstituted (C$_1$-C$_{40}$) hydrocarbyl, a substituted or unsubstituted (C$_1$-C$_{40}$) heterohydrocarbyl, —Si(R$^C$)$_3$, —Ge(R$^C$)$_3$, —P(R$^C$)$_2$, —N(R$^C$)$_2$, —OR$^C$, —SR$^C$, —NO$_2$, —CN, —CF$_3$, —S(O)R$^C$, —S(O)$_2$R$^C$, —N═C(R$^C$)$_2$, —OC(O)R$^C$, —C(O)OR$^C$, —N(R)C(O)R$^C$, —C(O)N(R$^C$)$_2$, or a halogen atom; and wherein each R$^c$ is independently a substituted or unsubstituted (C$_1$-C$_{30}$) hydrocarbyl, or a substituted or unsubstituted (C$_1$-C$_{30}$) heterohydrocarbyl; or wherein, when R$^{20}$ is a hydrogen atom, then R$^{19}$ is a substituted or unsubstituted (C$_1$-C$_{40}$) hydrocarbyl, a substituted or unsubstituted (C$_1$-C$_{40}$) hetero-hydrocarbyl, —Si(R$^C$)$_3$, —Ge(R$^C$)$_3$, —P(R$^C$)$_2$, —N(R$^C$)$_2$, —OR$^C$, —SR$^C$, —NO$_2$, —CN, —CF$_3$, —S(O)R$^C$, —S(O)$_2$R$^C$, —N═C(R$^C$)$_2$, —OC(O)R$^C$, —C(O)OR$^C$, —N(R)C(O)R$^C$, —C(O)N(R$^C$)$_2$, or a halogen atom; and wherein each R$^c$ is independently a substituted or unsubstituted (C$_1$-C$_{30}$) hydrocarbyl, or a substituted or unsubstituted (C$_1$-C$_{30}$) heterohydrocarbyl.

In one embodiment, for Formula I, each Z is an oxygen atom.

In one embodiment, for Formula I, R$^{21}$ and R$^{22}$ are each C (carbon).

In one embodiment, each X is, independently, a (C$_1$-C$_{40}$) hydrocarbyl, a (C$_1$-C$_{40}$) hetero-hydrocarbyl, or a halide. In a further embodiment both X groups are the same.

In one embodiment, each X is, independently, a (C$_1$-C$_{40}$) hydrocarbyl, or a halide. In a further embodiment both X groups are the same.

In one embodiment, each X is, independently, a (C$_1$-C$_{40}$) hydrocarbyl. In a further embodiment both X groups are the same.

In one embodiment, each X is, independently, a (C$_1$-C$_3$) alkyl, further ethyl or methyl, and further methyl. In a further embodiment both X groups are the same.

In one embodiment, for Formula I, L is selected from the following: —CH2CH2CH2—, —CH2CH2— or —CH2—; and further —CH2CH2— or —CH2, and further —CH2—.

In one embodiment, for Formula I, each (C$_1$-C$_{40}$) hydrocarbyl, and each (C$_1$-C$_{40}$) hetero-hydrocarbyl is not substituted.

In one embodiment, for Formula I, at least one (C$_1$-C$_{40}$) hydrocarbyl, and/or at least one (C$_1$-C$_{40}$) hetero-hydrocarbyl is/are, independently, substituted with at least on R$^S$ substituent, and wherein each R$^S$ substituent is, independently, selected from the following: a halogen atom, a polyfluoro substituent, a perfluoro substituent, $F_3C-$, $FCH_2O-$, $F_2HCO-$, $F_3CO-$, $(R^C)_3Si-$, $(R^C)_3Ge$, $(R^C)O-$, $(R^C)S-$, $(R_C)S(O)-$, $(R^C)S(O)_2-$, $(R^C)_2P-$, $(R^C)_2N-$, $(R^C)_2C=N-$, $NC-$, $(R^C)C(O)O-$, $(R^C)OC(O)-$, $(R^C)C(O)N(R^C)-$, or $(R^C)_2NC(O)-$; and wherein each $R^c$ is independently a substituted or unsubstituted $(C_1-C_{30})$ hydrocarbyl, or a substituted or unsubstituted $(C_1-C_{30})$ heterohydrocarbyl.

In one embodiment, for Formula I, each $(C_1-C_{40})$ hydrocarbyl, and each $(C_1-C_{40})$ hetero-hydrocarbyl are, independently, substituted with at least on $R^S$ substituent, and wherein each $R^S$ substituent is, independently, selected from the following: a halogen atom, a polyfluoro substituent, a perfluoro substituent, $F_3C-$, $FCH_2O-$, $F_2HCO-$, $F_3CO-$, $(R^C)_3Si-$, $(R^C)_3Ge$, $(R^C)O-$, $(R^C)S-$, $(R^C)S(O)-$, $(R^C)S(O)_2-$, $(R^C)_2P-$, $(R^C)_2N-$, $(R^C)_2C=N-$, $NC-$, $(R^C)C(O)O-$, $(R^C)OC(O)-$, $(R^C)C(O)N(R^C)-$, or $(R^C)_2NC(O)-$; and wherein each $R^c$ is independently a substituted or unsubstituted $(C_1-C_{30})$ hydrocarbyl, or a substituted or unsubstituted $(C_1-C_{30})$ heterohydro-carbyl.

In one embodiment, for Formula 1, two or more of $R^1$ to $R^{22}$ do not form one or more ring structures.

In one embodiment, Formula I does not contain one or more deuterium atoms.

In one embodiment, for Formula I, the procatalyst is selected from the group consisting of the following I1 through I76:

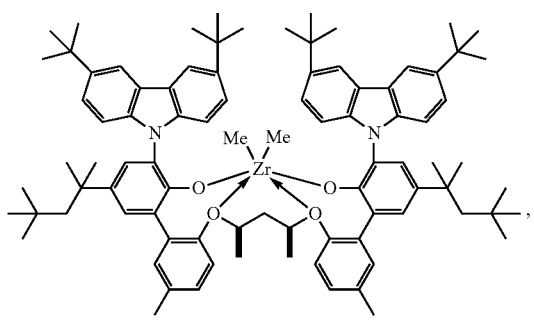

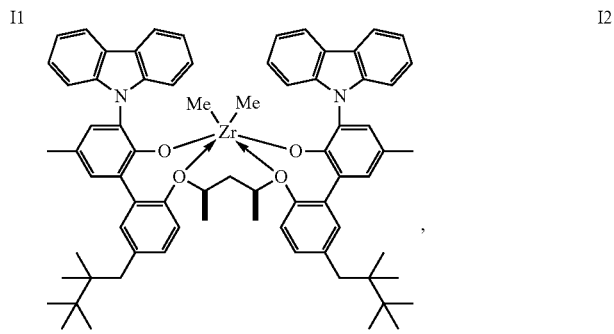

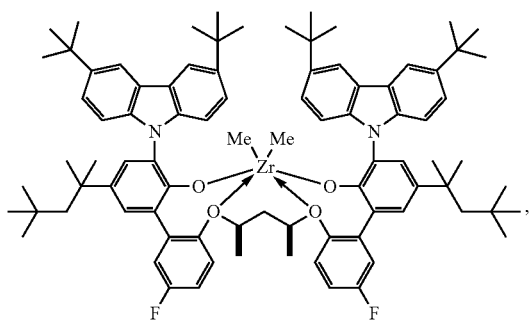

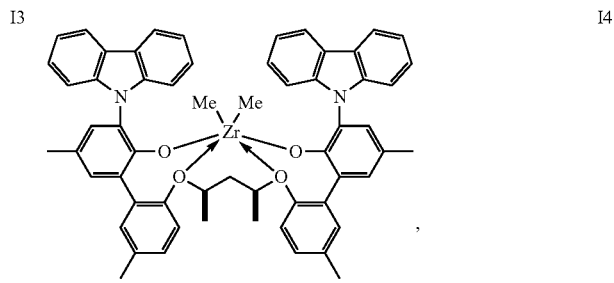

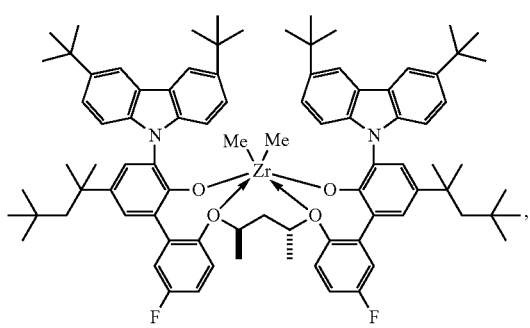

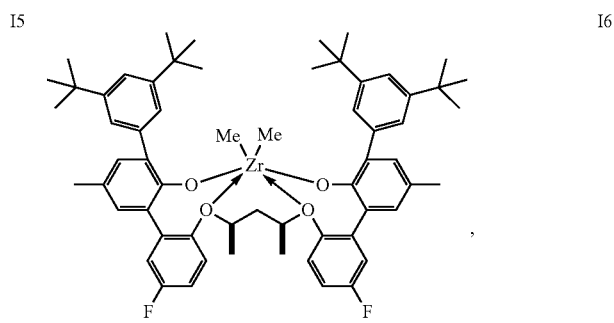

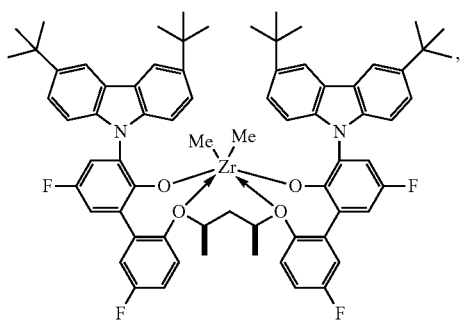

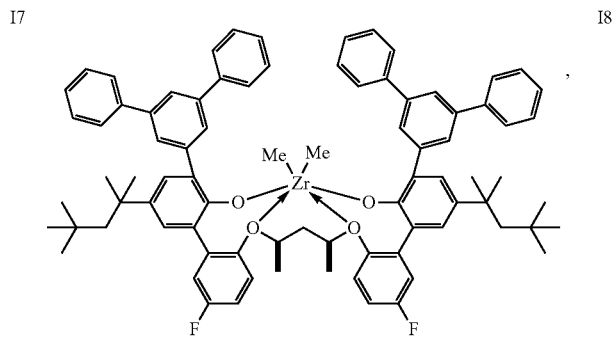

-continued
I9
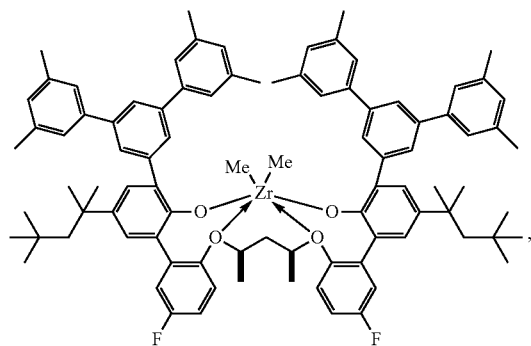
I10
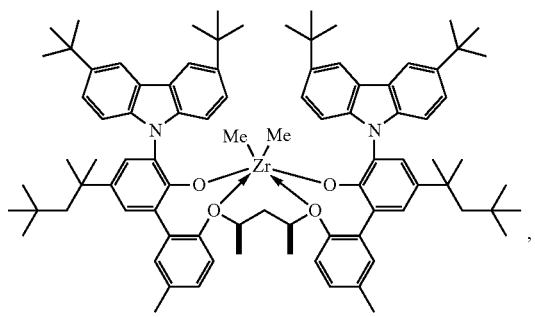
I11
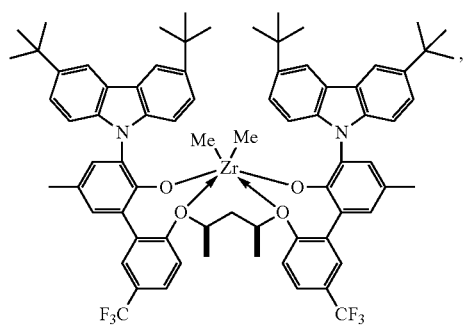
I12
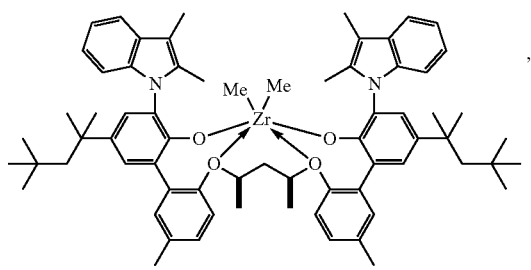
I13
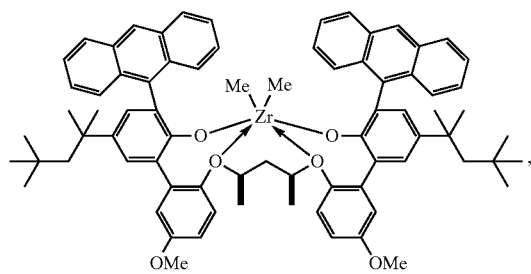
I14
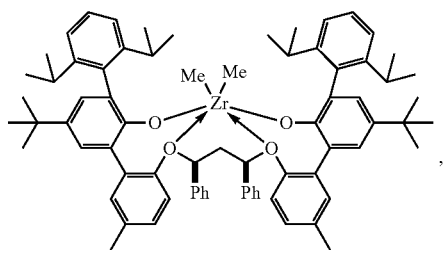
I15
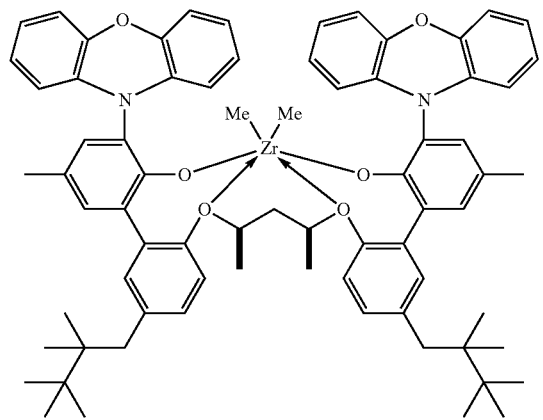
I16
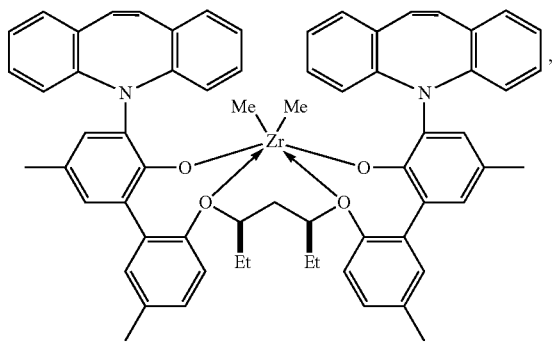

-continued
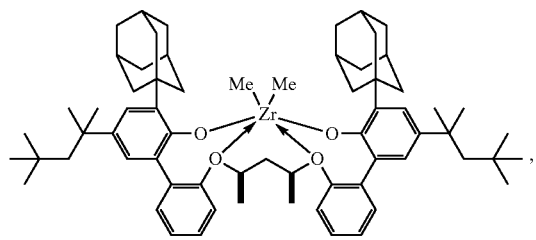
I17
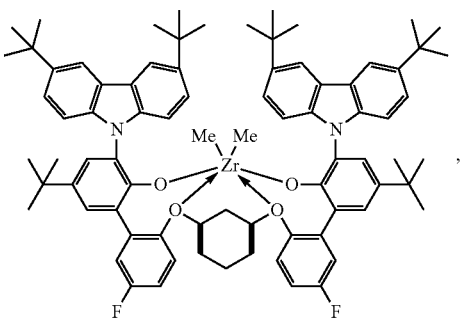
I18
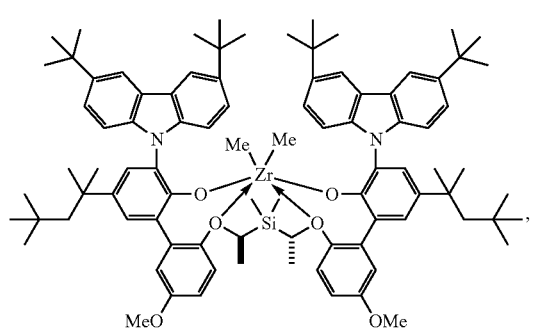
I19
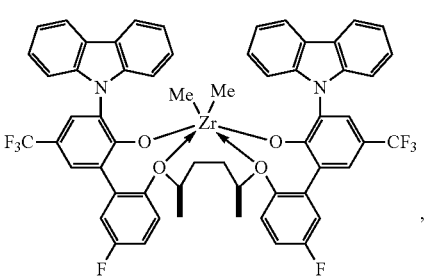
I20
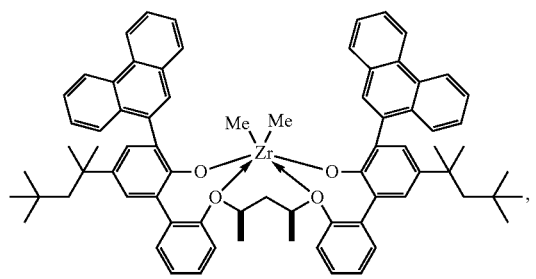
I21
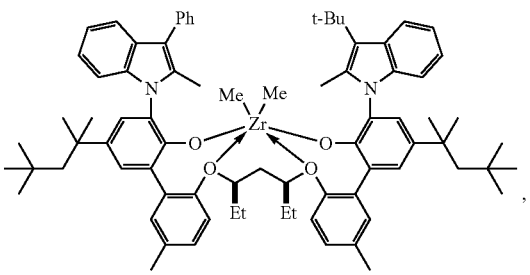
I22
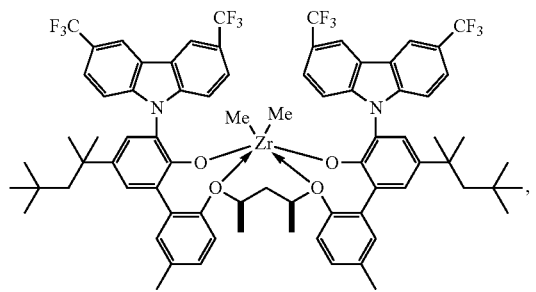
I23
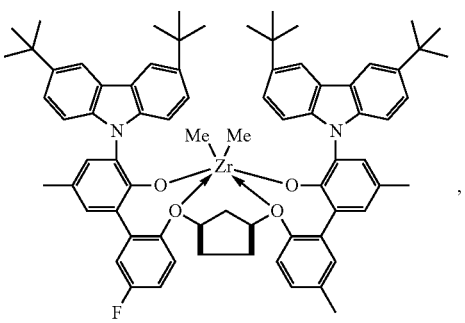
I24
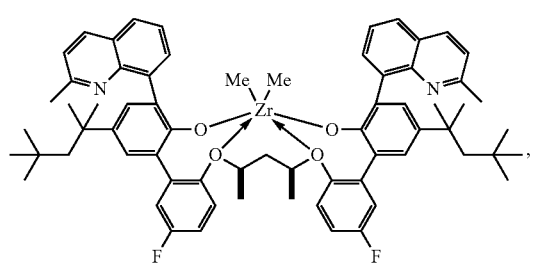
I25
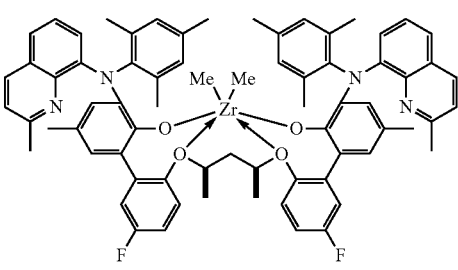
I26

-continued
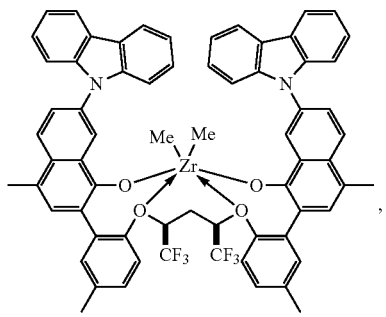
I27
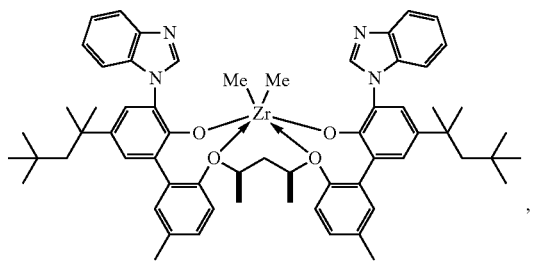
I28
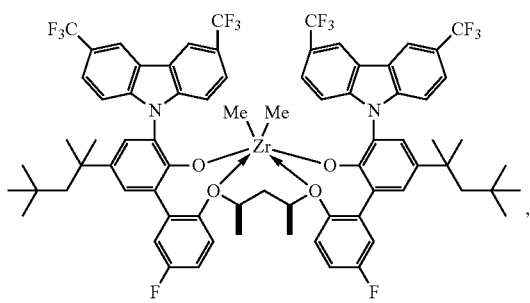
I29
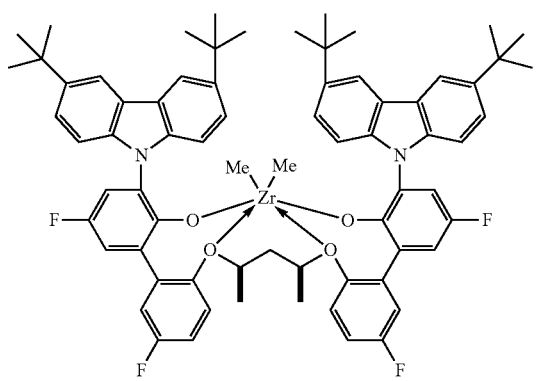
I30
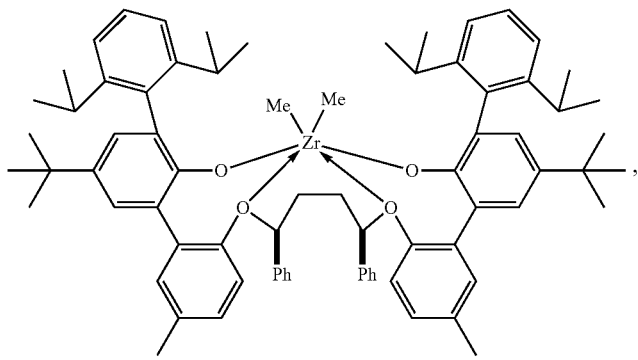
I31
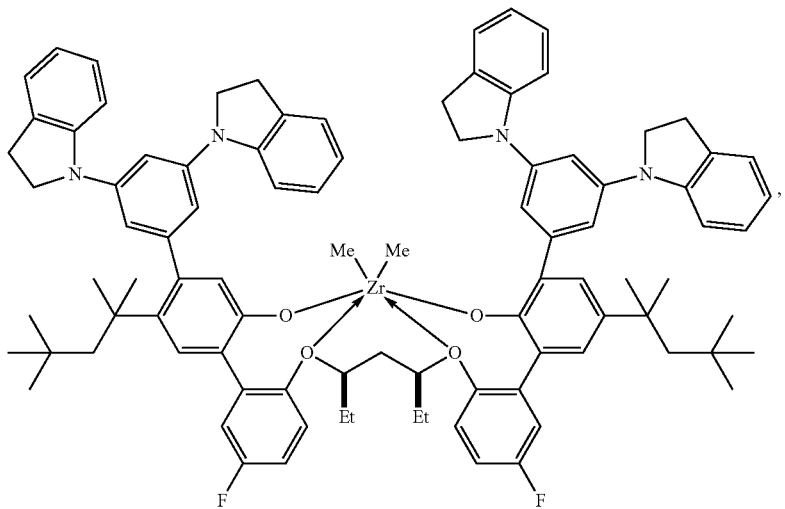
I32

-continued
I33
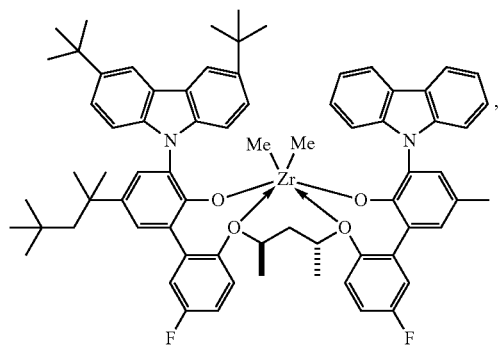
I34
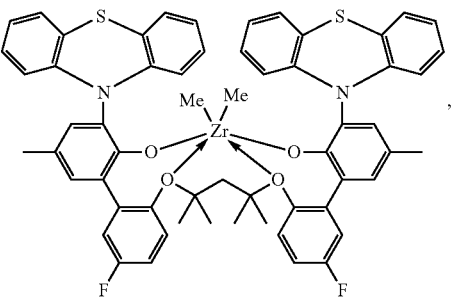
I35
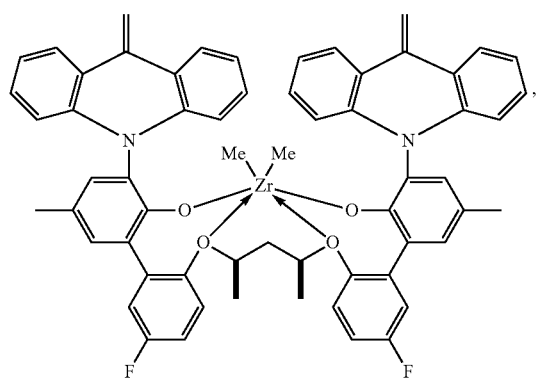
I36
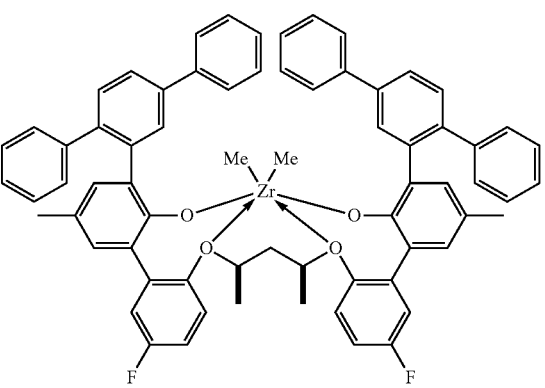
I37
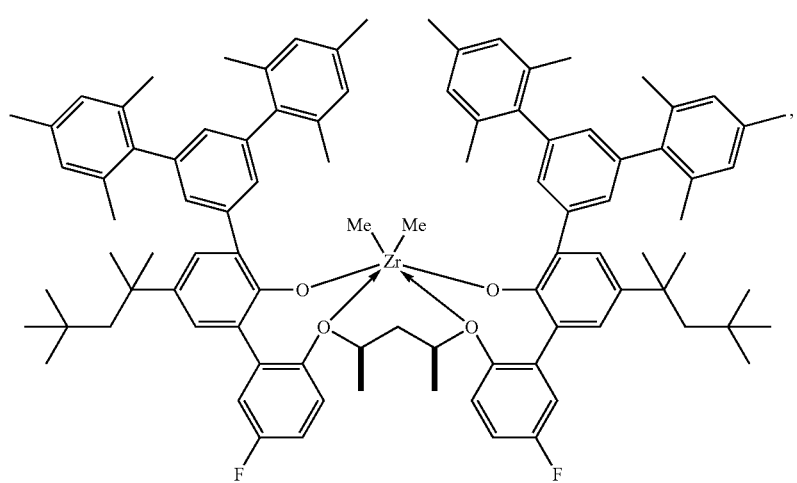
I38
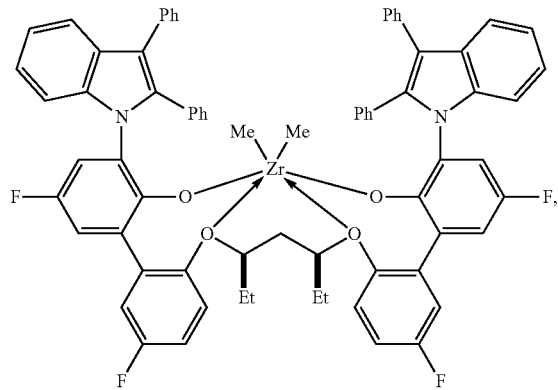
I39
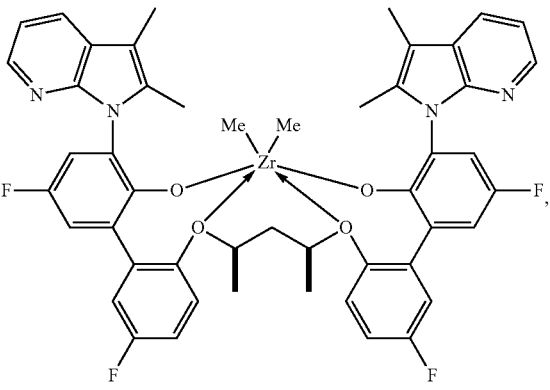

-continued
I40
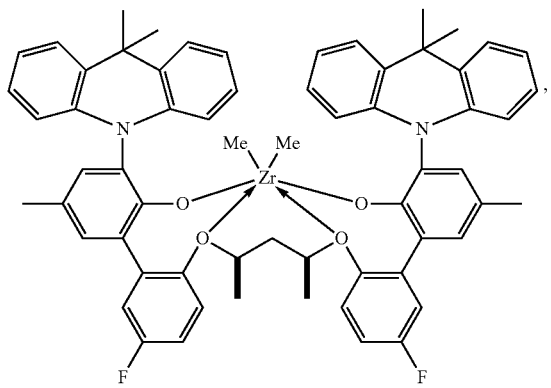
I41
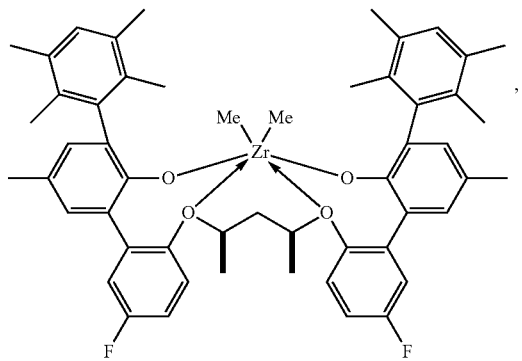
I42
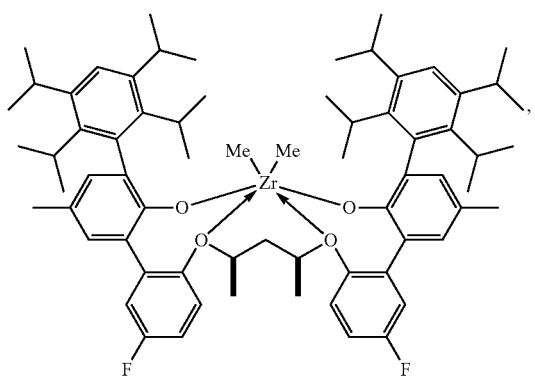
I43
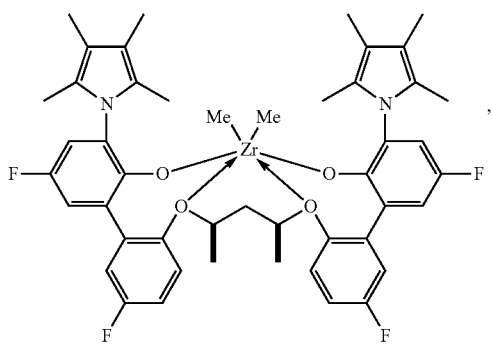
I44
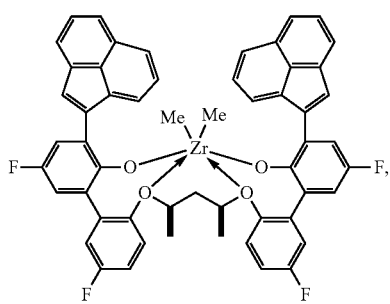
I45
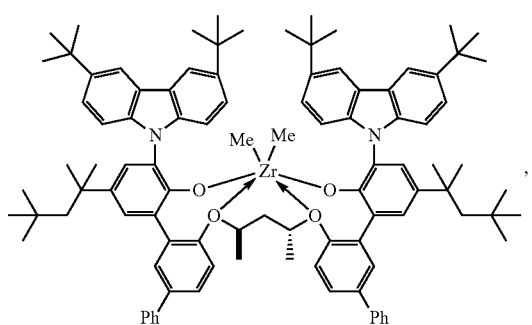
I46
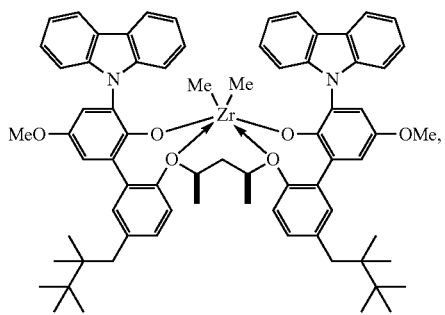
I47
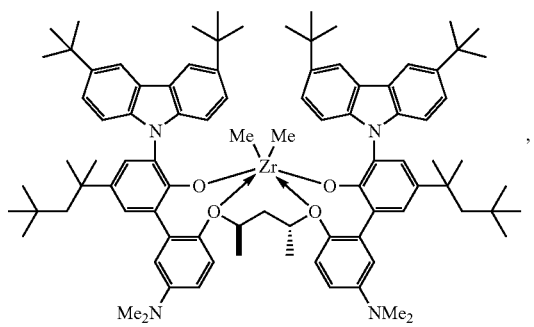

-continued
I48
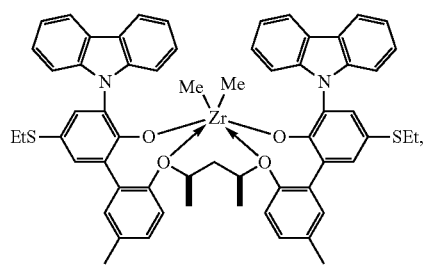
I49
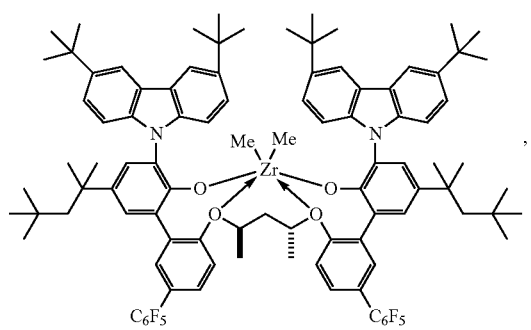
I50
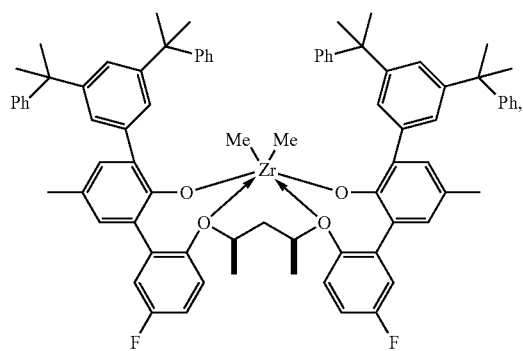
I51
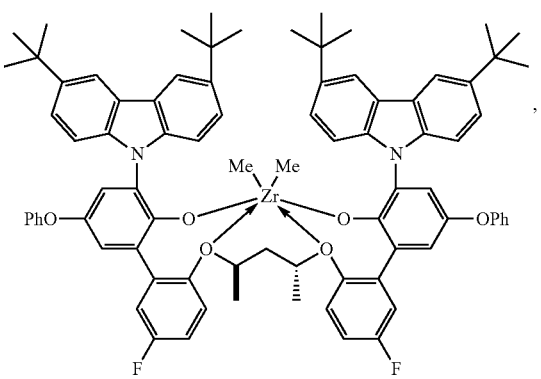
I52
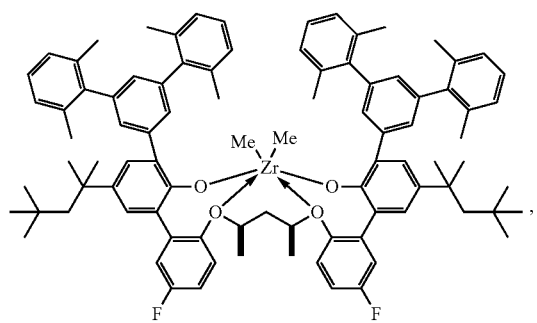
I53
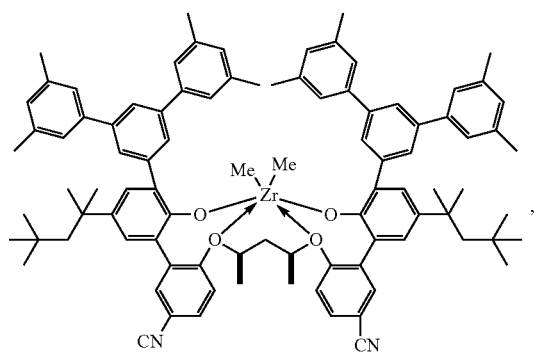
I54
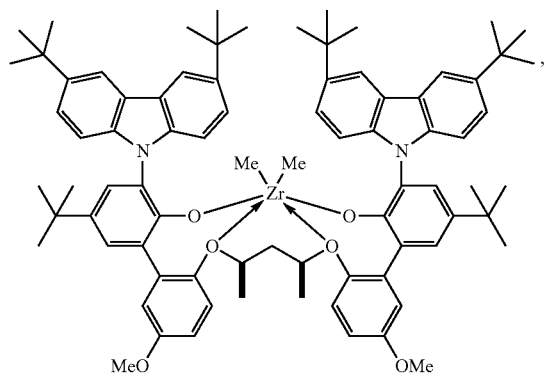
I55
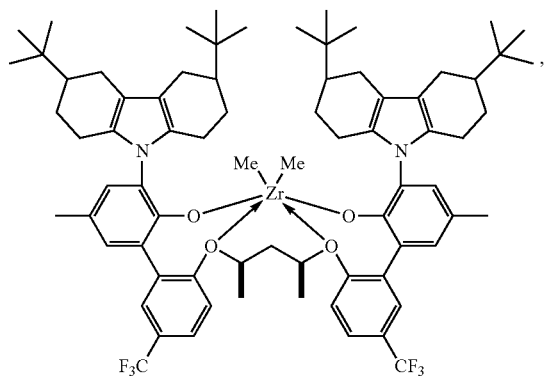

-continued
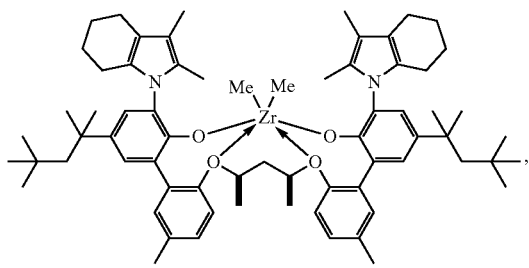
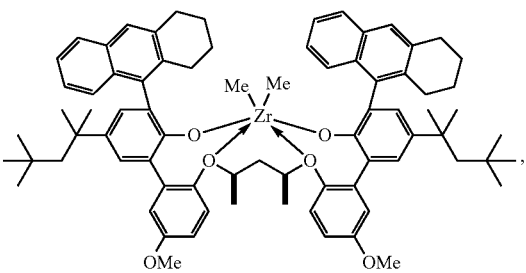
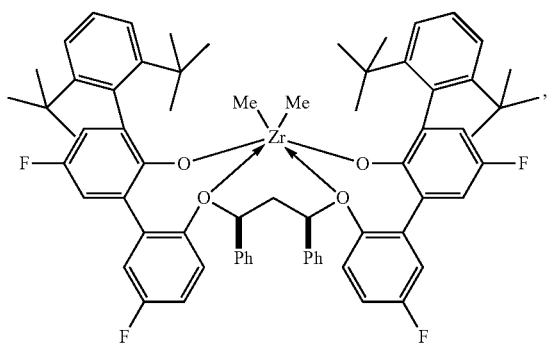
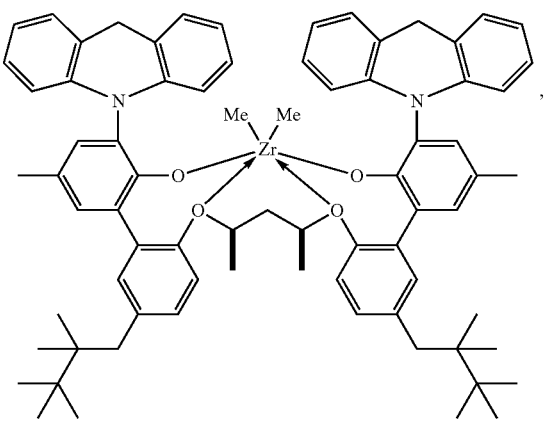
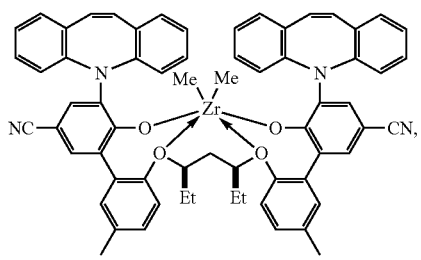
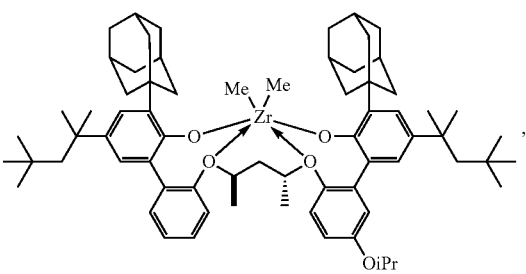
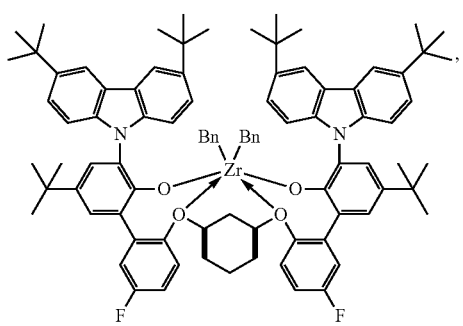
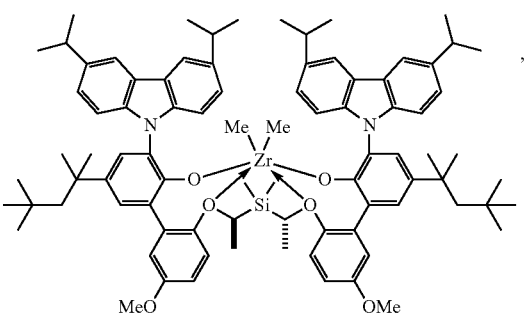
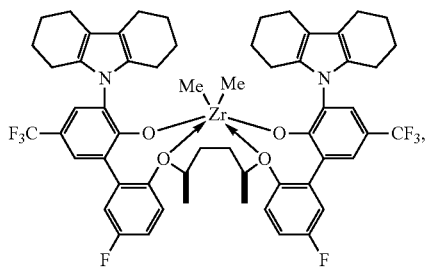
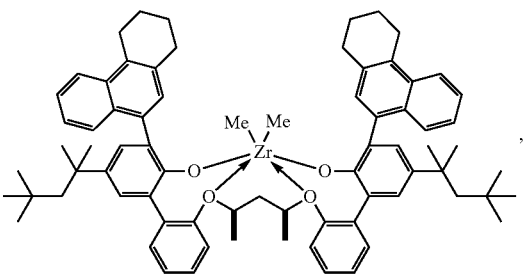

-continued
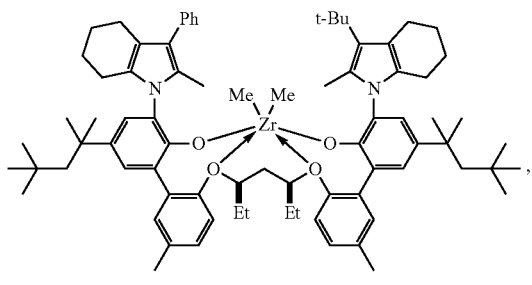
I66
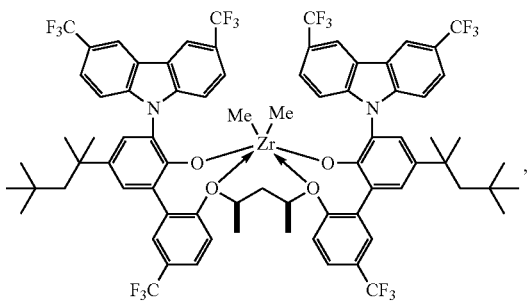
I67
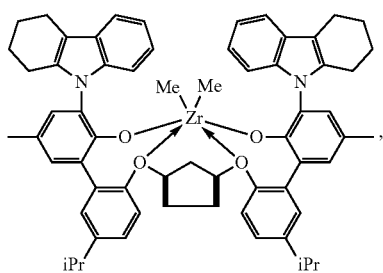
I68
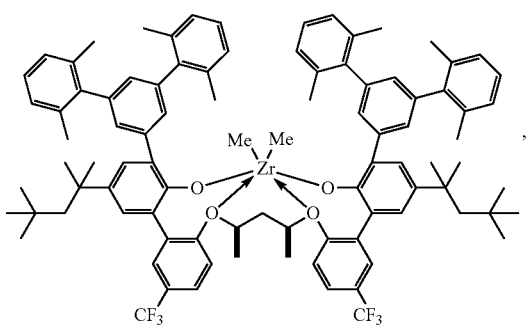
I69
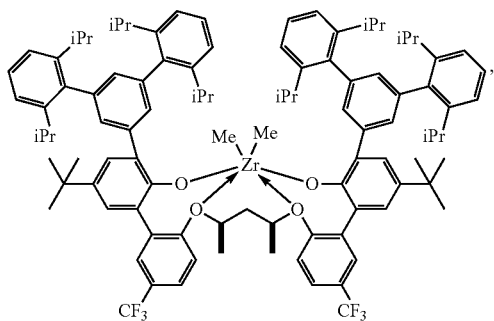
I70
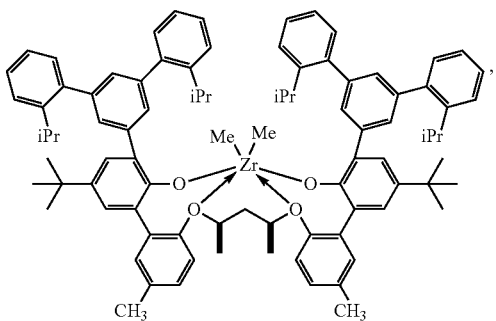
I71
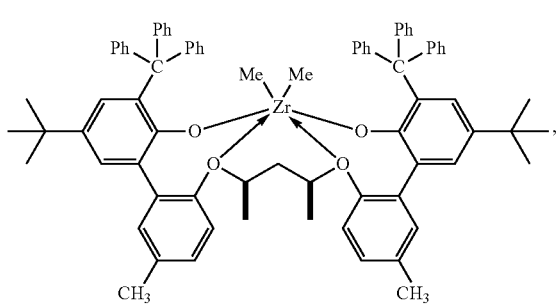
I72
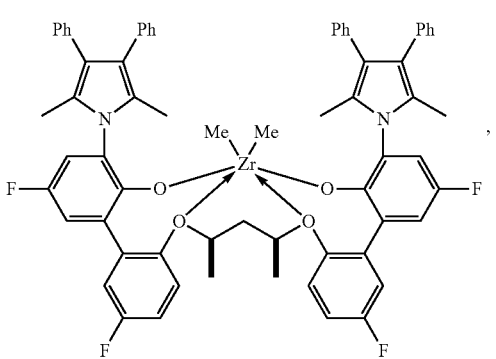
I73

-continued

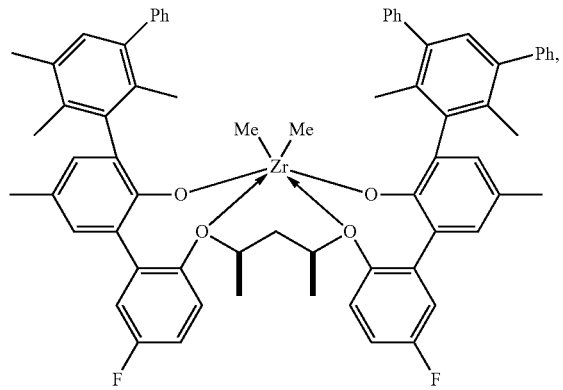

I74

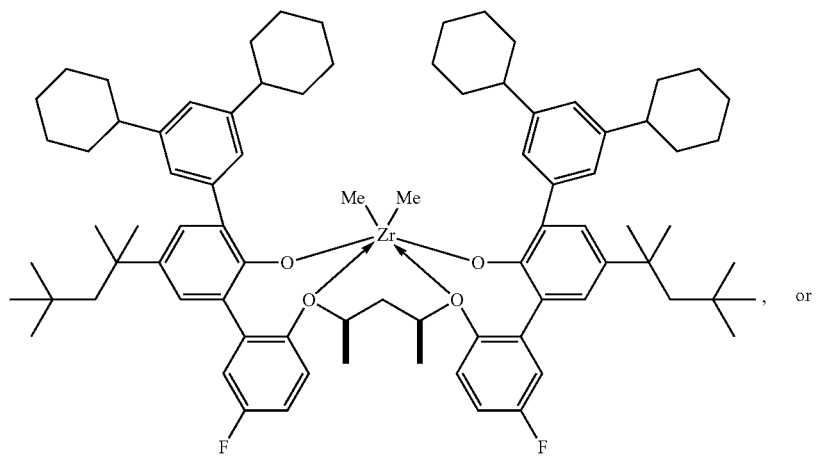

I75

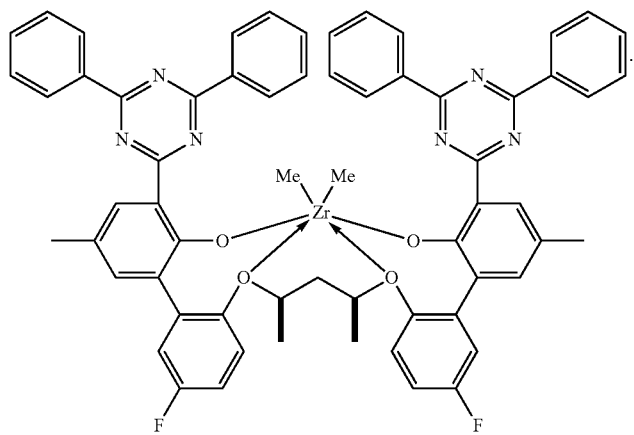

I76

In a further embodiment, for Formula I, the procatalyst is selected from the group consisting of the following: from I1 through I20, further from I1 to I12, further from I1 to I6.

In one embodiment, for Formula I, $R^2$, $R^4$, $R^5$, $R^7$, $R^8$, $R^9$, $R^{10}$, $R^{12}$, $R^{13}$ and $R^{15}$ are each hydrogen.

In one embodiment, for Formula I, M is zirconium or hafnium; n is 2; each X, independently, is a ($C_1$-$C_{40}$) hydrocarbyl, a ($C_1$-$C_{40}$) hetero-hydrocarbyl, or a halide; and $R^2$, $R^4$, $R^5$, $R^7$, $R^8$, $R^9$, $R^{10}$, $R^{12}$, $R^{13}$ and $R^{15}$ are each hydrogen.

In one embodiment, for Formula I, M is zirconium; and each Z is an oxygen atom.

In one embodiment, for Formula I, $R^1$ and $R^{16}$ are each independently selected from the following i) through v):

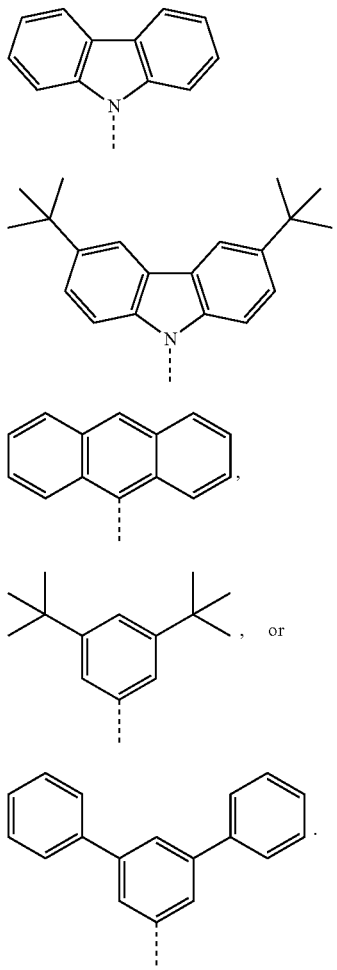

In a further embodiment, both $R^1$ and $R^{16}$ are the same. In each of structures 1) through v), the dashed line (-) indicated the point if attachment to the remainder structure of Formula I.

In one embodiment, for Formula I, $R^1$ and $R^{16}$ are each independently selected from the following i) through ii). In a further embodiment, both $R^1$ and $R^{16}$ are the same.

In one embodiment, for Formula I, $R^{17}$ or $R^{18}$ is a hydrogen atom, and the other is a substituted or unsubstituted ($C_1$-$C_{40}$) hydrocarbyl, a substituted or unsubstituted ($C_1$-$C_{40}$) heterohydrocarbyl, —Si($R^C$)$_3$, —Ge($R^C$)$_3$, —P($R^C$)$_2$, —N($R^C$)$_2$, —O$R^C$, —S$R^C$, —NO$_2$, —CN, —CF$_3$, —S(O)$R^C$, —S(O)$_2R^C$, —N=C($R^C$)$_2$, —OC(O)$R^C$, —C(O)O$R^C$, —N(R)C(O)$R^C$, —C(O)N($R^C$)$_2$, or a halogen atom; and wherein each $R^c$ is independently a substituted or unsubstituted ($C_1$-$C_{30}$) hydrocarbyl, or a substituted or unsubstituted ($C_1$-$C_{30}$) heterohydrocarbyl. In a further embodiment, $R^{19}$ or $R^{20}$ is a hydrogen atom, and the other is a substituted or unsubstituted ($C_1$-$C_{40}$) hydrocarbyl, a substituted or unsubstituted ($C_1$-$C_{40}$) heterohydrocarbyl, —Si($R^C$)$_3$, —Ge($R^C$)$_3$, —P($R^C$)$_2$, —N($R^C$)$_2$, —O$R^C$, —S$R^C$, —NO$_2$, —CN, —CF$_3$, —S(O)$R^C$, —S(O)$_2R^C$, —N=C($R^C$)$_2$, —OC(O)$R^C$, —C(O)O$R^C$, —N(R)C(O)$R^C$, —C(O)N($R^C$)$_2$, or a halogen atom; and wherein each $R^c$ is independently a substituted or unsubstituted ($C_1$-$C_{30}$) hydrocarbyl, or a substituted or unsubstituted ($C_1$-$C_{30}$) heterohydrocarbyl.

In one embodiment, $R^{17}$ or $R^{18}$ is hydrogen, and the other is an unsubstituted hydrocarbyl. In a further embodiment, $R^{19}$ or $R^{20}$ is hydrogen, and the other is an unsubstituted hydrocarbyl.

In one embodiment, for Formula I, $R^{17}$, $R^{18}$, $R^{19}$ and $R^{20}$ are each, independently, an unsubstituted ($C_1$-$C_{40}$) hydrocarbyl. In a further embodiment, $R^{17}$, $R^{18}$, $R^{19}$ and $R^{20}$ are each, independently, an unsubstituted ($C_1$-$C_{30}$) hydrocarbyl, further an unsubstituted ($C_1$-$C_{20}$) hydrocarbyl, further an unsubstituted ($C_1$-$C_{10}$) hydrocarbyl, further an unsubstituted ($C_1$-$C_5$) hydrocarbyl, and further an unsubstituted ($C_1$-$C_3$) hydrocarbyl.

In one embodiment, for Formula I, $R^3$ and $R^{14}$ are each, independently, an unsubstituted ($C_1$-$C_{40}$) hydrocarbyl. In a further embodiment, $R^3$ and $R^{14}$ are each, independently, an unsubstituted ($C_1$-$C_{30}$) hydrocarbyl, further an unsubstituted ($C_1$-$C_{20}$) hydrocarbyl, further an unsubstituted ($C_1$-$C_{10}$) hydrocarbyl, further an unsubstituted ($C_1$-$C_5$) hydrocarbyl, and further an unsubstituted ($C_1$-$C_3$) hydrocarbyl.

In one embodiment, for Formula I, $R^6$ and $R^{11}$ are each, independently, an unsubstituted ($C_1$-$C_{40}$) hydrocarbyl or a halogen. In a further embodiment, $R^6$ and $R^{11}$ are each, independently, an unsubstituted ($C_1$-$C_{30}$) hydrocarbyl, further an unsubstituted ($C_1$-$C_{20}$) hydrocarbyl, further an unsubstituted ($C_1$-$C_{10}$) hydrocarbyl, further an unsubstituted ($C_1$-$C_5$) hydrocarbyl, and further an unsubstituted ($C_1$-$C_3$) hydrocarbyl. In another embodiment, for Formula I, $R^6$ and $R^{11}$ are each, independently a halogen, and further Cl or F, and further F.

The invention also provides a catalyst system comprising the reaction product of the following:

A) one or more procatalysts of any embodiment described herein, or a combination of two or more embodiments described herein; and B) one or more cocatalysts. In a further embodiment, the ratio of the "total number of moles of the one or more metal-ligand complexes of Formula (I)" to the "total number of moles of the one or more cocatalysts" is from 1:10,000 to 100:1.

The invention also provides a polymerization process comprising polymerizing ethylene, optionally with one or more α-olefins, in the presence an inventive catalyst system, to form an ethylene-based polymer.

The invention also provides a polymerization process comprising polymerizing propylene, optionally with ethylene or one or more C4 and higher α-olefins, in the presence an inventive catalyst system, to form a propylene-based polymer.

The invention also provides an ethylene-based polymer formed from an inventive polymerization process of one or more embodiments described herein.

The invention also provides an propylene-based polymer formed from an inventive polymerization process of one or more embodiments described herein.

In another embodiment, the instant invention provides a catalyst system comprising procatalyst comprising a metal-ligand complex of formula (I), as described above and one or more co-catalysts.

In another embodiment, the present invention provides an olefin based polymer comprising the polymerization reaction of one or more a-olefins in the presence of at least one or more inventive catalyst systems, and optionally one or more other catalyst systems in one or more polymerization reactors, connected in parallel, series or combinations thereof.

In another embodiment, the present invention provides a method for producing an olefin based polymer comprising the steps of: (1) providing at least one or more inventive catalyst systems, and optionally one or more other catalyst systems; (2) polymerizing one or more α-olefins in the presence of at least one or more inventive catalyst systems, and optionally one or more other catalyst systems in one or more polymerization reactors, connected in parallel, series or combinations thereof; and (3) thereby producing an olefin based polymer.

In another embodiment, the present invention provides an article comprising the above-described inventive olefin based polymer.

In an alternative embodiment, the instant invention provides a procatalyst, a catalyst composition, polymerization process, an olefin-based polymer, articles made therefrom, in accordance with any of the preceding embodiments, except that Z is O.

As mentioned above, the present invention employs one or more metal-ligand complexes of Formula (I), which is described herein using conventional chemical group terminology. When used to describe certain carbon atom-containing chemical groups (e.g., $(C_1-C_{40})$alkyl), the parenthetical expression $(C_1-C_{40})$ can be represented by the form "$(C_x-C_y)$," which means that the unsubstituted version of the chemical group comprises from a number x carbon atoms to a number y carbon atoms, wherein each x and y independently is an integer as described for the chemical group.

The term "substituted," as used herein, with respect to a chemical compound, refers to a substituent that comprises at least one heteroatom (for example, O, S, N, P, etc.). Substituents include, but are not limited to, the $R^S$ substituents, as noted above, as the following: a halogen atom, a polyfluoro substituent, a perfluoro substituent, $F_3C-$, $FCH_2O-$, $F_2HCO-$, $F_3CO-$, $(R^C)_3Si-$, $(R^C)_3Ge-$, $(R^C)O-$, $(R^C)S-$, $(R^C)S(O)-$, $(R^C)S(O)_2-$, $(R^C)_2P-$, $(R^C)_2N-$, $(R^C)_2C=N-$, $NC-$, $(R^C)C(O)O-$, $(R^C)OC(O)-$, $(R^C)C(O)N(R^C)-$, and $(R^C)_2NC(O)-$; wherein $R^c$ is described above.

The term "unsubstituted," as used herein, with respect to a chemical compound, refers to the lack of a substituent that comprises at least one heteroatom (for example, O, S, N, P, etc.).

The term "hydrocarbyl," as used herein, refers to a monovalent (monoradical or radical) chemical group containing only hydrogen and carbon atoms.

The term "substituted hydrocarbyl," as used herein, refers to a hydrocarbyl, in which at least one hydrogen atom is substituted with a substituent that comprises at least one heteroatom.

The term "heterohydrocarbyl," as used herein, refers to a hydocarbyl, in which at least one carbon atom, or CH group, or CH2 group, is substituted with a heteroatom or a chemical group containing at least one heteroatom. Heteroatoms include, but are not limited to, O, N, P and S.

The term "substituted heterohydrocarbyl," as used herein, refers to a heterohydrocarbyl in which at least one hydrogen atom is substituted with a substituent that comprises at least one heteroatom.

The term "hydrocarbylene," as used herein, refers to a divalent (diradical) chemical group containing only hydrogen and carbon atoms.

The term "substituted hydrocarbylene," as used herein, refers to a hydrocarbylene, in which at least one hydrogen atom is substituted with a substituent that comprises at least one heteroatom.

The term "heterohydrocarbylene," as used herein, refers to a hydrocarbylene, in which at least one carbon atom, or CH group, or CH2 group, is substituted with a heteroatom or a chemical group containing at least one heteroatom. Heteroatoms include, but are not limited to, O, N, P and S.

The term "substituted heterohydrocarbylene," as used herein, refers to a heterohydro-carbylene, in which at least one hydrogen atom is substituted with a substituent that comprises at least one heteroatom.

In some embodiments, each of the chemical groups (e.g., X, L, $R^1$ through $R^{22}$, etc.) of the metal-ligand complex of Formula (I) may be unsubstituted (for example, without use of a substituent $R^S$). In other embodiments, at least one of the chemical groups of the metal-ligand complex of Formula (I) independently contain one or more of the substituents (for example, $R^S$). Preferably, accounting for all chemical groups, there are not more than a total of 20 $R^S$, more preferably not more than a total of 10 $R^S$, and still more preferably not more than a total of 5 $R^S$ in the metal-ligand complex of Formula (I). Where the invention compound contains two or more substituents $R^S$, each $R^S$ independently is bonded to a same or different atom.

As used herein, the term "$(C_1-C_{40})$ hydrocarbyl" refers to hydrocarbon radical of from 1 to 40 carbon atoms. Each hydrocarbon radical independently may be aromatic (6 carbon atoms or more) or non-aromatic, saturated or unsaturated, straight chain or branched chain, cyclic (including mono- and poly-cyclic, fused and non-fused polycyclic, including bicyclic or acyclic, or a combination of two or more thereof; and each hydrocarbon radical independently is the same as, or different from, another hydrocarbon radical, respectively. Each hydrocarbon radical may be optionally substituted with one or more $R^S$ substituents, as defined above. A "$(C_1-C_{30})$ hydrocarbyl" is similarly defined, as discussed above for the "$(C_1-C_{40})$ hydrocarbyl."

Preferably, a $(C_1-C_{40})$ hydrocarbyl is independently a $(C_1-C_{40})$alkyl, or a $(C_3-C_{40})$cycloalkyl. More preferably, each of the aforementioned $(C_1-C_{40})$ hydrocarbyl groups independently has a maximum of 20 carbon atoms (i.e., $(C_1-C_{20})$ hydrocarbyl), and still more preferably a maximum of 12 carbon atoms. Further, the $(C_1-C_{40})$ hydrocarbyl is optionally substituted with one or more $R^S$ substituents, as defined above.

As used herein, the term "$(C_1-C_{40})$ hydrocarbylene" refers to a hydrocarbon diradical of from 1 to 40 carbon atoms. Each hydrocarbon diradical independently may be aromatic (6 carbon atoms or more) or non-aromatic, saturated or unsaturated, straight chain or branched chain, cyclic (including mono- and poly-cyclic, fused and non-fused polycyclic, including bicyclic or acyclic, or a combination of two or more thereof; and each hydrocarbon diradical independently is the same as, or different from, another hydrocarbon diradical, respectively. Further the hydrocarbon radical may be optionally substituted with one or more $R^S$ substituents, as defined above.

Preferably, a $(C_1-C_{40})$ hydrocarbylene independently is a $(C_3-C_{20})$cycloalkyl-$(C_1-C_{20})$alkylene, $(C_6-C_{40})$aryl, or $(C_6-C_{20})$aryl-$(C_1-C_{20})$alkylene. More preferably, each of the aforementioned $(C_1-C_{40})$ hydrocarbylene groups independently has a maximum of 20 carbon atoms (i.e., $(C_1-C_{20})$ hydrocarbyl), and still more preferably a maximum of 12 carbon atoms. The $(C_1-C_{40})$ hydrocarbylene may be optionally substituted with one or more $R^S$ substituents, as defined above.

The term "$(C_1-C_{40})$ heterohydrocarbyl" refers to a heterohydrocarbon radical of from 1 to 40 carbon atoms. Each heterohydrocarbon independently may comprise one or more heteroatoms O; S; S(O); S(O)$_2$; Si($R^C$)$_2$; Ge($R^C$)$_2$; P($R^P$); and N($R^N$), wherein independently each $R^c$ is unsubstituted $(C_1-C_{18})$ hydrocarbyl, each $R^P$ is unsubstituted $(C_1-C_{18})$ hydrocarbyl; and each $R^N$ is unsubstituted $(C_1-C_{18})$ hydrocarbyl. Each $(C_1-C_{40})$ heterohydrocarbyl independently may be saturated or unsaturated, straight chain or branched chain, cyclic (including mono- and poly-cyclic, fused and non-fused polycyclic) or acyclic, or a combination of two or more thereof; and each is respectively the same as or different from another. A "$(C_1-C_{30})$ heterohydrocarbyl" is similarly defined, as discussed above for the "$(C_1-C_{40})$ heterohydrocarbyl."

The term "$(C_1-C_{40})$ heterohydrocarbylene refers to a heterohydrocarbon diradical of from 1 to 40 carbon atoms. Each heterohydrocarbon independently may comprise one or more heteroatoms O; S; S(O); S(O)$_2$; Si($R^C$)$_2$; Ge($R^C$)$_2$; P($R^P$); and N($R^N$), wherein independently each $R^C$ is unsubstituted $(C_1-C_{18})$ hydrocarbyl, each $R^P$ is unsubstituted $(C_1-C_{18})$ hydrocarbyl; and each $R^N$ is unsubstituted $(C_1-C_{18})$ hydrocarbyl. Each $(C_1-C_{40})$ heterohydrocarbylene independently is unsubstituted or substituted (for example, by one or more $R^S$), aromatic or non-aromatic, saturated or unsaturated, straight chain or branched chain, cyclic (including mono- and poly-cyclic, fused and non-fused polycyclic) or acyclic, or a combination of two or more thereof; and each is respectively the same as or different from another.

Preferably, the $(C_1-C_{40})$heterohydrocarbyl independently is $(C_1-C_{40})$heteroalkyl, $(C_1-C_{40})$hydrocarbyl-O—, $(C_1-C_{40})$hydrocarbyl-S—, $(C_1-C_{40})$hydrocarbyl—S(O)—, $(C_1-C_{40})$hydro-carbyl-S (O)$_2$—, $(C_1-C_{40})$ hydrocarbyl-Si($R^C$)$_2$—, $(C_1-C_{40})$hydrocarbyl-Ge($R^C$)$_2$—, $(C_1-C_{40})$hydro-carbyl-N $(R^N)$—, $(C_1-C_{40})$ hydrocarbyl-P($R^P$)—, $(C_2-C_{40})$ heterocycloalkyl.

Preferably, the $(C_1-C_{40})$ heterohydrocarbylene independently is $(C_2-C_{19})$ heterocycloalkyl -$(C_1-C_{20})$alkylene, $(C_3-C_{20})$cycloalkyl-$(C_1-C_{19})$ heteroalkylene, $(C_2-C_{19})$ heterocycloalkyl-$(C_1-C_{20})$ heteroalkylene, $(C_1-C_{40})$ heteroaryl, $(C_1-C_{19})$ heteroaryl-$(C_1-C_{20})$alkylene, $(C_6-C_{20})$aryl-$(C_1-C_{19})$ heteroalkylene, or $(C_1-C_{19})$ heteroaryl-$(C_1-C_{20})$ heteroalkylene.

The term "halogen atom" means fluorine atom (F), chlorine atom (Cl), bromine atom (Br), or iodine atom (I) radical. Preferably each halogen atom independently is the Br, F, or Cl radical, and more preferably the F or Cl radical. The term "halide" means fluoride (F$^-$), chloride (Cl$^-$), bromide (Br$^-$), or iodide (I$^-$) anion.

Preferably, there are no O—O, S—S, or O—S bonds, other than O—S bonds in an S(O) or S(O)$_2$ diradical functional group, in the metal-ligand complex of Formula (I). More preferably, there are no O—O, N—N, P—P, N—P, S—S, or O—S bonds, other than O—S bonds in an S(O) or S(O)$_2$ diradical functional group, in the metal-ligand complex of Formula (I).

The term "saturated" means lacking carbon-carbon double bonds, carbon-carbon triple bonds, and (in heteroatom-containing groups) carbon-nitrogen, carbon-phosphorous, and carbon-silicon double bonds.

The term "unsaturated" means containing one or more carbon-carbon double bonds, carbon-carbon triple bonds, and (in heteroatom-containing groups) carbon-nitrogen, carbon-phosphorous, and/or carbon-silicon double bonds.

M is titanium, zirconium, or hafnium. In one embodiment, M is zirconium or hafnium, and in another embodiment M is hafnium. In another embodiment, M is zirconium. In some embodiments, M is in a formal oxidation state of +2, +3, or +4. In some embodiments, n is 0, 1, 2, or 3. Each X independently is a monodentate ligand that is neutral, monoanionic, or dianionic; or two Xs are taken together to form a bidentate ligand that is neutral, monoanionic, or dianionic. X and n are chosen in such a way that the metal-ligand complex of Formula (I) is, overall, neutral. In some embodiments each X independently is the monodentate ligand. In one embodiment, when there are two or more X monodentate ligands, each X is the same. In some embodiments the monodentate ligand is the monoanionic ligand. The monoanionic ligand has a net formal oxidation state of −1. Each monoanionic ligand may independently be hydride, $(C_1-C_{40})$ hydrocarbyl carbanion,
$(C_1-C_{40})$ heterohydrocarbyl carbanion, halide, nitrate, HC(O)O$^-$, $(C_1-C_{40})$ hydrocarbylC(O)O$^-$, HC(O)N(H)$^-$, $(C_1-C_{40})$ hydrocarbyl-C(O)N(H)$^-$, $(C_1-C_{40})$hydrocarbylC(O)N($(C_1-C_{20})$ hydrocarbyl)$^-$, $R^K R^L B^-$, $R^K R^L N^-$, $R^K O^-$, $R^K S^-$, $R^K R^L P^-$, or $R^M R^K R^L Si^-$, wherein each $R^K$, $R^L$, and $R^M$ independently is hydrogen, $(C_1-C_{40})$ hydrocarbyl, or $(C_1-C_{40})$heterohydrocarbyl, or $R^K$ and $R^L$ are taken together to form a $(C_2-C_{40})$ hydrocarbylene or $(C_1-C_{40})$ heterohydrocarbylene and $R^M$ is as defined above.

In some embodiments, at least one monodentate ligand of X independently is the neutral ligand. In one embodiment, the neutral ligand is a neutral Lewis base group that is $R^X NR^K R^L$, $R^K OR^L$, $R^K SR^L$, or $R^X PR^K R^L$, wherein each $R^X$ independently is hydrogen, $(C_1-C_{40})$ hydrocarbyl, [$(C_1-C_{10})$ hydrocarbyl]$_3$Si, [$(C_1-C_{10})$ hydrocarbyl]$_3$Si($C_1-C_{10}$) hydrocarbyl, or $(C_1-C_{40})$ hetero-hydrocarbyl and each $R^K$ and $R^L$ independently is as defined above.

In some embodiments, each X is a monodentate ligand that independently is a halogen atom, unsubstituted $(C_1-C_{20})$ hydrocarbyl, unsubstituted $(C_1-C_{20})$ hydrocarbylC(O)O—, or $R^K R^L N$— wherein each of $R^K$ and $R^L$ independently is an unsubstituted $(C_1-C_{20})$ hydrocarbyl. In some embodiments each monodentate ligand X is a chlorine atom, $(C_1-C_{10})$ hydrocarbyl (e.g., $(C_1-C_6)$alkyl or benzyl), unsubstituted $(C_1-C_{10})$ hydrocarbylC(O)O—, or $R^K R^L N$— wherein each of $R^K$ and $R^L$ independently is an unsubstituted $(C_1-C_{10})$ hydrocarbyl.

In some embodiments, there are at least two X and the two X are taken together to form the bidentate ligand. In some embodiments the bidentate ligand is a neutral bidentate ligand. In one embodiment, the neutral bidentate ligand is a diene of formula $(R^D)_2 C = C(R^D) - C(R^D) = C(R^D)_2$, wherein each $R^D$ independently is H, unsubstituted $(C_1-C_6)$ alkyl, phenyl, or naphthyl. In some embodiments the bidentate ligand is a monoanionic-mono(Lewis base) ligand. The monoanionic-mono(Lewis base) ligand may be a 1,3-dionate of formula (D): $R^E - C(O^-) = CH - C(= O) - R^E$ (D), wherein each $R^D$ independently is H, unsubstituted $(C_1-C_6)$ alkyl, phenyl, or naphthyl. In some embodiments the bidentate ligand is a dianionic ligand. The dianionic ligand has a net formal oxidation state of −2. In one embodiment, each dianionic ligand independently is carbonate, oxalate (i.e., $^-O_2CC(O)O^-$), $(C_2-C_{40})$ hydrocarbylene dicarbanion, $(C_1-C_{40})$ heterohydrocarbylene dicarbanion, or sulfate.

As previously mentioned, number and charge (neutral, monoanionic, dianionic) of X are selected depending on the formal oxidation state of M such that the metal-ligand complex of Formula (I) is, overall, neutral.

In some embodiments, each X is the same, wherein each X is methyl; ethyl; 1-propyl; 2-propyl; 1-butyl; 2,2,-dimethylpropyl; trimethylsilylmethyl; phenyl; benzyl; or chloro. In some embodiments n is 2 and each X is the same.

In some embodiments, at least two X are different. In some embodiments, n is 2 and each X is a different one of methyl; ethyl; 1-propyl; 2-propyl; 1-butyl; 2,2,-dimethylpropyl; trimethylsilylmethyl; phenyl; benzyl; and chloro.

The integer n indicates number of X. In one embodiment, n is 2 or 3, and at least two X independently are monoanionic monodentate ligands, and a third X, if present, is a neutral monodentate ligand. In some embodiments n is 2, at two X are taken together to form a bidentate ligand. In some embodiments, the bidentate ligand is 2,2-dimethyl-2-silapropane-1,3-diyl or 1,3-butadiene.

In some embodiments, each Z independently is O, S, —N[($C_1$-$C_{40}$)hydrocarbyl]—, or —P[($C_1$-$C_{40}$) hydrocarbyl]—. In some embodiments, each Z is different. In some embodiments, one Z is O, and one Z is —N($CH_3$)—. In some embodiments, one Z is O, and one Z is S. In some embodiments, one Z is S, and one Z is —N[)$C_1$-$C_{40}$) hydrocarbyl]- (e.g., —N($CH_3$)—). In some embodiments, each Z is the same. In some embodiments, each Z is O. In some embodiments, each Z is S. In some embodiments, each Z is —N[($C_1$-$C_{40}$)hydrocarbyl] (e.g.,—N($CH_3$)-). In some embodiments, at least one, and in some embodiments each Z is —[($C_1$-$C_{40}$)hydrocarbyl] e.g., —P($CH_3$)—).

In some embodiments, L is selected from the following: —$CH_2$—, —$CH_2CH_2$—, —$CH_2CH_2CH_2$—; —CH($CH_3$)$CH_2$CH($CH_3$)—; —CH($CH_3$)CH($CH_3$)CH($CH_3$)—; —$CH_2$C($CH_3$)$_2$$CH_2$—; 1,3-cyclopentane-diyl; or 1,3-cyclohexane-diyl. In some embodiments L comprises the 4-carbon atom linker backbone (e.g., L is —$CH_2CH_2CH_2CH_2$—; —$CH_2$C($CH_3$)$_2$C($CH_3$)$_2$$CH_2$—; 1,2-bis(methylene)cyclohexane; or 2,3-bis(methylene)-bicyclco[2.2.2]octane). In some embodiments L comprises the 5-carbon atom linker backbone (e.g., L is —$CH_2CH_2CH_2CH_2CH_2$— or 1,3-bis(methylene)cyclohexane). In some embodiments L comprises the 6-carbon atom linker backbone (e.g., L is —$CH_2CH_2CH_2CH_2CH_2CH_2$— or 1,2-bis(ethylene)cyclohexane).

Co-catalyst Component

The procatalyst comprising the metal-ligand complex of Formula (I) is rendered catalytically active by contacting it to, or combining it with, the activating co-catalyst or by using an activating technique such as those that are known in the art for use with metal-based olefin polymerization reactions. Suitable activating co-catalysts for use herein include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is bulk electrolysis. Combinations of one or more of the foregoing activating co-catalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Aluminoxanes and their preparations are known at, for example, United States Patent Number (USPN) U.S. Pat. No. 6,103,657. Examples of preferred polymeric or oligomeric alumoxanes are methylalumoxane, triisobutylaluminum-modified methylalumoxane, and isobutylalumoxane.

Exemplary Lewis acid activating co-catalysts are Group 13 compounds containing from 1 to 3 hydrocarbyl substituents as described herein. In some embodiments, exemplary Group 13 metal compounds are tri(hydrocarbyl)-substituted-aluminum or tri(hydrocarbyl)-boron compounds. In some other embodiments, exemplary Group 13 metal compounds are tri(hydrocarbyl)-substituted-aluminum or tri(hydrocarbyl)-boron compounds are tri(($C_1$-$C_{10}$)alkyl)aluminum or tri(($C_6$-$C_{18}$)aryl)boron compounds and halogenated (including perhalogenated) derivatives thereof. In some other embodiments, exemplary Group 13 metal compounds are tris(fluoro-substituted phenyl)boranes, in other embodiments, tris(pentafluorophenyl)borane. In some embodiments, the activating co-catalyst is a tris(($C_1$-$C_{20}$) hydrocarbyl) borate (e.g., trityl tetrafluoroborate) or a tri(($C_1$-$C_{20}$) hydrocarbyl)ammonium tetra(($C_1$-$C_{20}$) hydrocarbyl)borane (e.g., bis(octadecyl)methyl-ammonium tetrakis(pentafluorophenyl)borane). As used herein, the term "ammonium" means a nitrogen cation that is a (($C_1$-$C_{20}$) hydrocarbyl)$_4$N$^+$, a (($C_1$-$C_{20}$)hydrocarbyl)$_3$N(H)$^+$, a (($C_1$-$C_{20}$)-hydrocarbyl)$_2$N(H)$_2$+, ($C_1$-$C_{20}$) hydrocarbylN(H)$_3^+$, or N(H)$_4^+$, wherein each ($C_1$-$C_{20}$)hydrocarbyl may be the same or different.

Exemplary combinations of neutral Lewis acid activating co-catalysts include mixtures comprising a combination of a tri(($C_1$-$C_4$)alkyl)aluminum and a halogenated tri(($C_6$-$C_{18}$) aryl)boron compound, especially a tris(pentafluorophenyl) borane. Other exemplary embodiments are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Exemplary embodiments ratios of numbers of moles of (metal-ligand complex): (tris(pentafluoro-phenylborane): (alumoxane) [e.g., (Group 4 metal-ligand complex):(tris(pentafluoro-phenylborane): (alumoxane)] are from 1:1:1 to 1:10:30, other exemplary embodiments are from 1:1:1.5 to 1:5:10.

Many activating co-catalysts and activating techniques have been previously taught with respect to different metal-ligand complexes in the following USPNs: U.S. Pat. Nos. 5,064,802; 5,153,157; 5,296,433; 5,321,106; 5,350,723; 5,425,872; 5,625,087; 5,721,185; 5,783,512; 5,883,204; 5,919,983; 6,696,379; and 7,163,907. Examples of suitable hydrocarbyloxides are disclosed in U.S. Pat. No. 5,296,433. Examples of suitable Bronsted acid salts for addition polymerization catalysts are disclosed in U.S. Pat. Nos. 5,064,802; 5,919,983; 5,783,512. Examples of suitable salts of a cationic oxidizing agent and a non-coordinating, compatible anion as activating co-catalysts for addition polymerization catalysts are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts as activating co-catalysts for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155 B1 beginning at column 50, at line 39, and going through column 56, at line 55, only the portion of which is incorporated by reference herein.

In some embodiments, the procatalyst comprising the metal-ligand complex of Formula (I) may be activated to form an active catalyst composition, by combination with one or more cocatalyst, such as a cation forming cocatalyst, a strong Lewis acid, or a combination thereof. Suitable cocatalysts for use, include polymeric or oligomeric aluminoxanes, especially methyl aluminoxane, as well as inert, compatible, noncoordinating, ion forming compounds. Exemplary suitable cocatalysts include, but are not limited to, modified methyl aluminoxane (MMAO), bis(hydrogenated tallow alkyl)methyl, tetrakis(pentafluorophenyl)borate(1-) amine, triethyl aluminum (TEA), and any combinations thereof.

In some embodiments, one or more of the foregoing activating co-catalysts are used in combination with each other. An especially preferred combination is a mixture of a tri(($C_1$-$C_4$) hydrocarbyl)aluminum, tri(($C_1$-$C_4$) hydrocarbyl) borane, or an ammonium borate with an oligomeric or polymeric alumoxane compound.

The ratio of total number of moles of one or more metal-ligand complexes of Formula (I) to total number of moles of one or more of the activating co-catalysts is from 1:10,000 to 100:1. In some embodiments, the ratio is at least 1:5000, in some other embodiments, at least 1:1000; and 10:1 or less, and in some other embodiments, 1:1 or less. When an alumoxane alone is used as the activating co-catalyst, preferably the number of moles of the alumoxane that are employed is at least 10 times, further at least 40 times, further at least 100 times the number of moles of the metal-ligand complex of formula (I). When tris(pentafluorophenyl)borane alone is used as the activating co-catalyst, in some other embodiments, the number of moles of the tris(pentafluoro-phenyl)borane that are employed to the total number of moles of one or more metal-ligand complexes of Formula (I) from 0.5:1 to 10:1, in some other embodiments, from 1:1 to 6:1, in some other embodiments, from 1:1 to 5:1. The remaining activating co-catalysts are generally employed in approximately mole quantities equal to the total mole quantities of one or more metal-ligand complexes of formula (I).

Catalyst System Properties

The inventive catalyst composition comprising" a) the procatalyst, comprising the metal-ligand complex of Formula (I), and b) one or more cocatalyst, as described herein, has the capability to produce polymeric materials with native weight-average molecular weights ($M_w$), in the range greater than 250,000 g/mole, for example, greater than 500,000 g/mole, preferably greater than 750,000, more preferably greater than 900,000 g/mole, most preferably greater than 1,000,000 g/mole, at temperatures at, or greater than, 130° C., for example, at, or greater than, 140° C., as produced in batch reactor experiments described below. The term "native," in reference to the weight-average molecular weight, refers to batch reactor experiments where no dihydrogen ($H_2$) is added, resulting in the production of polymeric material, with the highest possible Mw, under the batch reactor conditions described. The inventive catalyst composition comprising a) the procatalyst, comprising the metal-ligand complex of Formula (I), and b) one or more cocatalyst, as described herein, should preferentially exhibit good responsiveness to dihydrogen ($H_2$) in batch reactor production, which is used to control the polymer $M_w$, so that a reduction of the native Mw by at least 70%, preferentially by at least 75%, even more preferentially by at least 80%, and most preferentially by at least 85%. The inventive catalyst composition comprising a) the procatalyst comprising the metal-ligand complex of Formula (I) and b) one or more cocatalyst, as described herein, should also preferentially exhibit good responsiveness to dihydrogen ($H_2$) in a continuous process (as described below), so that polymers with $M_w$ in the range of, for example, 50,000 g/mol to 200,000 g/mol, can be produced by using less than 1 mol % of dihydrogen, preferably less than 0.80 mol % of dihydrogen, more preferably less than 0.60 mol % of dihydrogen, even more preferably less than 0.40 mol % of dihydrogen, most preferably less than 0.20 mol % of dihydrogen. The mol % hydrogen is measured in terms of the moles of hydrogen with respect to the total moles of hydrogen and ethylene added to the reactor in a continuous process.

The inventive catalyst composition comprising a) the procatalyst and b) one or more cocatalyst, as described herein, has catalytic efficiency greater than 100,000 g of polymer per gram of active metal center; for example, from greater than 500,000 g of polymer per gram of active metal center. The catalytic efficiency is measured in terms of amount of polymer produced relative to the amount of catalyst used in solution polymerization process, wherein the polymerization temperature is at least 130° C., for example, in the range from 140 to 195° C., or from 150 to 195° C., and ethylene concentration is greater than 5 g/L, for example, greater than 6 g/L, and wherein the ethylene conversion is greater than 70 percent, for example, greater than 75 percent or greater than 80 percent, or in the alternative, greater than 90 percent.

Process for Producing Procatalyst

In some embodiments, the ligands of the invention may be prepared using known procedures. Specifically, the ligands of the invention may be prepared using a variety of synthetic routes, depending on the variation desired in the ligand. In general, building blocks are prepared that are then linked together with a bridging group. Variations in the R group substituents can be introduced in the synthesis of the building blocks.

Variations in the bridge can be introduced with the synthesis of the bridging group. Specific ligands within the scope of this invention may be prepared according to the general schemes shown below, where building blocks are first prepared, and then coupled together. There are several different ways to use these building blocks. In one embodiment, generally, each of the optionally substituted phenyl rings is prepared as a separate building block. The desired optionally substituted phenyls are then combined into biphenyl building blocks, which are then bridged together. In another embodiment, the optionally substituted phenyl building blocks are bridged together, and then additional, optionally substituted phenyl building blocks are added to form the bridged bi-aryl structures. The starting materials or reagents used are generally commercially available, or are prepared via routine synthetic means.

In the schemes below, the term ligand refers to the organic precursor to the pro-catalyst. The pro-catalyst is derived from a reaction of the ligand with a suitable metallic (titanium, zirconium, or hafnium) precursor. Common abbreviations are listed in the key system below.

LG: generic leaving group
PG: generic protecting group, common examples include:

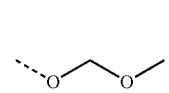
methoxymethyl ether (MOM)

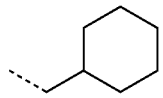
tetrahydropyranyl ether (THP)

R, L, M, Z, X : as defined above
Ha: halide, most commonly Br or I; Me: methyl; Et: ethyl; Ph: phenyl; i-Pr: iso-propyl; t-Bu: tert-butyl; t-Oct: tert-octyl; Ts: toluene sulfonate; THF: tetrahydrofuran; Et$_2$O: diethyl ether; DMF: dimethylformamide; EtOAc: ethyl acetate; DIAD: diisopropyl azodicarboxylate; GC: gas chromatography; LC: liquid chromatography; TLC: thin layer chromatography; NMR: nuclear magnetic resonance; PTSA: para-toluene sulfonic acid; NIS: N-iodosuccinimide 1a. Preparation of 2-substituted Protected phenols (Protocol 1, carbon-nitrogen Coupling).

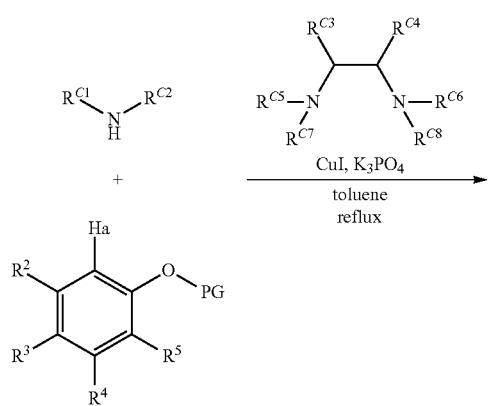

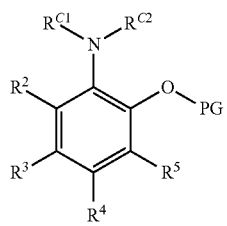

A three-necked, round-bottomed flask, in a glove box, is charged with the desired protected phenol (approximately 1.0 equivalents), the desired aryl-nitrogen compound or nitrogen heterocyclic (approximately 0.6 equivalents), K$_3$PO$_4$ (approximately 2.1 equivalents), anhydrous CuI (approximately 0.03 equivalents), dried toluene (approximately 2 mL per mmol of phenol), and an appropriate N,N'-disubstituted diamine (approximately 0.08 equivalents). The reaction mixture is then heated under reflux. The reaction progress can be monitored by a suitable technique (e.g. GC/MS, NMR spectroscopy, TLC), and, in some cases, additional anhydrous CuI (approximately 0.03 equivalents) and N,A1' - disubstituted diamine (approximately 0.08 equivalents) is added to the mixture, and heating under reflux continued, until such a time, when the conversion is observed to be complete. The reaction is then allowed to cool to room temperature, and filtered through a small silica plug, washed with THF, and concentrated, to give the crude product. This crude material can be purified by either recrystallization or flash chromatography on silica gel.

1b. Preparation of 2-substituted Protected phenols (Protocol 2, carbon-carbon Coupling).

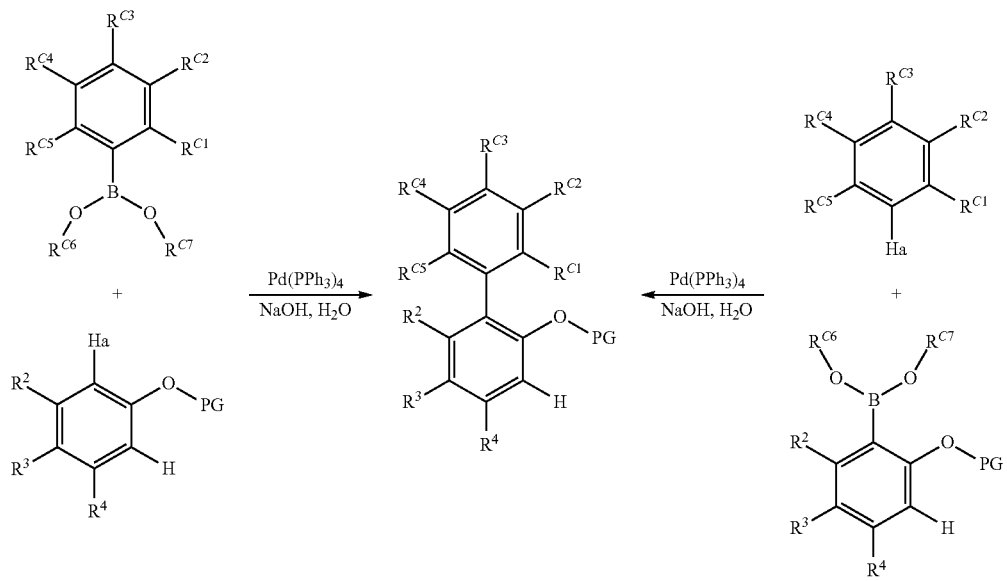

A three-neck, round-bottomed flask, placed under a nitrogen atmosphere, is charged with approximately equimolar quantities of the aryl halide and the borylated aryl compound, NaOH (approximately 6 equivalents relative to aryl halide), Pd(PPh$_3$)$_4$ (approximately 0.02 equivalents relative to aryl halide), degassed toluene (approximately 5 mL per mmol of aryl halide), and degassed water (approximately 1 mL per mmol of aryl halide). The system is nitrogen-sparged, and the contents are then heated to 110° C. for approximately 24 hours. The reaction is cooled, and the volatiles removed under vacuum. The residue is taken up in Et$_2$O, washed with brine, dried over anhydrous magnesium sulfate, filtered through a pad of silica gel, and then concentrated. This crude material can be purified by either recrystallization or flash chromatography on silica gel.

2. Preparation of Borylated 2-substituted Protected phenols:

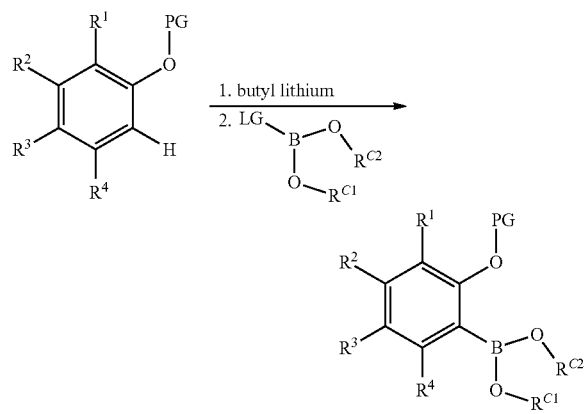

To an oven dried, three-neck, round-bottomed flask, under nitrogen atmosphere, is added the desired protected phenol (approximately 1.0 equivalents) and dry THF (approximately 6 mL per mmol of protected phenol). This solution was cooled to approximately 0-10° C. (ice-water bath), and 2.5 M n-butyl lithium in hexanes (approximately 2.2 equivalents) is added slowly. After stirring for approximately 4 hours, the desired boronic ester or boronic acid (approximately 2.2 equivalents) is added slowly. The mixture is stirred for one hour at approximately 0-10° C., before allowing the reaction to warm to room temperature, and then stirred for approximately 18 hours. To the reaction mixture is added cold, saturated aqueous sodium bicarbonate (approximately 6 mL per mmol of protected phenol). The mixture is extracted with several portions of methylene chloride. The organic phases are combined, and washed with cold saturated aqueous sodium bicarbonate, brine, then dried over anhydrous magnesium sulfate, filtered, and concentrated to give the crude product. Purification can be accomplished by recrystallization from a suitable solvent (e.g., acetonitrile, toluene, hexane, or methanol).

3a. Preparation of Symmetrical Bridging Fragments.

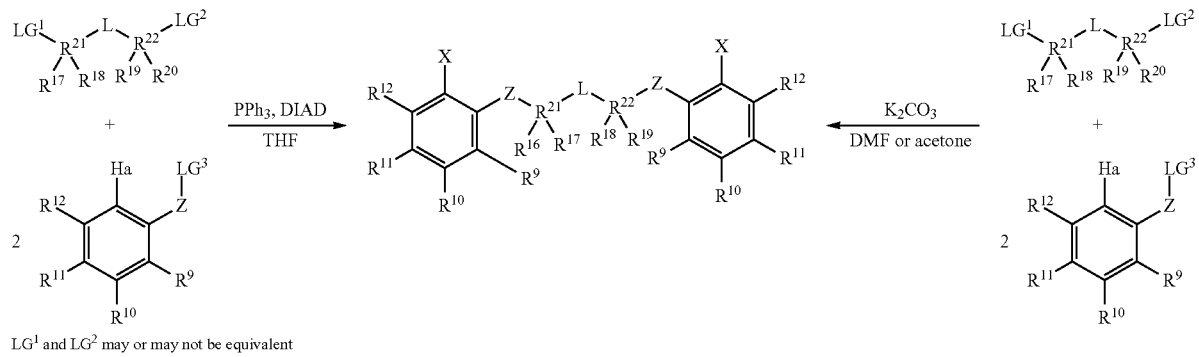

Mitsonobu-type: An oven dried, three-neck, round-bottomed flask, equipped with an addition funnel, is placed under nitrogen atmosphere, and charged with the desired aryl halide (approximately 1.0 equivalents), the desired connecting unit (containing the L moiety and the $R^{17}$-$R^{22}$ groups, approximately 0.45 equivalents), triphenylphosphine (approximately 1.0 equivalents), and THF (approximately 1.0 mL per mmol of aryl halide). The addition funnel is then charged with DIAD (approximately 1.0 equivalents) and THF (approximately 0.5 mL per mmol of aryl halide). The contents in the flask are cooled to approximately 2-5° C., in an ice-water bath, and the DIAD solution in the addition funnel is added, at such a rate, to maintain the reaction temperature at 2-5° C. The resulting mixture is stirred at 2-5° C. for an additional one hour, subsequent to the DIAD addition, then allowed to warm up to ambient temperature, and stirred overnight. The volatiles are removed under vacuum, and the resulting residue is extracted with alkane solvent, and sequentially washed with 1M NaOH, water, 1N HCl and water. The organic portion is collected, and dried under vacuum. Purification can be accomplished by recrystallization from a suitable solvent (e.g. acetonitrile, toluene, hexane, or methanol), or column chromatography on silica gel.

S$_N$2-type: To a solution of the desired aryl halide (approximately 1.0 equivalents) and desired connecting unit (containing the L moiety and the $R^{17}$-$R^{22}$ groups, approximately 0.45 equivalents), in acetone (approximately 7.0 mL per mmol of aryl halide), is added K$_2$CO$_3$ (approximately 2.5 equivalents). The reaction mixture is then heated under reflux for approximately 36 hours. The resulting suspension is then cooled, filtered, and concentrated under vacuum. Purification can be accomplished by recrystallization from a suitable solvent (e.g. acetonitrile, toluene, hexane, or methanol), or column chromatography on silica gel.

3b. Preparation of Unsymmetrical Bridging Fragments.

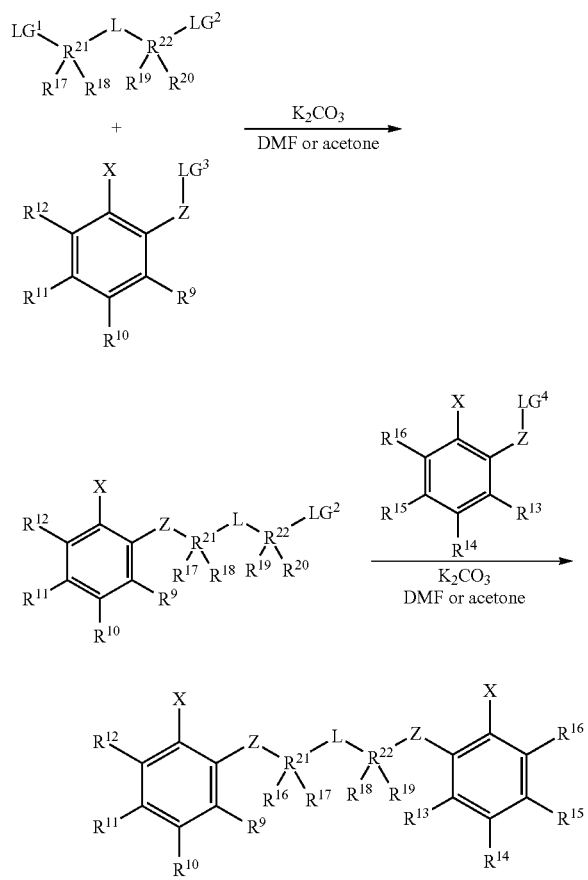

LG$^1$ may or may not be equivalent to LG$^2$
LG$^3$ may or may not be equivalent to LG$^4$ To a solution of the desired aryl halide (approximately 1.0 equivalents) and desired connecting unit (containing the L moiety and the $R^{17}$-$R^{22}$ groups, approximately 1.5 equivalents), in acetone (approximately 7.0 mL per mmol of aryl halide,) is added $K_2CO_3$ (approximately 2.5 equivalents). The reaction mixture is then heated under reflux for approximately 36 hours. The resulting suspension is then cooled, filtered, and concentrated under vacuum. Purification can be accomplished at this stage by recrystallization from a suitable solvent (e.g. acetonitrile, toluene, hexane, or methanol), or column chromatography on silica gel. The obtained material is then subjected to an analogous sequential reaction, by combining it with another aryl halide (approximately 1.0 equivalents), and $K_2CO_3$ (approximately 2.5 equivalents), in acetone (approximately 7.0 mL per mmol of aryl halide), and heating under reflux. The resulting suspension is then cooled, filtered, and concentrated under vacuum. Purification can be accomplished recrystallization from a suitable solvent (e.g. acetonitrile, toluene, hexane, or methanol), or column chromatography on silica gel.

5a. Preparation of Ligand (Simultaneous Double Suzuki Reaction).

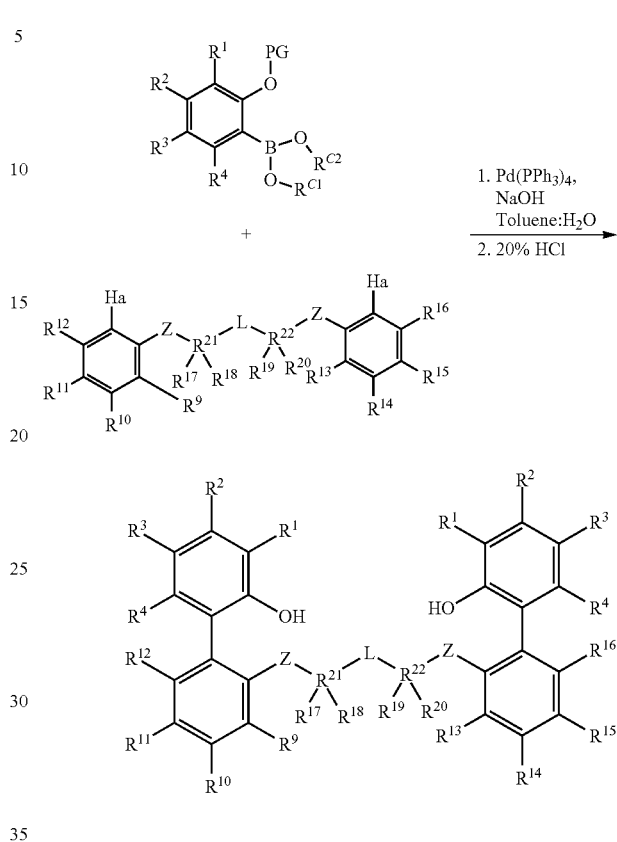

To an oven dried, three-neck, round-bottomed flask, under nitrogen atmosphere, is added the bis-arylhalide (approximately 1.0 equivalents) and the borylated protected phenol (approximately 2.2 equivalents) dissolved in toluene (approximately 5 mL per mmol of bis-arylhalide), under a nitrogen atmosphere with stirring. To this, is added, NaOH (approximately 1.0 equivalents) dissolved in water, (approximately 10 mL per mmol of NaOH), followed by quick addition of $Pd(PPh_3)_4$ (approximately 0.04 equivalents), and the reaction heated to 88° C. The course of the reaction can be monitored via LC. When deemed complete, the reaction vessel is cooled to ambient temperature, and the stirring halted. The caustic layer is removed from the resulting bisphasic mixture, and a 20% aqueous HCl solution is added (approximately 1.5 mL per mmol of bis-arylhalide) to the remaining organic portion. The resulting mixture is heated under reflux for approximately 8 hours. The reactor is cooled to ambient temperature, the aqueous layer removed, and the organic layer washed with brine, and then dried over $MgSO_4$. This mixture is filtered, and concentrated, to provide the crude product, which can be purified by recrystallization from a suitable solvent (e.g. acetonitrile, toluene, hexane, or methanol), or column chromatography on silica gel.

5b. Preparation of Ligand (Sequential Suzuki Reactions).

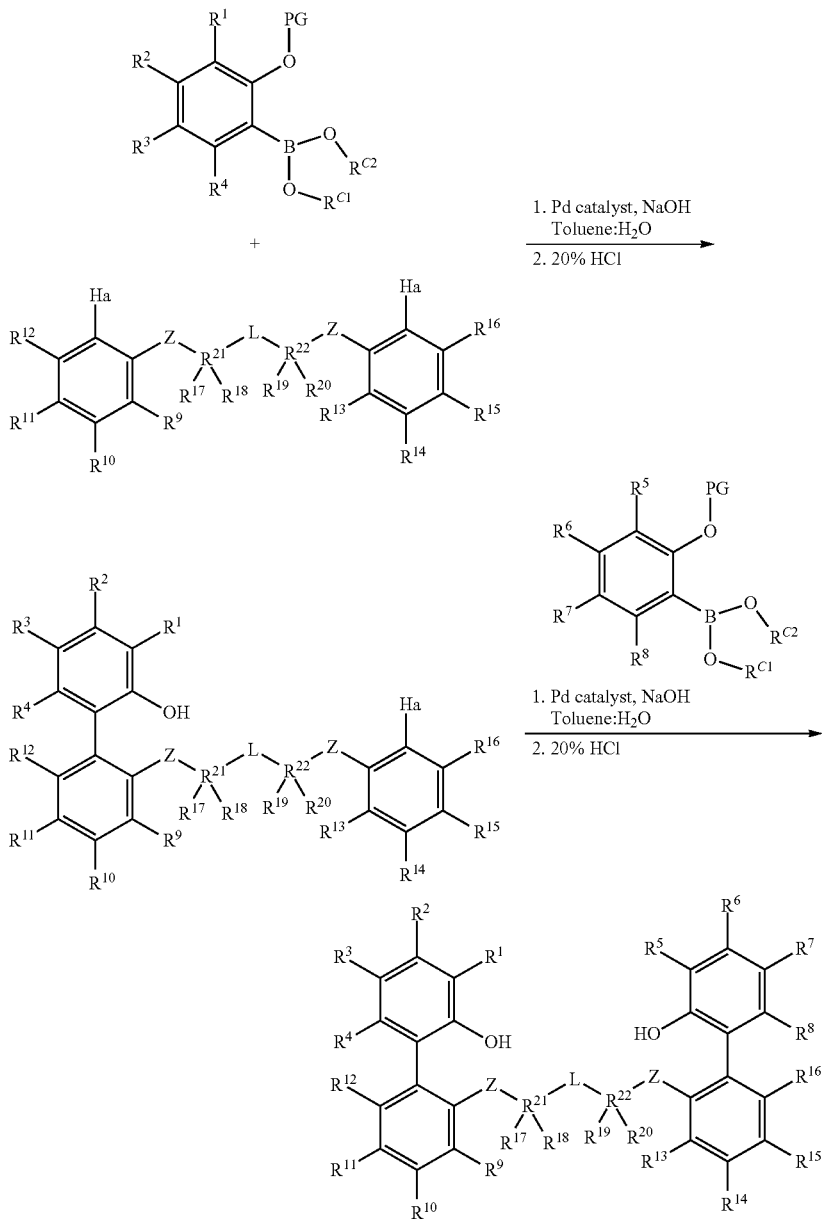

To an oven dried, three-neck, round-bottomed flask, under nitrogen atmosphere, is added the bis-arylhalide (approximately 1.0 equivalents) and the borylated protected phenol (approximately 1.0 equivalents) dissolved in toluene (approximately 5 mL per mmol of bis-arylhalide), under a nitrogen atmosphere with stirring. To this is added, NaOH (approximately 1.0 equivalents) dissolved in water, (approximately 10 mL per mmol of NaOH), followed by quick addition of a suitable palladium catalyst (approximately 0.04 equivalents), and the reaction is heated to 88° C. The course of the reaction can be monitored via LC. When deemed complete, the reaction vessel is cooled to ambient temperature, and the second borylated protected phenol (approximately 1.0 equivalents), and a suitable palladium catalyst (approximately 0.04 equivalents). The reaction is heated to 88° C., and the course of the reaction can be again be monitored via LC. When deemed complete, the reaction vessel is cooled to ambient temperature, and the stirring halted. The caustic layer is removed from the resulting bisphasic mixture, and a 20% aqueous HCl solution is added (approximately 1.5 mL per mmol of bis-arylhalide) to the remaining organic portion. The resulting mixture is heated under reflux for approximately 8 hours. The reactor is cooled to ambient temperature, the aqueous layer removed, and the organic layer washed with brine, and then dried over $MgSO_4$. This mixture is filtered, and concentrated, to provide the crude product, which can be purified by recrystallization from a suitable solvent (e.g. acetonitrile, toluene, hexane, or methanol), or column chromatography on silica gel.

7. Preparation of Pro-catalyst.

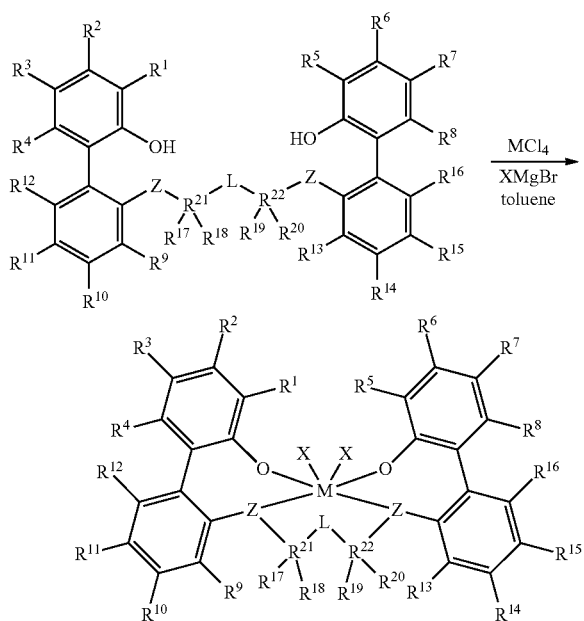

An oven, dried three-neck, round-bottomed flask, under nitrogen atmosphere, is charged with $MCl_4$ (approximately 1.0 equivalents) and cold toluene or hexane (approximately 10 mL per mmol of ligand, at −40 to −20° C. XMgBr (approximately 4.0 equivalents) is then added to the cold suspension, and the resulting mixture is stirred for 2-15 minutes. The ligand (approximately 0.95 equivalents) is then added, and the reaction mixture is allowed to warm to ambient temperature, and stirred for approximately 4 hours, and then dried under vacuum. The resulting residue is extracted with hexane and/or toluene, filtered, and dried under vacuum. This crude material can be further purified by recrystallization from a suitable solvent (e.g. hexane, toluene).

Olefin-based Polymers

The inventive catalyst compositions comprising one or more procatalyst, comprising the metal-ligand complex of Formula (I), and one or more cocatalysts, may be employed to prepare a variety of olefin based polymers including, but not limited to, ethylene based polymers, for example homopolymers and/or interpolymers (including copolymers) of ethylene, and optionally one or more comonomers such as a-olefins, and propylene based polymers, for example homopolymers and/or interpolymers (including copolymers) of propylene, and optionally one or more comonomers, such as ethylene or α-olefins.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure) and the term interpolymer as defined hereinafter. Trace amounts of impurities, for example, catalyst residues, may be incorporated into and/or within the polymer.

The term "interpolymer," as used herein, refers to polymers prepared by the polymerization of at least two different types of monomers. The generic term interpolymer thus includes copolymers (employed to refer to polymers prepared from two different types of monomers), and polymers prepared from more than two different types of monomers.

The term, "olefin-based polymer," as used herein, refers to a polymer that comprises, in polymerized form, a majority amount of olefin monomer, for example ethylene or propylene (based on the weight of the polymer), and optionally may comprise one or more comonomers.

The term, "ethylene-based polymer," as used herein, refers to a polymer that comprises, in polymerized form, a majority amount of ethylene monomer (based on the weight of the polymer), and optionally may comprise one or more comonomers.

The term, "propylene-based polymer," as used herein, refers to a polymer that comprises, in polymerized form, a majority amount of propylene monomer (based on the weight of the polymer), and optionally may comprise one or more comonomers.

Ethylene-based Polymers

The inventive ethylene based polymers, for example homopolymers and/or interpolymers (including copolymers) of ethylene and optionally one or more comonomers, such as α-olefins, according to instant invention, have a density in the range of 0.855 to 0.973 g/cm³. All individual values and subranges from 0.855 to 0.973 g/cm³ are included herein and disclosed herein; for example, the density can be from a lower limit of 0.855, 0.880, 0.885, 0.900, 0.905, 0.910, 0.915, or 0.920 g/cm³ to an upper limit of 0.973, 0.963, 0.960, 0.955, 0.950, 0.945, 0.940, 0.935, 0.930, 0.925, 0.920, 0.915, 0.910, or 0.905 g/cm³.

In one particular embodiment, the inventive ethylene based polymers, for example homopolymers and/or interpolymers (including copolymers) of ethylene and optionally one or more comonomers such as α-olefins have a long chain branching frequency in the range of from 0.0 to 3 long chain branches (LCB) per 1000C.

In one particular embodiment, the inventive ethylene based polymers, for example homopolymers and/or interpolymers (including copolymers) of ethylene and optionally one or more comonomers, such as a-olefins, according to this invention have a molecular weight distribution ($M_w/M_n$)) (measured according to the conventional GPC method) in the range of from greater than, or equal to, 2. All individual values and subranges from greater than, or equal to, 2 are included herein and disclosed herein; for example, the ethylene/α-olefin interpolymer may have a molecular weight distribution ($M_w/M_n$) in the range from 2 to 10; or in the alternative, the ethylene/α-olefin interpolymer may have a molecular weight distribution ($M_w/M_n$) in the range from 2 to 5.

In one particular embodiment, the inventive ethylene based polymers, for example homopolymers and/or interpolymers (including copolymers) of ethylene, and optionally one or more comonomers, such as α-olefins, have a weight average molecular weight ($M_w$) in the range from equal to, or greater than, 20,000 g/mole, for example, in the range from 20,000 to 350,000 g/moles.

In one particular embodiment, the inventive ethylene based polymers, for example homopolymers and/or interpolymers (including copolymers) of ethylene, and optionally one or more comonomers, such as α-olefins, have a melt index ($I_2$) in the range of 0.1 to 200 g/10 minutes. All individual values and subranges from 0.1 to 200 g/10 minutes are included herein and disclosed herein; for example, the melt index ($I_2$) can be from a lower limit of 0.1, 0.2, 0.5, 0.6, 0.8, 1, 1.5, 2.0, 2.5, 3.0, 3.5, 4.0, 4.5, 5.0, 10, 15, 20, 30, 40, 50, 60, 80, 90, 100, or 150 g/10 minutes, to an upper limit of 0.9, 1, 1.5, 2.0, 2.5, 3.0, 3.5, 4.0, 4.5, 5.0, 10, 15, 20, 30, 40, 50, 60, 80, 90, 100, 150, or 200 g/10 minutes.

In one embodiment, the inventive ethylene based polymers produced by one or more inventive catalyst compositions, and optionally one or more other catalyst compositions, for example, homopolymers and/or interpolymers (including copolymers) of ethylene, and optionally one or more comonomers, such as a-olefins, have a melt flow ratio ($I_{10}/I_2$) in the range of from 5 to 30. All individual values and subranges from 5 to 30 are included herein and disclosed herein; for example, the melt flow ratio ($I_{10}/I_2$) can be from a lower limit of 5, 5.5, 6, 6.5, 7, 7.5, 8, 10, 12, 15, 20, or 25 to an upper limit of 5.5, 6, 6.5, 7, 7.5, 8, 10, 12, 15, 20, 25, or 30.

In one particular embodiment, the inventive ethylene based polymers, for example homopolymers and/or interpolymers (including copolymers) of ethylene, and optionally one or more comonomers, such as α-olefins, have a zero shear viscosity ratio (ZSVR) in the range of from equal to, or greater than, 1.0; for example from 1.0 to 10.0; or in the alternative, from 1.0 to 8.0; or in the alternative, from 1.0 to 7.0; or in the alternative, from 1.0 to 5.0; or in the alternative, from 1.0 to 4.0; or in the alternative, from 1.0 to 3.0; or in the alternative, from 1.0 to 2.5, or in the alternative, from 1.0 to 2.0; or in the alternative, from 1.2 to 2.5, or in the alternative, from 1.2 to 2.0.

In one embodiment, the inventive ethylene based polymers, for example homopolymers and/or interpolymers (including copolymers) of ethylene, and optionally one or more comonomers, such as α-olefins, may further comprise at least 0.01 parts by weight of metal residues and/or metal oxide residues, remaining from the inventive catalyst system, per one million parts of the inventive ethylene based polymers, for example homopolymers and/or interpolymers (including copolymers) of ethylene, and optionally one or more comonomers, such as a-olefins. The metal residues and/or metal oxide residues, remaining from the catalyst system in the inventive ethylene based polymers, for example homopolymers and/or interpolymers (including copolymers) of ethylene, and optionally one or more comonomers, such as α-olefins, may be measured by X-ray fluorescence (XRF), which is calibrated to reference standards.

The inventive ethylene based polymers, such as interpolymers (including copolymers) of ethylene, and optionally one or more comonomers, such as a-olefins, may comprise less than 48 percent by weight of units derived from one or more a-olefin comonomers. All individual values and subranges from less than 48 weight percent are included herein and disclosed herein; for example, the inventive ethylene based polymers such as interpolymers (including copolymers) of ethylene, and optionally one or more comonomers, such as α-olefins, may comprise from less than 37 percent by weight of units derived from one or more α-olefin comonomers; or in the alternative, less than 30 percent by weight of units derived from one or more α-olefin comonomers; or in the alternative, less than 23 percent by weight of units derived from one or more α-olefin comonomers; and at least 0 percent by weight of units derived by α-olefin comonomer(s); or in the alternative, at least 1.3 percent by weight of units derived by α-olefin comonomer(s); or in the alternative, at least 2.8 percent by weight of units derived by α-olefin comonomer(s); or in the alternative, at least 9.5 percent by weight of units derived by α-olefin comonomer(s).

The inventive ethylene based polymers, such as interpolymers (including copolymers) of ethylene, and optionally one or more comonomers, such as α-olefins, may comprise less than 20 percent by moles of units derived from one or more α-olefin comonomers. All individual values and subranges from less than 20 mole percent are included herein and disclosed herein; for example, the inventive ethylene based polymers, such as interpolymers (including copolymers) of ethylene, and optionally one or more comonomers, such as α-olefins, have may comprise from less than 13 percent by moles of units derived from one or more α-olefin comonomers; or in the alternative, from less than 9.5 percent by moles of units derived from one or more α-olefin comonomers; or in the alternative, from less than 7.0 percent by moles of units derived from one or more α-olefin comonomers; and at least 0 percent by moles of units derived by α-olefin comonomer(s); or in the alternative, at least 0.3 percent by moles of units derived by α-olefin comonomer(s); or in the alternative, at least 0.7 percent by moles of units derived by α-olefin comonomer(s); or in the alternative, at least 2.5 percent by moles of units derived by α-olefin comonomer(s).

The α-olefin comonomers typically have no more than 20 carbon atoms. For example, the α-olefin comonomers may preferably have 3 to 10 carbon atoms, and more preferably 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene. The one or more α-olefin comonomers may, for example, be selected from the group consisting of propylene, 1-butene, 1-hexene, and 1-octene; or in the alternative, from the group consisting of 1-hexene and 1-octene.

The inventive ethylene based polymers, for example homopolymers and/or interpolymers (including copolymers) of ethylene, and optionally one or more comonomers, such as α-olefins, may comprise at least 52 percent by weight of units derived from ethylene. All individual values and subranges from at least 52 weight percent are included herein and disclosed herein; for example, the inventive ethylene based polymers, for example homopolymers and/or interpolymers (including copolymers) of ethylene, and optionally one or more comonomers, such as α-olefins, may comprise at least 63 percent by weight of units derived from ethylene; or in the alternative, at least 70 percent by weight of units derived from ethylene; or in the alternative, at least 77 percent by weight of units derived from ethylene; and at most 100 percent by weight of units derived by ethylene; or in the alternative, at most 98.7 percent by weight of units derived by ethylene; or in the alternative, at most 97.2 percent by weight of units derived by ethylene; or in the alternative, at most 90.5 percent by weight of units derived by ethylene.

The inventive ethylene based polymers, for example homopolymers and/or interpolymers (including copolymers) of ethylene, and optionally one or more comonomers, such as α-olefins, may comprise at least 80 percent by moles of units derived from ethylene. All individual values and subranges from at least 80 mole percent are included herein and disclosed herein; for example, the inventive ethylene based polymers, for example homopolymers and/or interpolymers (including copolymers) of ethylene, and optionally one or more comonomers, such as α-olefins, may comprise at least 87 percent by moles of units derived from ethylene; or in the alternative, at least 91 percent by moles of units derived from ethylene; or in the alternative, at least 93 percent by moles of units derived from ethylene; and at most 100 percent by moles of units derived by ethylene; or in the alternative, at most 99.7 percent by moles of units derived by ethylene; or in the alternative, at most 99.3 percent by moles of units derived by ethylene; or in the alternative, at most 97.5 percent by moles of units derived by ethylene.

The inventive ethylene based polymers, for example homopolymers and/or interpolymers (including copolymers) of ethylene, and optionally one or more comonomers, such as α-olefins, may be produced using hydrogen as a train transfer agent to control molecular weight.

Any conventional polymerization process may be employed to produce the inventive ethylene based polymers, for example homopolymers and/or interpolymers (including copolymers) of ethylene, and optionally one or more comonomers, such as α-olefins. Such conventional polymerization processes include, but are not limited to, solution polymerization process, using one or more conventional reactors, for example, loop reactors, isothermal reactors, stirred tank reactors, batch reactors in parallel, series, and/or any combinations thereof.

In general, the solution phase polymerization process occurs in one or more well-stirred reactors, such as one or more loop reactors, or one or more spherical isothermal reactors, and at a temperature in the range of from 120 to 300° C.; for example, from 130 or 135 or 140 or 145 or 150 or 155 or 160° C. to 150 or 155 or 165 or 170 or 175 or 180 or 185 or 190 or 195 or 200 or 205 or 210 or 215 or 220° C.; and at pressures in the range of from 300 to 1500 psi; for example, from 400 to 750 psi. The solution phase polymerization process also occurs in one or more well-stirred reactors, such as one or more loop reactors, or one or more spherical isothermal reactors, and with a reactor ethylene exit concentration in the range of from 18 g/L to 1 g/L; for example, from 18 or 16 or 14 or 12 or 10 or 8 or 6 g/L to 11 or 9 or 7 or 5 or 3 or 1 g/L. The residence time in solution phase polymerization process is typically in the range of from 2 to 30 minutes; for example, from 10 to 20 minutes. Ethylene, one or more solvents, one or more catalyst systems, e.g., an inventive catalyst system, optionally one or more cocatalysts, and optionally one or more comonomers are fed continuously to the one or more reactors. Exemplary solvents include, but are not limited to, isoparaffins. For example, such solvents are commercially available under the name ISOPAR E from ExxonMobil Chemical Co., Houston, Tex. The resultant mixture of the ethylene based polymer and solvent is then removed from the reactor, and the ethylene based polymer is isolated. Solvent is typically recovered via a solvent recovery unit, i.e., heat exchangers and vapor liquid separator drum, and is then recycled back into the polymerization system.

In one embodiment, the ethylene based polymer may be produced, via solution polymerization, in a dual reactor system, for example a dual loop reactor system, wherein ethylene and optionally one or more a-olefins are polymerized in the presence of the inventive catalyst system, as described herein, and optionally one or more cocatalysts. In one embodiment, the ethylene based polymer may be produced, via solution polymerization, in a dual reactor system, for example a dual loop reactor system, wherein ethylene and optionally one or more α-olefins are polymerized in the presence of the inventive catalyst system, as described herein, and optionally one or more other catalysts. The inventive catalyst system, as described herein, can be used in the first reactor, or second reactor, optionally in combination with one or more other catalysts. In one embodiment, the ethylene based polymer may be produced, via solution polymerization, in a dual reactor system, for example a dual loop reactor system, wherein ethylene and optionally one or more α-olefins are polymerized in the presence of the inventive catalyst system, as described herein, in both reactors.

In another embodiment, the ethylene based polymer may be produced, via solution polymerization, in a single reactor system, for example a single loop reactor system, wherein ethylene and optionally one or more α-olefins are polymerized in the presence of the inventive catalyst system, as described herein, and optionally one or more cocatalysts.

In another embodiment, the ethylene based polymer may be produced, via solution polymerization, in a single reactor system, for example a single loop reactor system, wherein ethylene and optionally one or more α-olefins are polymerized in the presence of the inventive catalyst system, as described herein, optionally one or more other catalysts, and optionally one or more cocatalysts.

The procatalyst comprising the metal-ligand complex of Formula (I) may be activated to form an active catalyst composition by combination with one or more cocatalysts, as described above, for example, a cation forming cocatalyst, a strong Lewis acid, or a combination thereof. Suitable cocatalysts for use include polymeric or oligomeric aluminoxanes, especially methyl aluminoxane, as well as inert, compatible, noncoordinating, ion forming compounds. Exemplary suitable cocatalysts include, but are not limited to modified methyl aluminoxane (MMAO), bis(hydrogenated tallow alkyl)methyl, tetrakis(pentafluorophenyl)borate(1−) amine), triethyl aluminum (TEA), and combinations thereof.

In another embodiment, the inventive ethylene based polymers, for example homopolymers and/or interpolymers (including copolymers) of ethylene, and optionally one or more comonomers, such as α-olefins, may be produced, via solution polymerization, in a dual reactor system, for example a dual loop reactor system, wherein ethylene and optionally one or more α-olefins are polymerized in the presence of one or more catalyst systems.

In another embodiment, the inventive ethylene based polymers, for example homopolymers and/or interpolymers (including copolymers) of ethylene, and optionally one or more comonomers, such as α-olefins, may be produced, via solution polymerization, in a single reactor system, for example a single loop reactor system, wherein ethylene and optionally one or more α-olefins are polymerized in the presence of one or more catalyst systems.

The inventive ethylene based polymers, for example homopolymers and/or interpolymers (including copolymers) of ethylene, and optionally one or more comonomers, such as α-olefins, may further comprise one or more additives. Such additives include, but are not limited to, antistatic agents, color enhancers, dyes, lubricants, pigments, primary antioxidants, secondary antioxidants, processing aids, UV stabilizers, and combinations thereof. The inventive ethylene based polymers may contain any amounts of additives. The inventive ethylene based polymers may comprise from about 0 to about 10 percent, further 0.1 to 10 percent, by the combined weight of such additives, based on the weight of the inventive ethylene based polymers and the one or more additives. The inventive ethylene based polymers may further compromise fillers, which may include, but are not limited to, organic or inorganic fillers. Such fillers, e.g. calcium carbonate, talc, $Mg(OH)_2$, can be present in levels from about 0 to about 20 percent, further 1 to 20 percent, based on the weight of the inventive ethylene based polymers and the one or more additives and/or fillers. The inventive ethylene based polymers may further be blended with one or more polymers to form a blend.

EXPERIMENTAL

The following examples illustrate the present invention but are not intended to limit the scope of the invention. Preparation of comparative procatalysts C1 and C3 are described in WO 2007136496 and US 2011/0282018, respectively, incorporated herein by reference to the extent that comparative procatalysts C1 and C3 are taught.
Specific Embodiments for Synthesis of Inventive Catalyst Example 1

1a. Preparation of Ligand 1 (L1)

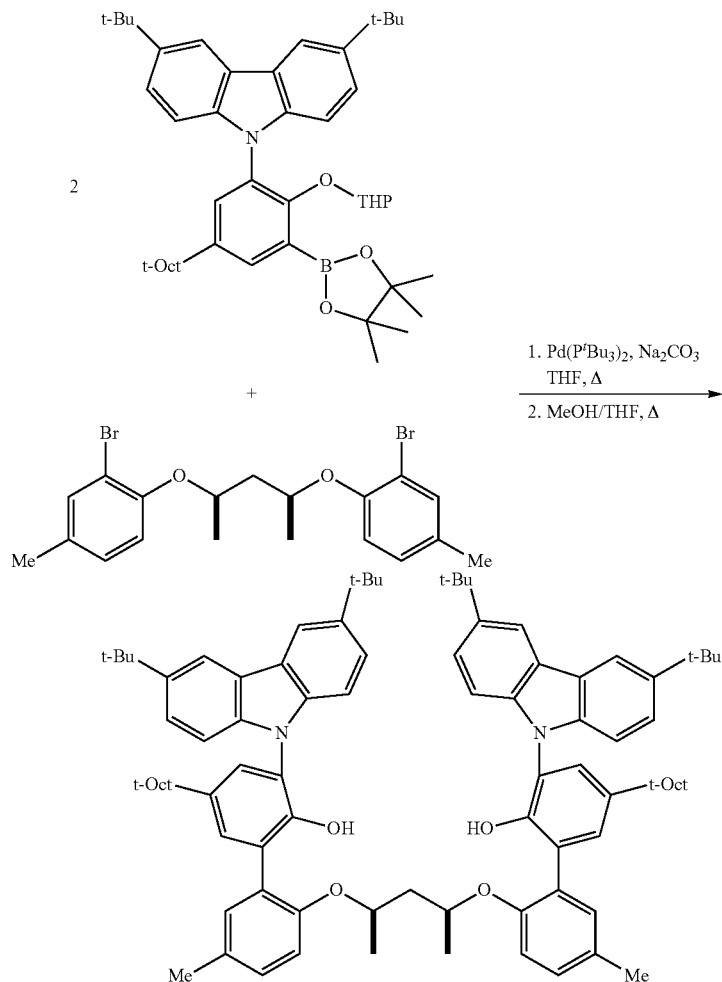

A round bottom flask was charged with 3,6-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (7.285 g, 11.91 mmol) and meso-4,4'-pentane-2,4-diylbis(oxy))bis(3-bromo-1-methylbenzene) (2.194 g, 4.96 mmol), and 60 mL of THF. $Na_2CO_3$ (3.156 g, 29.78 mmol) was dissolved in 30 mL of water, and added to the THF solution, forming a biphasic solution, which was then sparged with $N_2$ for 15 minutes. $Pd(P(t-Bu)_3)_2$ (0.076 g, 0.15 mmol) was dissolved in 20 mL degassed THF, in a nitrogen-filled glovebox, then added to the reaction mixture, which was heated under reflux, under nitrogen for 24 hours. The reaction mixture was allowed to cool to ambient temperature, and then the aqueous phase was separated and discarded. THF was removed from the organic phase on a rotary evaporator, and dichloromethane (120 mL) was added to the residue, and the solution was washed with 120 mL of water. Brine (30 mL) was added to aid phase separation.

The organic phase was collected and evaporated to dryness under vacuum. The residue was dissolved in 50 mL of diethyl ether, filtered through a plug of silica gel and evaporated to dryness under reduced pressure. MeOH (100 mL), THF (40 mL) and concentrated HCl (4 drops) were added to the residue, and the solution was refluxed for two hours. The reaction mixture was allowed cool to room temperature, but no precipitation occurred. Therefore, the solution was concentrated to approximately half its original volume on a rotary evaporator, causing orange-colored solids to form. The solids were filtered, washed with methanol and dried under vacuum (1.83 g). The mother liquor was evaporated to dryness, then the residue was dissolved in diethyl ether (approximately 15 mL), and poured into approximately 200 mL of methanol, causing a small amount of precipitate to form. The volume was decreased by half on under vacuum, causing more solids to crash out. The pale orange solids were filtered, washed with methanol and dried under vacuum, to give pure product (1.90 g). A third crop of product (0.26 g) was recovered from the mother liquor. Overall isolated yield: 3.99 g, 64%. $^1$H NMR (400 MHz, CDCl$_3$) δ 8.16 (t, J=2.1 Hz, 4H), 7.40 (m, 8H), 7.17 (d, J=2.2 Hz, 2H), 7.11 (t, J=8.1 Hz, 4H), 6.88 (dd, J=8.4, 2.2 Hz, 2H), 6.64 (d, J=8.3 Hz, 2H), 6.22 (s, 2H), 4.43 (m, 2H), 2.31 (s, 6H), 2.09 (dt, J=13.8, 6.8 Hz, 1H), 1.75 (s, 4H), 1.64 (dt, J=16.1, 5.9 Hz, 1H), 1.47 (s, 18H), 1.45 (s, 18H), 1.39 (s, 12H), 1.08 (d, J=6.0 Hz, 6H), and 0.82 (s, 18H).

1b. Preparation of Pro-Catalyst 1 (I1)

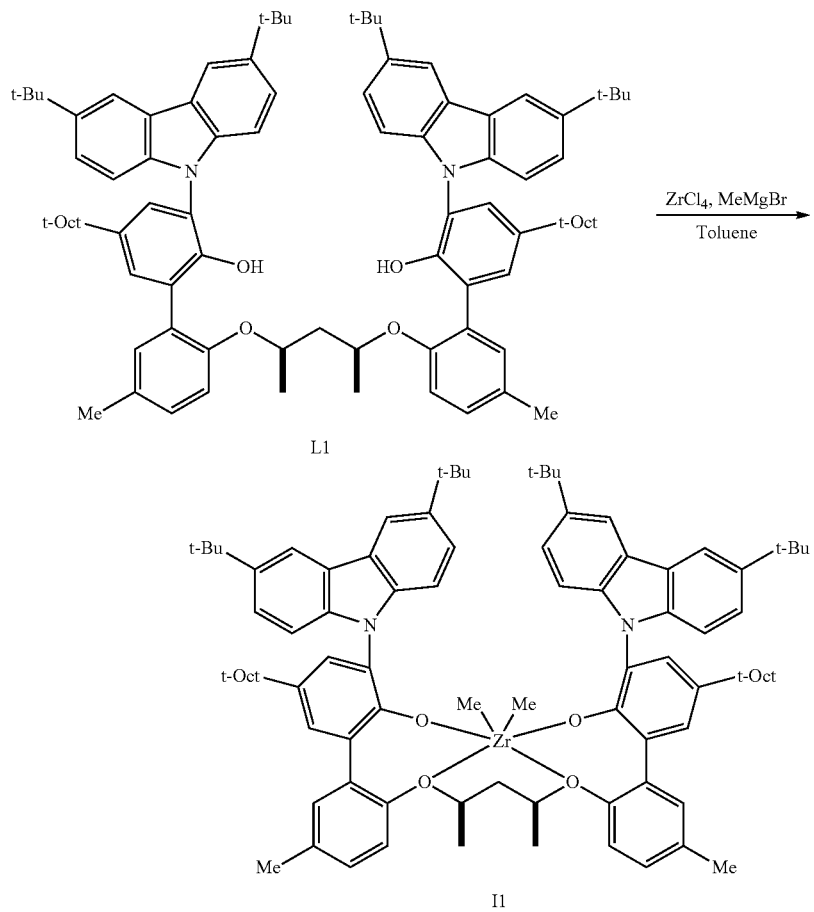

8.45 (d, J=1.7 Hz, 1H), 8.40 (d, J=1.7 Hz, 1H), 7.38-7.85 (m, 16H), 7.13 (d, J=2.2 Hz, 1H), 7.08 (d, J=2.3 Hz, 1H), 6.65 (dd, J=8.4, 2.1 Hz, 1H), 6.62 (dd, J=8.3, 2.1 Hz, 1H), 5.02 (d, J=6.5 Hz, 1H), 4.85 (d, J=6.8 Hz, 1H), 4.33 (dt, J=13.2, 6.8 Hz, 1H), 3.86 (m, 1H), 1.88 (s, 3H), 1.87 (s 3H), 0.79-1.71 (m, 70H), 0.73 (d, J=6.7 Hz, 3H), 0.54 (d, J=6.7 Hz, 3H), −0.70 (s, 3H), and −0.86 (s, 3H). $^{13}$C{$^1$H} NMR (101 MHz, CDCl$_3$) δ 151.4, 147.9, 142.5, 142.2, 139.8, 139.7, 132.7, 131.7, 129.9, 129.0, 128.8, 127.8, 126.6, 125.0, 123.4, 123.2, 116.2, 115.5, 109.5, 73.4, 57.1, 42.4, 38.2, 34.7, 32.4, 32.1, 32.1, 31.9, 31.7, 31.6, 20.6, and 19.7.

The ligand (0.500 g, 0.40 mmol) was dissolved in 10 mL of hexane, under a dry nitrogen atmosphere, and the solution was added to a stirred suspension of ZrCl$_4$ (0.093 g, 0.40 mmol) in 5 mL of hexane. MeMgBr (0.63 mL, 1.64 mmol; 2.6 M in Et$_2$O) was added dropwise, via syringe, at ambient temperature. The mixture was stirred for 14 hours. The color of the reaction mixture slowly turned black. The suspension was filtered, and the filtrate evaporated to dryness under vacuum. Hexane (10 mL) was added to the residue, the light suspension was filtered, and the filtrate evaporated to dryness under vacuum. The treatment with hexane was repeated, and the product was thoroughly dried under vacuum, to afford I1 in good purity as a tan solid (0.193 g, 35%). $^1$H NMR (400 MHz, C$_6$D$_6$): δ 8.69 (t, J=2.0 Hz, 2H),

EXAMPLE 2.

2a. Preparation of meso-4,4'-pentane-2,4-diylbis(oxy)bis(1-(tert-butyl)-3-iodobenzene)

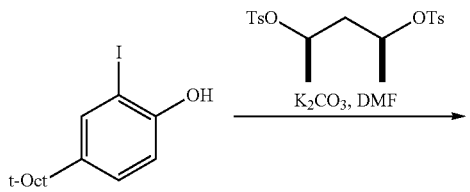

-continued

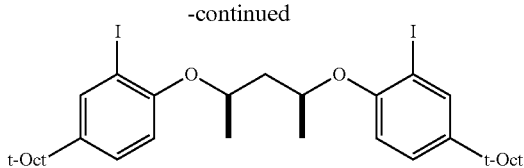

A round-bottom flask was charged with meso-ditosylate (3.1 g, 7.5 mmol), 2-iodo-4-t-octylphenol (5.0 g, 15.1 mmol), and DMF (100 mL). K$_2$CO$_3$ (4.2 g, 30.1 mmol) was added, and the reaction was heated under reflux for one day. The volatiles were then removed by bulb to bulb distillation, yielding a brown solid. The solid was taken up in Et$_2$O (250 mL), rinsed with 3M NaOH solution (2×100 mL), brine (100 mL), and then dried over MgSO$_4$. The reaction mixture was filtered, and concentrated on a rotary evaporator, to yield the crude product, and was further purified by column chromatography (SiO$_2$, hexanes/EtOAc 95:5) to afford the desired product (1.6 g, 29% theoretical 5.5 g). $^1$H NMR (400 MHz, CDCl$_3$) δ 7.74 (d, J=2.3 Hz, 2H), 7.28 (dd, J=8.7, 2.3 Hz, 1H), 6.87 (d, J=8.7 Hz, 2H), 4.77-4.61 (m, 2H), 2.42 (dt, J=13.8, 6.8 Hz, 1H), 1.84 (dt, J=14.0, 5.9 Hz, 1H), 1.68 (s, 4H), 1.36 (d, J=6.1 Hz, 6H), 1.33 (s, 12H), 0.74 (s, 18H). 2d.

2d. Preparation of Ligand 2 (L2).

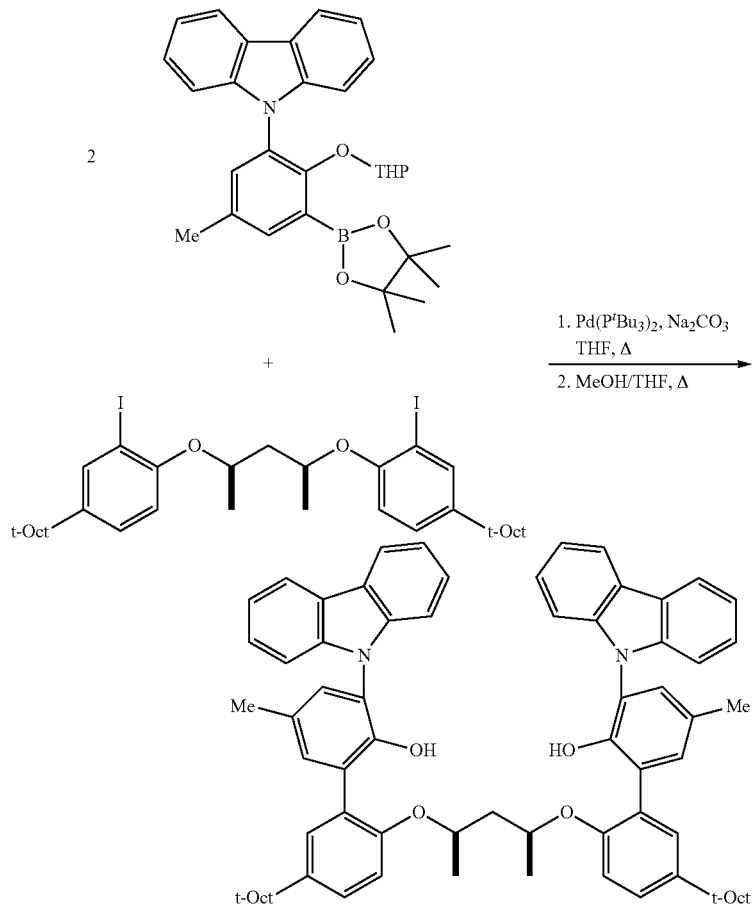

A round bottom flask was charged with meso-4,4'-pentane-2,4-diylbis(oxy))bis(1-(tert-octyl)-3-iodobenzene))

(0.790 g, 1.08 mmol) and 9-(5-methyl-2-((tetrahydro-2H-pyran-2-yl)oxy)-3-(4,4,5,5-tetramethyl-1,3,2-dioxaborolan-2-yl)phenyl)-9H-carbazole (1.052 g, 2.37 mmol), and 40 mL of THF. Na$_2$CO$_3$ (0.686 g, 6.47 mmol) was dissolved in 20 mL of water, and added to the THF solution, forming a biphasic solution, which was then sparged with N$_2$ for 15 minutes. Pd(P(t-Bu)$_3$)$_2$ (0.017 g, 0.03 mmol) was dissolved in 6 mL degassed THF in the drybox, and then added to the reaction mixture, which was heated under reflux, under nitrogen for three days. After allowing the reaction mixture to cool to ambient temperature, the aqueous phase was discarded and THF was removed from the organic phase using a rotary evaporator. Dichloromethane (80 mL) was added, and the solution was washed with 80 mL of water mixed with 20 mL of brine. The organic phase was evaporated to dryness, under vacuum, and the residue was dissolved in 50 mL diethyl ether, filtered through a plug of silica gel, and evaporated to dryness under vacuum. Methanol (80 mL), THF (15 mL) and conc. HCl (6 drops) were added, and the solution was refluxed overnight, and then the solvent was removed, under vacuum, and the residue was triturated with a small amount of methanol, and again dried under vacuum. The resulting material was purified via column chromatography on silica gel, gradient eluting with 1% EtOAc in hexane→5% EtOAc in hexane, furnishing the pure ligand L2 (0.820 g, 74%). $^1$H NMR (400 MHz, CDCl$_3$): δ 8.15 (dd, J=7.5, 1.2 Hz, 4H), 7.40 (d, J=2.5 Hz, 2H), 7.33 (m, 10H), 7.23 (m, 6H), 7.16 (dd, J=8.5, 2.3 Hz, 2H), 6.66 (d, J=8.7 Hz, 2H), 6.23 (s, 2H), 4.52 (m, 2H), 2.47 (s, 6H), 2.22 (m, 1H), 1.74 (s, 4H), 1.71 (m, 1H), 1.38 (d, J=6.1 Hz, 12H), 1.18 (d, J=6.0 Hz, 6H), and 0.75 (s, 18H). $^{13}C\{^{1}H\}$ NMR (101 MHz, CDCl$_3$) δ 151.1, 148.3, 144.0, 141.3, 141.2, 131.7, 130.3, 130.3, 129.2, 129.1, 127.19, 126.8, 125.6, 125.6, 125.2, 123.3, 123.2, 120.2, 120.6, 119.5, 113.8, 110.3, 110.2, 72.7, 57.0, 42.7, 38.1, 32.4, 31.8, 31.5, 20.7, and 19.8.

2d. Preparation of Pro-Catalyst 2 (I2)

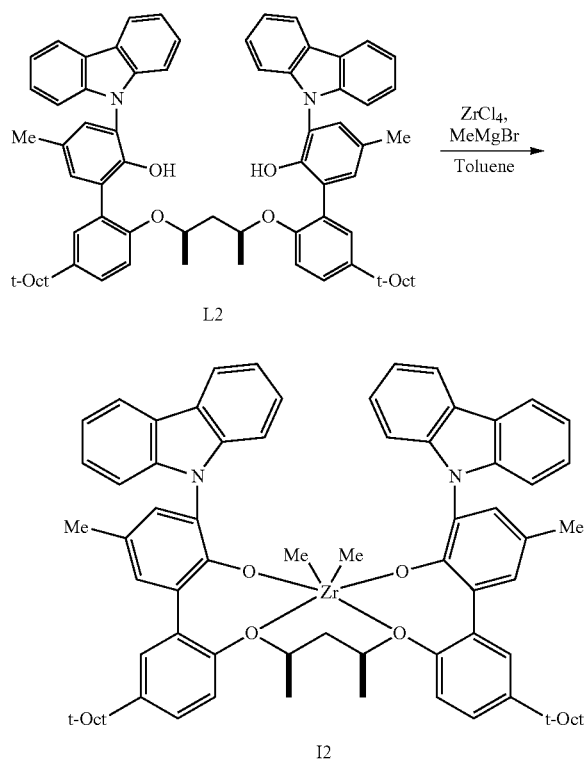

The ligand L4 (0.500 g, 0.49 mmol) was dissolved in 10 mL of toluene, under a dry nitrogen atmosphere, and the solution was added to a stirred suspension of ZrCl$_4$ (0.114 g, 0.490 mmol) in 5 mL of toluene. MeMgBr (0.77 mL, 2.00 mmol; 2.6 M in Et$_2$O) was added, dropwise, via syringe at ambient temperature. The mixture was stirred for two hours. The color of the reaction mixture slowly turned black. Hexane (5 mL) was added to the suspension, which was then filtered, and the filtrate evaporated to dryness under vacuum. Toluene (15 mL) and hexane (5 mL) were added to the residue, the light suspension was filtered, and the filtrate evaporated to dryness under vacuum, furnishing 14 in high purity (292 mg, 52%). $^1$H NMR (400 MHz, C$_6$D$_6$) δ 8.35 (m, 2H), 8.10 (m, 2H), 7.67 (m, 1H), 7.57-7.32 (m, 12H), 7.23-7.08 (m, 5H), 6.84 (ddd, J =10.8, 8.5, 2.5 Hz, 2H), 5.04 (d, J=8.5 Hz, 1H), 4.87 (d, J=8.6 Hz, 1H), 4.04 (m, 1H), 3.68 (m, 1H), 2.22 (s, 6H), 1.76-1.60 (m, 4H), 1.24 (s, 3H), 1.22 (s, 3H), 1.21 (s, 3H), 1.19 (s, 3H), 0.76 (s, 9H), 0.75 (s, 9H), 0.50 (d, J=6.2 Hz, 3H), 0.32 (d, J=6.5 Hz, 3H), −0.77 (s, 3H), and −0.91 (s, 3H).

EXAMPLE 3

3a. Preparation of 3,6-bis(1,1-dimethylethyl)-9H-carbazole

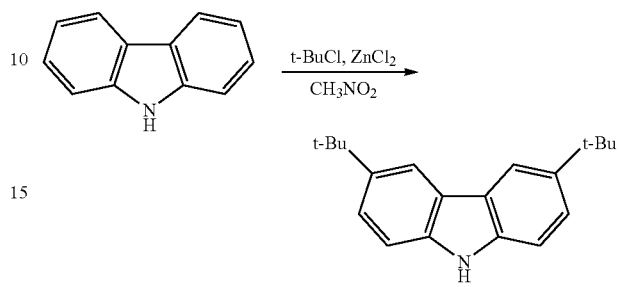

A 500 mL, three-neck, round bottom flask, equipped with an overhead stirrer, nitrogen gas bubbler, and an addition funnel, was charged with 20.02g (120.8 mmol) of carbazole, 49.82g (365.5 mmol) of ZnCl$_2$, and 300 mL of nitromethane at room temperature. To the resulting dark brown slurry, was added, 49.82g (365.5 mmol) of 2-chloro-2-methylpropane (also known as tertiary-butyl chloride), dropwise from the addition funnel, over the period of 2.5 hours. After completing the addition, the resulting slurry was stirred for an additional 18 hours, and the reaction mixture was poured into 800 mL of ice cold water, and extracted with methylene chloride (3×500 mL). The combined extracts were dried with anhydrous magnesium sulfate, filtered, and concentrated, first by rotary evaporation, and then by evaporation under high vacuum to remove nitromethane. The resulting residue was dissolved in hot methylene chloride (70 mL), followed by hot hexanes (50 mL), and the resulting solution was cooled to room temperature, and then placed it in a refrigerator overnight. The resulting solids which formed were isolated, washed with cold hexanes, and then dried under high vacuum to yield 10.80 g (32.0%) of the desired product as off-white crystals. $^1$H NMR (400 MHz, CDCl$_3$) δ 8.11 (d, J=1.6 Hz, 2H), 7.75 (s, 1H), 7.48 (dd, J=8.5, 1.9 Hz, 2H), 7.31 (d, J=8.5 Hz, 2H), 1.48 (s, 18H). $^{13}C\{^{1}H\}$ NMR (101 MHz, CDCl$_3$) δ 142.17 (s), 137.96 (s), 123.45 (s), 123.28 (s), 116.11 (s), 109.97 (s), 34.73 (s), 32.09 (s).

3b. Preparation of 2-iodo-4-(2,4,4-trimethylpentan-2-yl)phenol

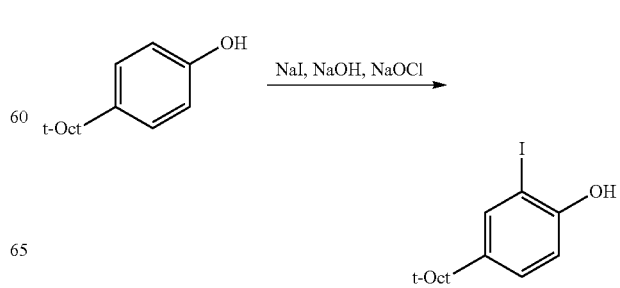

To a stirred solution of 10.30 g (50.00 mmol) of 4-(2,4,4-trimethylpentan-2-yl)phenol, in 125 mL of methanol at 0° C., was added 7.48 g (50.00 mmol) of NaI and 2.00 g (50.0 mmol) of NaOH. To the resulting mixture, was added, 86 mL of 5% aqueous NaOCl solution (commercial bleach) over a one hour period. The resulting slurry was stirred for one more hour at 0° C., then 30 mL of aqueous 10% $Na_2S_2O_3$ solution was added, and the resulting reaction mixture was acidified with the addition of dilute hydrochloric acid. The resulting mixture was extracted with methylene chloride, and the resulting organic layer was washed with brine, and then dried over anhydrous magnesium sulfate. The volatiles were removed under vacuum, and the resulting residue was purified by flash chromatography on silica gel, eluting with 5 volume percent (vol %) ethyl acetate in hexanes to yield 11.00 g (66%) of the desired product as a viscous oil. $^1$H NMR (CDCl$_3$) δ 7.60 (d, J=2.5 Hz, 1H), 7.25 (dd, J=8.5 and 2.2 Hz, 1H), 6.90 (d, J=8.5 Hz, 1H), 5.13 (s, 1H), 1.69 (s, 2H), 1.32 (s, 6H) and 0.74 (s, 9H). $^{13}$C{$^1$H} NMR (CDCl$_3$) δ 152.21, 144.52, 135.56, 128.03, 114.17, 85.36, 56.92, 38.01, 32.43, 31.90 and 31.64. GC/MS (m/e): 332 (M$^+$).

3c. Preparation of 2-(2-iodo-4-(2,4,4-trimethylpentan-2-yl)phenoxy)tetrahydro-2H-pyran

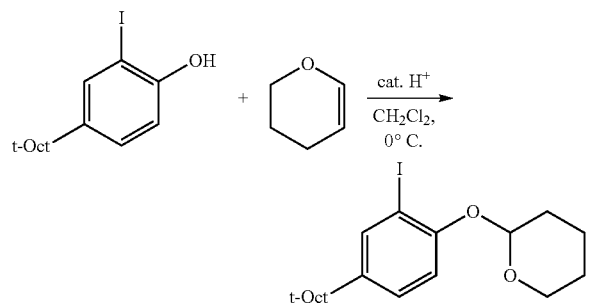

To a stirred solution of 4.91 g (14.8 mmol) of 4-(2,4,4-trimethylpentan-2-yl)phenol and 1.50 g (17.8 mmol) of 3,4-dihydropyran, in 5 mL of methylene chloride, at 0° C., was added, 0.039g (0.205 mmol) of para-toluenesulfonic acid monohydrate. The resulting solution was allowed to warm to room temperature, and stirred thereat for approximately 10 minutes. Then triethylamine (0.018 g, 0.178 mmol) was added, and the resulting mixture was diluted with 50 mL of methylene chloride, and successively washed with 50 mL each of 1M NaOH, water, and brine. The organic phase was dried with anhydrous magnesium sulfate, filtered, and concentrated, to give a crude material, which was purified by flash chromatography on silica gel, using 5 vol % ethyl acetate in hexanes, to yield 5.18 g (93.12%) of the desired product as a golden oil. $^1$H NMR (CDCl$_3$) δ 7.74 (d, J=2.3 Hz, 1H), 7.27 (dd, J=2.3 and 8.6 Hz, 1H), 6.99 (d, J=8.6 Hz, 1H), 5.49 (m, 1H), 3.91 (m, 1H), 3.61 (m,1H), 2.20-1.60 (m, 6H), 1.69 (s, 2H), 1.34 (s, 6H) and 0.75 (s, 9H). $^{13}$C{$^1$H} NMR (CDCl$_3$) δ 153.27, 145.49, 136.98, 127.08, 114.44, 96.72, 87.09, 61.69, 56.91, 37.95, 32.33, 31.81, 31.52, 31.44, 30.26, 25.27, 18.36.

3d. Preparation of 3,6-di-tert-butyl-9-(2-(tetrahydro-2H-pyran-2-yloxy)-5-(2,4,4-trimethyl-pentan-2-yl)phenyl)-9H-carbazole.

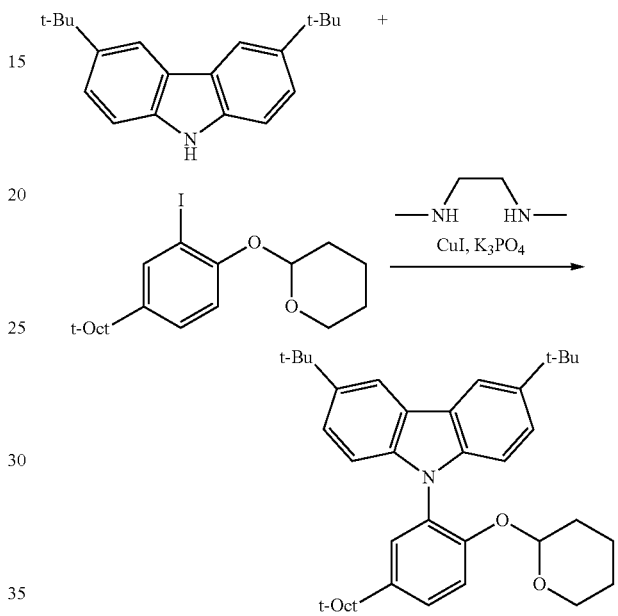

To a 50 mL, three necked, round bottom flask, equipped with a stir bar and condenser, under N$_2$ atmosphere, was added the following: 20 mL of dry toluene, 5.00 g (12.01 mmol) of 2-(2-iodo-4-(2,4,4-trimethylpentan-2-yl)phenoxy)tetrahydro-2H-pyran; 3.56 g (12.01 mmol) of 3,6-di-tert-butyl carbazole, 0.488g (2.56 mmol) of CuI, 7.71 g (36.2 mmol) of K$_3$PO$_4$, and 0.338 g (3.84 mmol) of N,N'-dimethylethylenediamine. The resulting reaction mixture was heated, under reflux, for 48 hours, cooled, and filtered through a bed of silica gel. The silica gel was rinsed with tetrahydrofuran (THF), and the resulting solution was concentrated to give a crude residue. Purification was accomplished by recrystallization from acetonitrile, to yield 4.57 g (67.0%) of the desired product as a white solid. $^1$H NMR (CDCl$_3$) δ 8.13 (t, J=1.71 Hz, 1H), 7.48 (d, J=2.4 Hz, 1H), 7.40 (m, 3H), 7.31 (d, J=8.68 Hz, 1H), 7.14 (d, J=8.68 Hz, 1H), 7.08 (d, J=8.56 Hz, 1H), 5.22 (t, J=2.81 Hz, 1H), 3.72(td, J=11.12 and 2.8 Hz, 1H), 3.47 (dt, J=11.12 and 3.47 Hz, 1H), 1.75 (s, 2H), 1.474 (s, 9H), 1.472 (s, 9H), 1.394 (s, 3H), 1.391 (s, 3H), 1.37-1.12 (m, 6H), 0.82 (s, 9H). $^{13}$C{$^1$H} NMR (CDCl$_3$) δ 150.96, 144.22, 142.07, 140.02, 127.49, 126.60, 126.56, 123.14, 123.12, 122.96, 116.37, 115.88, 115.72, 110.18, 109.52, 97.02, 61.56, 57.03, 38.23, 34.69, 32.41, 32.07, 31.86, 31.72, 31.50, 29.98, 25.06, 17.61.

3e. Preparation of 3,6-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole

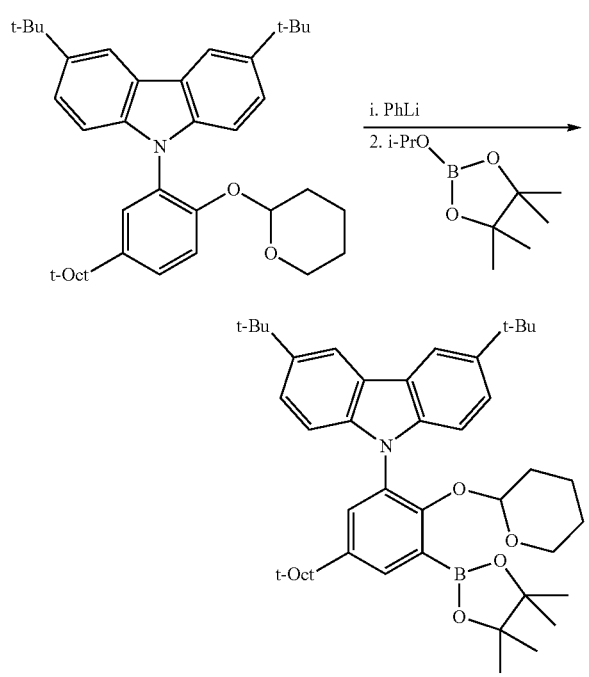

To a stirred solution of 2.5 g (4.4 mmol) of carbazole derivative, in 40 mL of THF, at 0° C., under nitrogen atmosphere, 2.8 mL (7.0 mmol) of n-butyl lithium (2.5 M solution in hexanes) was added, over a period of five minutes. The solution was stirred at 0° C. for three more hours. 2-Isopropoxy-4,4,5,5-tetramethyl-1,3,2-dioxaborolane (1.44 mL, 7.0 mmol) was added to this, and the stirring continued at 0° C. for one more hour. The reaction mixture was slowly warmed to room temperature, and stirred for 18 hrs. The reaction mixture was concentrated to dryness and by rotary evaporation, and 100 mL of ice cold water was added. The mixture was extracted with methylene chloride. The organic layer was washed with brine, and dried over anhydrous magnesium sulfate. Removal of the solvent, followed by recrystallization from acetonitrile, gave 2.4 g (78.6%) of titled product as white solid. $^1$H NMR (CDCl$_3$) δ 8.30-7.96 (m, 2H), 7.81(d, J=2.5 Hz, 1H), 7.58-7.32 (m, 3H), 7.14 (d, J=8.6 Hz, 2H), 4.85 (d, J=2.8 Hz, 1H), 2.76 (td, J=11.0, 2.7 Hz, 1H), 2.59 (dd, J=7.9, 3.5 Hz, 1H), 1.73 (s, 2H), 1.67-0.87 (m, 6H), 1.46 (s, 9H), 1.45 (s, 9H), 1.38 (s, 9H), 1.37 (s, 9H), 0.78 (s, 9H); $^{13}$C{$^1$H} NMR (CDCl$_3$) δ 156.25, 145.86, 142.05, 142.01, 139.79, 139.78, 133.82, 130.61, 129.72, 123.39, 123.37, 123.05, 115.59, 115.55, 110.20, 110.11, 101.41, 83.64, 61.20, 56.95, 38.37, 34.68, 32.42, 32.08, 31.90, 31.45, 29.97, 25.06, 25.04, 24.79, 18.16. MS m/e 716.38 (M+Na).

3f. Preparation of meso-4,4'-pentane-2,4-diylbis(oxy))bis(3-bromo-1-fluorobenzene)

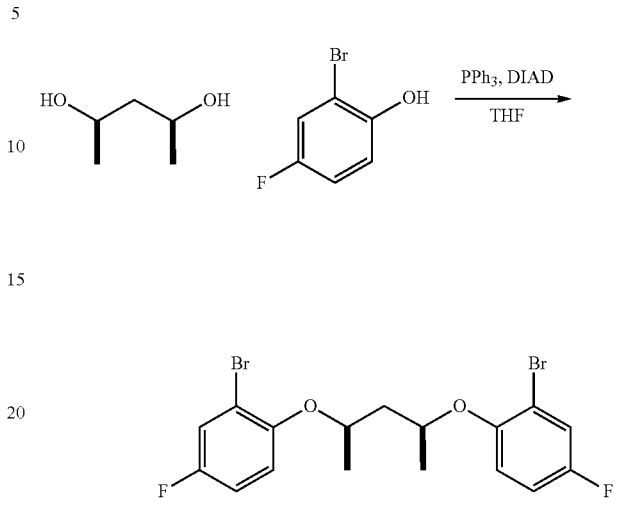

A 2-L, three-neck, round bottom flask, equipped with a thermometer, a magnetic stirrer, an addition funnel, and a nitrogen pad, was charged with 2,4-pentanediol (30.46 g, 292.5 mmol, 1 equiv), 2-bromo-4-fluorophenol (114.39 g, 598.9 mmol, 2.04 equiv), triphenylphosphine (157.12 g, 599.0 mmol, 2.04 equiv), and THF (600 mL), and the contents cooled to 2° C. in an ice-water bath. A solution of DIAD (121.11 g, 598.9 mmol, 2.04 equiv) in THF (130 mL), in the addition funnel, was added, at such a rate, to maintain the reaction below 5° C. (the addition took approximately four hours). The resulting mixture was stirred at 2- ° C. for an additional one hour, and a sample was taken for GC-MS analysis, which indicated the reaction was near to completion. After stirring overnight, at ambient temperature, volatiles were removed under reduced pressure. Cyclohexane (700 mL) was added to the residue and the slurry was stirred at room temperature for 30 minutes. The insoluble solid was filtered, rinsed with cyclohexane (100 mL x3). The cyclohexane solution was washed with 1N NaOH (200 mL), water (200 mL), 1N HCl (200 mL), water (500 mL x2), and then concentrated, under reduced pressure, to give an oil residue. The oil residue was dissolved in hexane (100 mL), and then passed through a pad of silica gel (315 g), eluting with hexane (300 mL), and hexane-EtOAc (20:1 in volume, hexane 2 L+EtOAc 100 mL), concentrated ,and dried, to give the desired bottom group (123.8 grams, 94% yield). $^1$H NMR (400 MHz, C$_6$D$_6$) δ 7.14 (dd, J=8.4, 3.9 Hz, 2H), 6.64 (dt, J=9.1, 3.9 Hz, 2H), 6.48 (dd, J=9.0, 3.7 Hz, 2H), 4.22 (m, 2H), 2.17 (dt, J=13.6, 6.5 Hz, 1H), 1.45 (dt, J=13.6, 5.6 Hz, 1H), and 0.98 (d, J=6.1 Hz, 6H). $^{13}$C NMR (101 MHz, CDCl$_3$) δ 156.9 (d, J=235.8 Hz), 150.9 (d, J=2.8 Hz), 120.9 (d, J=25.8 Hz), 115.62 (d, J=7.7 Hz), 114.9 (d, J=21.5 Hz), 113.7 (d, J=10.1 Hz), 72.8, 42.7, and 19.6. $^{19}$F NMR (376 MHz, C$_6$D$_6$) δ-121.33.

3g. Preparation of Ligand 3 (L3)

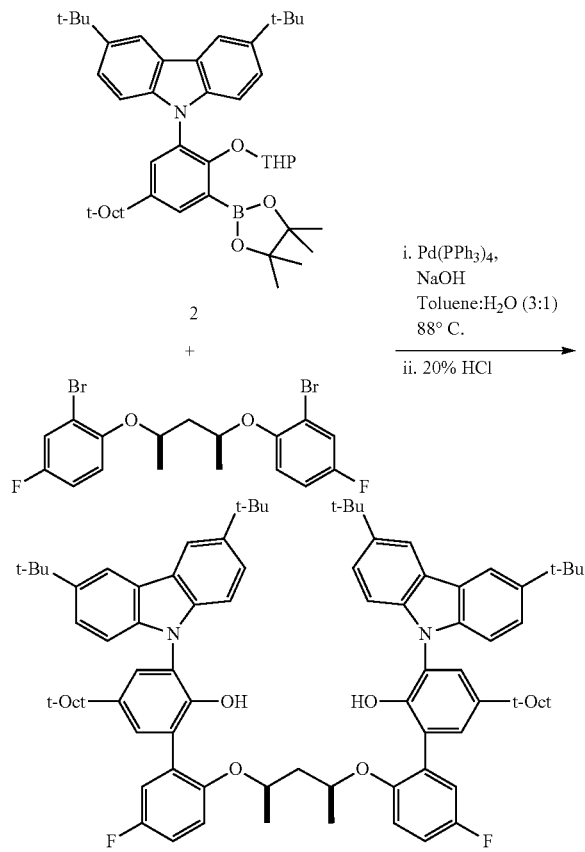

Method 1: To a 2 reactor vessel, was added, meso-4,4'-pentane-2,4-diylbis(oxy))bis(3-bromo-1-fluorobenzene) (80 g, 177.7 mmol) and 3,6-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (271.3 g, 391.0 mmol), dissolved in 800 mL of toluene, under a nitrogen atmosphere, with stirring. To this, was added, NaOH (42.7g dissolved in 100 mL of water, 1.0 mol), followed by quick addition of Pd(PPh$_3$)$_4$ (8.21 g, 7.11 mmol), and the reaction heated to 88° C. The course of the reaction was monitored via LC, until deemed complete at the five hour mark. At this point, the reaction vessel was cooled to rt (room temperature), the caustic layer removed, and 200 mL of a 20% HCl solution was added, and the reaction heated once more to 88° C. for five hours. The reactor was cooled to ambient temperature, the aqueous layer removed, and the organic layer washed with brine, and dried over MgSO$_4$. Filtration to remove the MgSO$_4$, followed by concentration via rotary evaporation, gave an off-white solid, which was washed with acetonitrile, and the remaining solid dried under vacuum to provide pure DOC-6163 ligand (199.5 grams, 89% yield).

Method 2 (Two Step Procedure)

Ph$_3$P (1.05 g, 4 mmol), meso-4,4'-pentane-2,4-diylbis(oxy))bis(3-bromo-1-fluorobenzene) (45.01 g, 100.0 mmol), aliquot 336 (0.326 g) and toluene (500 mL) were added into a 2L, three-neck, round bottom flask, equipped with cold water condenser, magnetic stirrer, a thermometer, and a nitrogen pad in an oil bath. The mixture was sparged with nitrogen for 30 minutes. Pd(OAc)$_2$ (449.02 mg, 2.0 mmol, 0.02 equiv) was added, and the mixture was stirred for 5-10 minutes, until solid Pd(OAc)$_2$ dissolved, while sparging with nitrogen. Then 2N NaOH (300 mL, pre-sparged with nitrogen) was added, under nitrogen, and the mixture was sparged with nitrogen for five minutes. The reaction mixture was heated to 75-78° C., and a solution of 3,6-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (156.64 g, 220 mmol) in 400 mL of toluene (sparged with nitrogen for 30 min) was added, over three hours, via a syringe pump. The reaction mixture was heated at 80-86° C. overnight (the reaction was complete over 4-6 hours, as monitored by LC), under nitrogen atmosphere, in a 105° C. oil bath, which resulted in a dark mixture. After being cooled to 50° C., air was bubbled into the reaction mixture for one hour to destroy the catalyst. The reaction mixture was then settled for phase-cut. The bottom aqueous layer was removed, and extracted with toluene (100 mL). The toluene phase was washed with water (500 mL ×2). 2N HCl (300 mL, prepared from 100 mL 6N HCl +200 mL H$_2$O) was added to the toluene solution. The resulting mixture was stirred 80-86° C., in a 105-108° C. oil bath, under nitrogen overnight. LC analysis of the reaction mixture indicated that the deprotection of the THP group was complete. The reaction mixture was allowed to cool to ambient temperature. The bottom aqueous layer was removed, which was subsequently extracted with toluene (100 mL). The yellow to brown toluene phase was washed with water (500 mL ×2). The toluene solution was filtered through a pad of silica gel (60-100 g). The silica gel wet cake was rinsed with toluene (100 mL). The slightly yellow toluene solution was concentrated, under reduced pressure, by rotovap, which gave a thick residue (~185.5 g). Acetonitrile (500 mL) was added to the residue, and the mixture was spun on roto-vap at 60° C. The thick residue was gradually dissolved, forming a clear, slightly yellow solution. White solid precipitated out from the solution after a while. After cooling to ambient temperature overnight, the solid was collected by filtration, washed/rinsed with acetonitrile (200 mL ×2), suck-dried, and dried in vacuum oven, to give the desired product (115.5 grams, 92.0% yield). $^1$H NMR (400 MHz, C$_6$D$_6$) δ 8.45 (t, J=2.4 Hz, 4H), 7.50-7.56 (m, 6H), 7.41 (d, J=8.8 Hz, 2H), 7.16 (obscured by CD$_5$H), 6.32 (s, 2H), 6.30 (dd, J=9.3, 4.7 Hz, 2H), 6.23 (s, 2H), 4.16 (m, 2H), 2.01 (dt, J=14.3, 6.9 Hz, 1H), 1.55 (s, 4H), 1.37 (dt, J=14.2, 5.0 Hz, 1H), 1.44 (s, 18H), 1.43 (s, 18H), 1.20 (s, 12H), 0.83 (d, J=6.0 Hz, 6H), and 0.80 (s, 18H). $^{13}$C{$^1$H} NMR (101 MHz, C$_6$D$_6$) δ 158.2 (d, J=241.2 Hz), 149.8 (d, J=1.7 Hz), 148.9, 143.2, 143.0, 143.0, 140.7 (d, J=5.5 Hz), 131.1 (d, J=7.5 Hz), 129.4, 127.2, 126.1, 124.2 (d, J=2.7 Hz), 118.9 (d, J=23.4 Hz), 117.3 (d, J=9.2 Hz), 116.8, 115.8 (d, J=22.8 Hz), 110.2 (d, J=10.0 Hz), 73.7, 57.1, 42.66, 38.3, 34.9, 32.5, 32.2, 32.1, 31.7, 31.6, and 19.5. $^{19}$F NMR (376 MHz, C$_6$D$_6$) δ −120.95.

3g. Preparation of Pro-Catalyst 3 (I3)

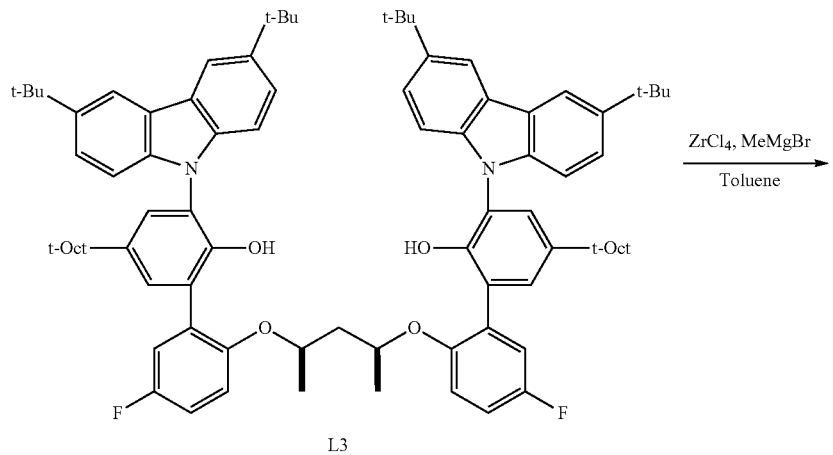

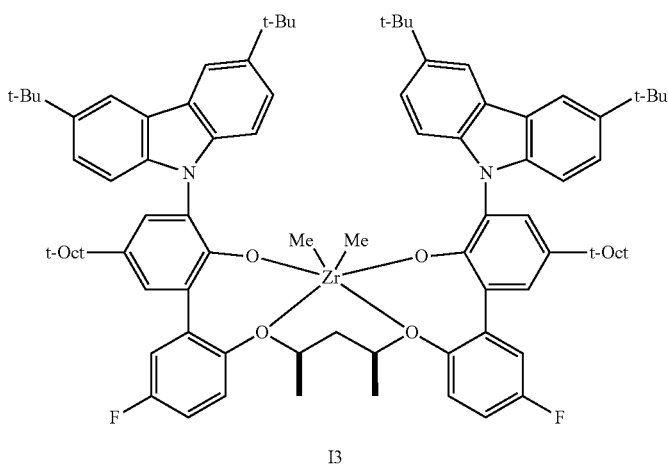

A 5 reactor was charged with 4.5 of toluene, and cooled to −30° C. To this, was added, ZrCl₄ (38.8 1 g, 166.8 mmol), followed by MeMgBr (211.8 mL of a 3M solution, 635.5 mmol). The resulting mixture was allowed to stir for five minutes, after which, the ligand L3 (199.5 g, 158.9 mmol) was added. The suspension was allowed to gradually warm to room temperature, and was stirred for an additional three hours, and then filtered. The toluene was then removed, under vacuum, to provide I3, as an off white solid in good purity (quantitative, 234 grams). $^1$H NMR (400 MHz, C$_6$D$_6$) δ 8.53 (m, 2H), 8.41 (dd, J=2.0, 12.0 Hz, 2H), 7.72 (m, 2H), 7.67 (d, J=3.0 Hz, 1H), 7.57-7.61 (m, 6H), 7.44 (ddd, J=2.9, 8.1, 9.4 Hz, 2H), 7.24 (dd, J=2.0, 14 Hz, 2H), 7.01 (dd, J=3.7, 8.9 Hz, 2H), 6.95 (dd, 4.0, 7.3 Hz, 1H), 6.60 (m, 2H), 4.95 (dd, J=4.4, 8.2 Hz, 2H), 4.82 (dd, J=4.4, 8.2 Hz, 2H), 4.21 (m, 2H), 3.78 (m, 2H), 1.64 (s, 3H), 1.58 (s, 3H), 1.48 (s, 9H), 1.46 (s, 9H), 1.32 (s, 9H), 1.30 (s, 9H), 0.77-0.90 (m, 8H), 1.20-1.28 (m, 8H), 0.60 (d, J=7.3 Hz, 3H), 0.41 (d, J=7.3 Hz, 3H), −0.72 (s, 3H), and −0.88 (s, 3H). $^{19}$F NMR (376 MHz, C$_6$D$_6$) δ −114.83.

EXAMPLE 4

4a. Preparation of 2-bromo-1-(methoxymethoxy)-4-methylbenzene.

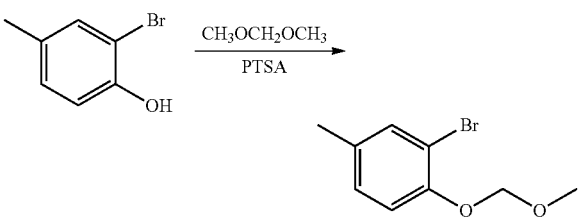

2-Bromo-4-methylphenol (13.1 g, 70.0 mmol), dimethoxymethane (35 mL), p-toluene-sulfonic acid (100 mg) and methylene chloride (300 mL) were heated, under reflux, in a nitrogen atmosphere for three days, using a Soxhlet condenser containing activated 3Å molecular sieves. The molecular sieves were exchanged for newly activated ones after every 24 hours. The reaction mixture was cooled, and the volatiles were removed by rotary evaporation. The residue was taken up in 100 mL of ether, and washed successively with 100 mL of 2M sodium hydroxide solution, 100 mL of water and 100 mL of brine. The organic layer was dried over anhydrous magnesium sulfate and passed through a small bed of silica gel. Removal of the solvent gave 14.5 g (92%) of pure 2, as a pale yellow oil, which was used as such for the next step. $^1$H NMR (CDCl$_3$) δ 7.40 (m, 1H), 7.07 (m, 2H), 5.25 (s, 2H), 3.55 (s, 3H) and 2.31 (s, 3H).

4c. Preparation of 9-(5-methyl-2-((tetrahydro-2H-pyran-2-yl)oxy)-3-(4,4,5,5-tetramethyl-1,3,2-dioxaborolan-2-yl)phenyl)-9H-carbazole

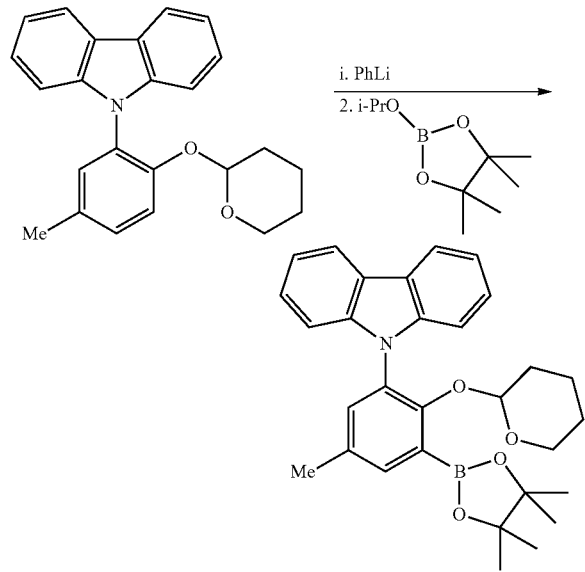

9-(5-methyl-2-((tetrahydro-2H-pyran-2-yl)oxy)phenyl)-9H-carbazole (40 g, 0.11 mol) was dissolved in 300 mL of THF, in a nitrogen-filled glovebox, and deprotonated by the slow addition of PhLi (74.6 mL, 0.13 mol; 1.8 M in n-Bu$_2$O). The reaction mixture was stirred for one hour. 2-Isopro-poxy-4,4,5,5-tetramethyl-1,3,2-dioxaborolane (25.1 mL, 0.12 mol) was added slowly, and the reaction mixture was stirred for another hour. Solvent removal, under vacuum, gave an oily residue, which was dissolved in 450 mL of chloroform, and washed with water (2×450 mL). The organic layer was dried over MgSO$_4$, filtered, and the filtrate concentrated, under vacuum, to afford a dark oil, which was then mixed with 600 mL hexane, and concentrated to approximately 250 mL, causing a large amount of light brown solids to form. The solids were filtered and dried under vacuum (42 g, 78%). $^1$H NMR (400 MHz, CDCl$_3$) δ 7.99 (m, 2H), 7.59 (d, J=2.3 Hz, 1H), 7.28 (ddd, J=15.4, 8.2, 1.1 Hz, 2H), 7.14 (m, 5H), 4.78 (t, J=3.0 Hz, 1H), 2.44 (m, 2H), 2.25 (s, 3H), 1.59 (m, 1H), 1.28 (s, 6H), 1.27 (s, 6H), 1.09 (m, 4H), 0.82 (m, 1H).

4d. Preparation of meso-4,4'-pentane-2,4-diylbis(oxy))bis(3-bromo-1-methylbenzene)

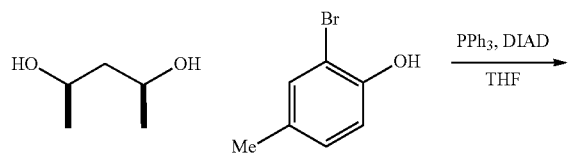

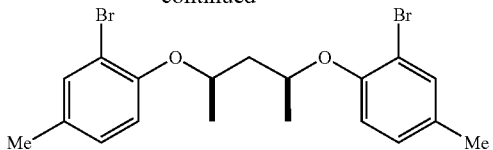

A 2-L, three-neck, round bottom flask, equipped with a thermometer, a magnetic stirrer, and an addition funnel, was charged with meso-2,4-pentanediol, (30.50 g, 293 mmol), 2-bromo-4-methylphenol (112.03 g, 599 mmol), triphenylphosphine (157.12 g, 599 mmol), and THF (600 mL). The reaction vessel was then placed under a nitrogen atmosphere, and the addition funnel was charged with diisopropyl azodicarboxylate (DIAD, 121.11 g, 599 mmol) and THF (250 mL). The contents in the flask were cooled to 2° C. in an ice-water bath, the DIAD solution, in the addition funnel, was added, at such a rate, to maintain the reaction temperature at 2-5° C. (the addition took approximately 3.5 h). The resulting mixture was stirred at 2-5° C. for an additional one hour (a sample was taken for GC-MS analysis, which showed the reaction was near to completion), and then allowed to warm up to ambient temperature overnight. The volatiles were removed, under reduced pressure, to give a solid residue (~424 g). The residue was extracted with cyclohexane (1000 mL), at 35° C., by spinning on a rotary-evaporator for 30 minutes, without pulling vacuum. This process was repeated for additional three times with cyclohexane (350 mL ×3) at 35° C. The combined cyclohexane solution was washed with 1N NaOH (350 mL ×2), water (500 mL), 1N HCl (350 mL), and water (500 mL ×2). The washed cyclohexane solution was concentrated to approximately 300 mL, passed through a pad of silica gel (350 g), and eluted with hexane/ EtOAc (20:1 in volume), concentrated, and dried, to give the desired bottom group (119.0 grams, 91.5%). $^1$H NMR (400 MHz, CDCl$_3$) δ 7.26 (d, J=2.3 Hz, 2H), 7.04 (dd, J=8.5, 2.3 Hz, 2H), 6.94 (d, J=8.5 Hz, 2H), 4.63 (m, 2H), 2.39 (dt, J=13.8, 6.7 Hz, 1H), 2.26 (s, 6H), 1.82 (dt, J=14.1, 5.9 Hz, 1H), and 1.37 (d, J=6.1 Hz, 6H). $^{13}$C{$^1$H} NMR (101 MHz, CDCl$_3$) δ 152.1, 133.9, 131.8, 115.2, 114.77, 112.9, 72.5, 42.9, 20.3, and 20.0.

4e. Preparation of Ligand 4 (L4)

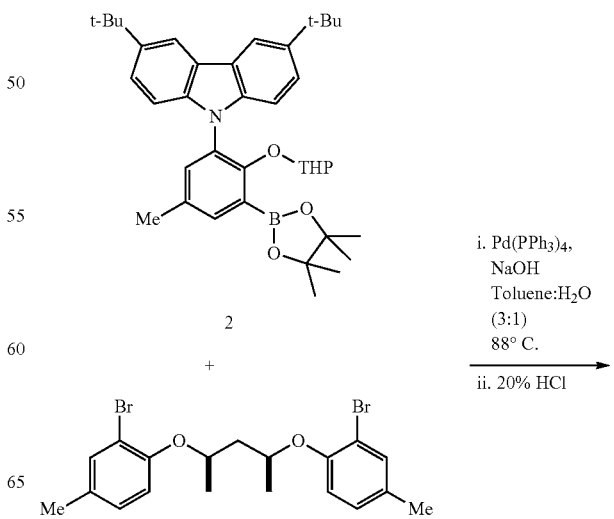

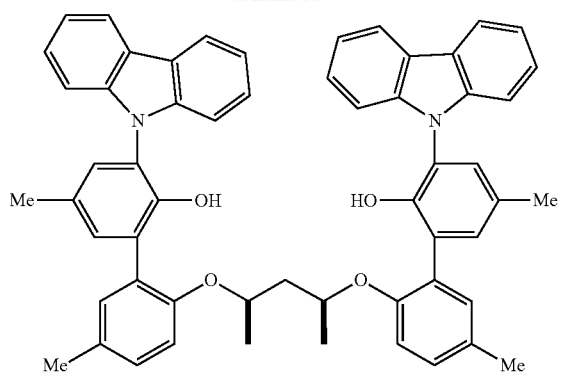
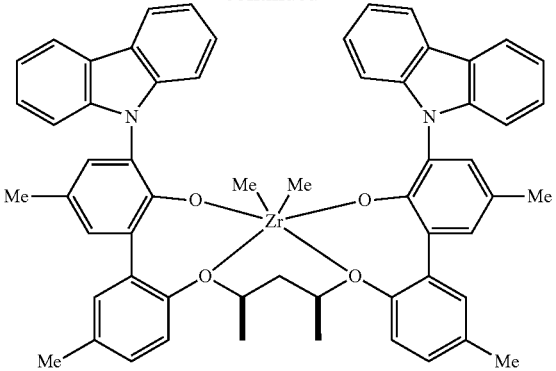

To a 2-L reactor vessel, was added, meso-4,4'-pentane-2,4-diylbis(oxy))bis(3-bromo-1-methyl-benzene) (40.0 g, 90.5 mmol) and 9-(5-methyl-2-((tetrahydro-2H-pyran-2-yl)oxy)-3-(4,4,5,5-tetramethyl-1,3,2-dioxaborolan-2-yl)phenyl)-9H-carbazole (96.2 g, 199.0 mmol, 2.2 equiv), dissolved in 300 mL of toluene, under a nitrogen atmosphere, with stirring. To this, was added, NaOH (21.7 g dissolved in 100 mL of water, 0.5 mol, 6 equiv), followed by quick addition of Pd(PPh$_3$)$_4$ (4.18 g, 3.61 mmol, 0.04 equiv). The reaction was then heated to 88° C., until complete. The course of the reaction was monitored via LC, until deemed complete at the seven hour mark. At this point, the reaction vessel was cooled to ambient temperature, the caustic layer removed, 200 mL of a 20% HCl solution was added, and the reaction heated under reflux for five hours. The reactor was cooled to ambient temperature, the stirring was halted, and the aqueous layer removed. The organic layer washed with brine, dried over MgSO$_4$, then filtered, and concentrated via rotary evaporation, to give an off-white solid. The crude residue was washed with acetonitrile and dried under vacuum to provide pure L2 ligand (44.2 grams, 60% yield). $^1$H NMR (400 MHz, CDCl$_3$) δ 8.13 (d, J=7.6 Hz, 4H), 7.25 (m, 18H), 6.91 (dd, J=8.3, 2.0 Hz, 2H), 6.64 (d, J=8.3 Hz, 2H), 6.30 (s, 2H), 4.45 (m, 2H), 2.41 (s, 6H), 2.32 (s, 6H), 2.16 (m, 1H), 1.68 (m, 1H), and 1.14 (d, J=6.1 Hz, 6H). $^{13}$C{$^1$H} NMR (101 MHz, CDCl$_3$) δ 151.4, 148.4, 141.4, 141.3, 133.1, 131.9, 130.6, 130.1, 129.3, 128.8, 128.0, 125.8, 125.4, 123.4, 123.4, 120.3, 119.6, 114.9, 110.4, 110.3, 73.3, 42.7, 20.8, 20.7, and 19.9.

4f. Preparation of Pro-Catalyst 4 (I4)

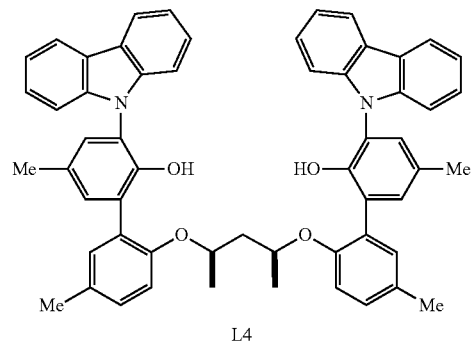

A 5 reactor vessel was charged with 3 of toluene, and cooled to −30° C. To this, was added, ZrCl$_4$ (29.6 g, 127 mmol), followed by MeMgBr (161 mL of a 3M solution, 484 mmol). The resulting mixture was allowed to stir for five minutes, after which, the ligand (100 g, 121 mmol) was added. The suspension was allowed to gradually warm to room temperature, stirred for an additional three hours, and then filtered. The filtrate was concentrated, and analyzed via $^1$H NMR spectroscopy, which showed the presence of I4, but with low purity. The filter cake was then extracted with methylene chloride (1.5 L), and concentrated, to provide I4 in high purity (66 grams, 58% yield). $^1$H NMR (400 MHz, CDCl$_3$) δ 8.30 (dd, J=8.5, 12.1 Hz, 2H), 8.12 (dd, J=7.4, 10.3 Hz, 2H), 7.57 (d, J=8.25 Hz, 1H), 7.26-7.0 (m, 21 H), 6.40 (dd, J=2.2, 8.5 Hz, 1H), 6.30 (dd, J=2.5, 7.15 Hz, 1H), 4.44 (d, J=8.1 Hz, 1H), 4.30 (d, J=7.9 Hz, 1H), 4.05 (m, 1H), 3.70 (m, 1H), 2.38 (s, 3H), 2.37 (s, 3H), 2.23 (s, 6H), 1.35 (m, 1H), 0.59 (d, J=6.8 Hz, 3H), 0.43 (d, J=7.2 Hz, 3H), -1.51 (s, 3H), and -1.68 (s, 3H).

EXAMPLE 5

5a. Preparation of rac-4,4'-pentane-2,4-diylbis(oxy))bis(3-bromo-1-fluorobenzene)

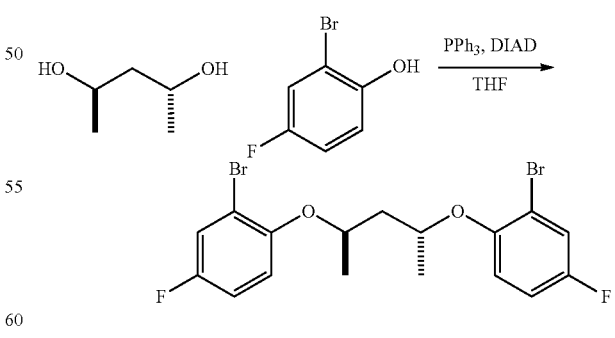

A 2-L, round bottomed flask, equipped with a magnetic stir, was charged with rac-2,4-pentanediol (16.9 g, 162.3 mmol), 2-bromo-4-fluorophenol (65.09 g, 340.8 mmol), triphenyl-phosphine (89.38 g, 340.76 mmol), and THF (600 mL), and was cooled to 0° C., in an ice-water bath. A solution of DIAD (67.09 g, 340.76 mmol), in THF (130 mL), was slowly added to the flask, via the addition funnel. The resulting mixture was stirred overnight, at ambient temperature, and the following day, the volatiles were removed under reduced pressure. Pentane (700 mL) was added to the residue, and the slurry was stirred at room temperature for 30 minutes. The insoluble solid was filtered, rinsed with pentane (100 mL ×3), and then concentrated, under reduced pressure, to give an oil residue. The oil residue was dissolved in hexane (100 mL), and then passed through a pad of silica gel, eluting first with hexane (300 mL), followed by hexane-EtOAc (4:1 in volume), furnishing the desired product in high purity (42.1 grams, 48% yield). $^1$H NMR (400 MHz, CDCl$_3$): δ 7.20 (dd, J=7.8, 3.0 Hz, 2H), 6.83 (ddd, J=9.1, 7.7, 3.0 Hz, 2H), 6.74 (dd, J=9.1, 4.9 Hz, 2H), 4.68 (sextet, J=6.1 Hz, 2H), 2.05 (dd, J=7.3, 5.5 Hz, 2H), and 1.35 (d, J=6.2 Hz, 6H). $^{13}$C{$^1$H} NMR (101 MHz, CDCl$_3$): δ 156.5 (d, J=243.2 Hz), 151.1 (d, J =2.8 Hz), 120.1 (d, J=25.8 Hz), 116.0 (d, J=8.4 Hz), 114.8 (d, J=22.7 Hz), 113.3 (d, J=10.1 Hz), 73.4, 44.8, and 20.2. $^{19}$F NMR (376 MHz, C$_6$D$_6$) δ −121.22.

5e. Preparation of Ligand 5 (L5)

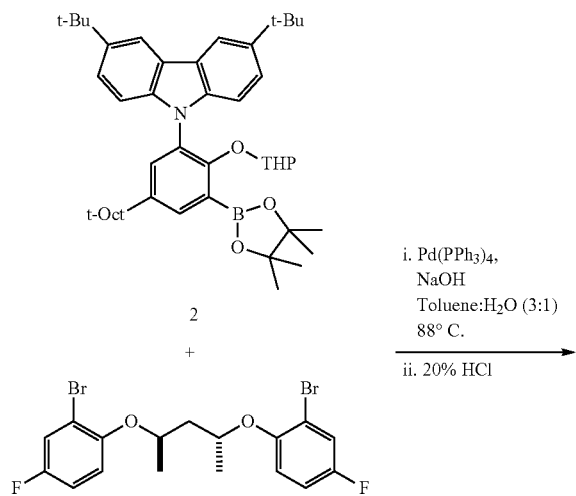

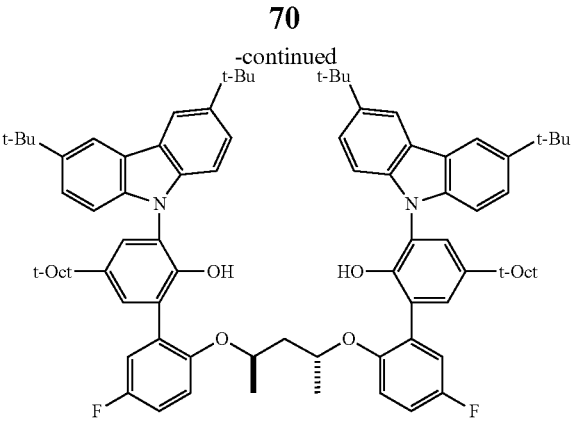

To a vial, was added, the rac-4,4'-pentane-2,4-diylbis(oxy))bis(3-bromo-1-fluorobenzene) (0.602 g, 1.34 mmol) and the top group (2.04 g, 2.94 mmol) dissolved in 5 mL of toluene, under a nitrogen atmosphere, with stirring. To this, was added, NaOH (0.321 g dissolved in 1 mL of water, 8.02 mmol), followed by quick addition of Pd(PPh$_3$)$_4$ (0.060 g, 0.054 mmol), and the reaction heated to 88° C. The course of the reaction was monitored via LC, until deemed complete at the five hour mark. At this point, the reaction vessel was cooled to rt, the caustic layer removed, 2 mL of a 20% HCl solution was added, and the reaction heated once more to reflux for five hours. The reactor was cooled to rt, the aqueous layer removed, and the organic layer washed with brine, and dried over MgSO$_4$. Filtration to remove the MgSO$_4$, followed by concentration via rotary evaporation, gave an off-white solid, which was washed with acetonitrile, and the remaining solid dried under vacuum to provide pure L5 (1.41 grams, 84% yield). $^1$H NMR (400 MHz, CDCl$_3$): δ 8.19 (dt, J=3.3, 1.5 Hz, 4H), 7.44 (m, 6H), 7.32 (t, J=1.8 Hz, 2H), 7.07 (m, 6H), 6.66 (td, J=8.3, 3.1 Hz, 2H), 6.41 (dd, J=9.2, 4.6 Hz, 2H), 5.91 (s, 2H), 4.36 (m, 2H), 1.74 (s, 4H), 1.71 (m, 2H), 1.49 (s, 18H), 1.47 (s, 18H), 1.39 (s, 12H), 0.92 (d, J=5.8 Hz, 6H), and 0.80 (s, 18H). $^{13}$C NMR (101 MHz, CDCl$_3$): δ 157.5 (d, J=241.3 Hz), 150.0 (d, J=1.8 Hz), 147.9, 142.8, 142.6 (d, J=8.4 Hz), 139.8 (d, J=10.9 Hz), 130.2 (d, J=7.8 Hz), 129.0, 127.2, 126.56, 124.8, 123.6 (d, J=13.3 Hz), 123.3, 123.1, 118.2 (d, J=23.4 Hz), 116.4, 116.3, 115.4 (d, J=22.8 Hz), 109.2 (d, J=31.6 Hz), 73.1, 57.0, 44.7, 38.2, 34.7 (d, J=1.6 Hz), 32.4, 32.0, 31.9, 31.7, 31.6, and 19.7. $^{19}$F NMR (376 MHz, C$_6$D$_6$) δ −121.96.

5e. Preparation of Pro-Catalyst 5 (I5)

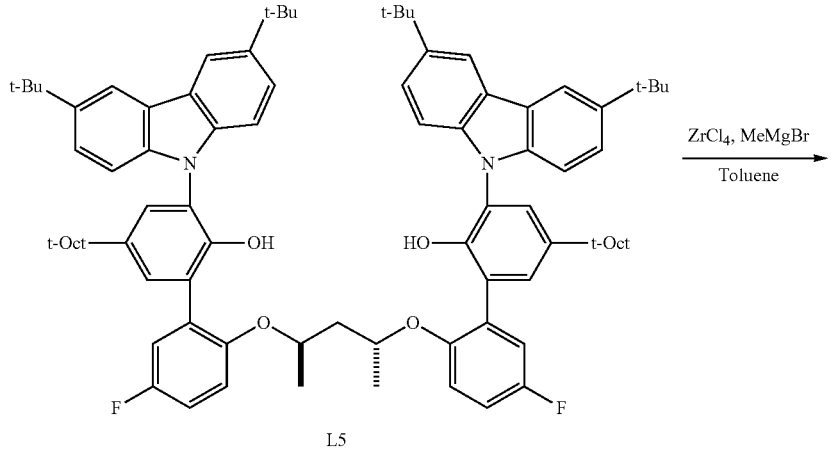

-continued

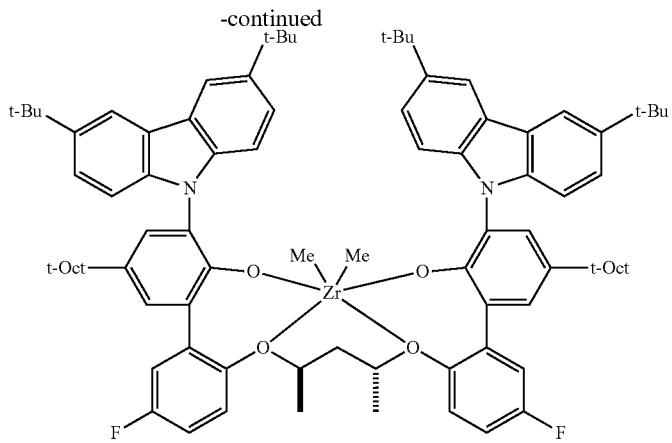

I5

A flask was charged with 30 mL of cold toluene (−30 ° C.) and ZrCl4 (0.340 grams, 1.50 mmol). To the resulting cold suspension, was added, MeMgBr (1.90 mL of a 3M solution in Et$_2$O, 5.70 mmol). The resulting mixture was allowed to stir for 2-3 minutes, at which point, the ligand L5 (1.79 grams, 1.43 mmol) was added. The suspension was allowed to warm to room temperature naturally, and was stirred for two hours. The solvent was then removed under vacuum, and the dark brown suspension was extracted with hexanes (100 mL) and filtered. The filtrate was collected, and dried under vacuum, providing I5 as an off white solid in good purity (1.46 grams, 75% yield). $^1$H NMR (400 MHz, C$_6$D$_6$) δ 8.59 (m, 2H), 8.40 (m, 2H), 7.79 , 7.52 (m, 8H), 7.43 (dd, J=8.4, 1.9 Hz, 2H), 7.23 (dd, J=12.7, 2.5 Hz, 2H), 6.98 (dt, J=9.0, 3.2 Hz, 2H), 6.66 (ddd, J=8.9, 7.4, 3.2 Hz, 1H), 6.59 (ddd, J=8.9, 7.4, 3.1 Hz, 1H), 5.04 (dd, J=8.9, 5.0 Hz, 1H), 4.88 (dd, J=8.9, 4.9 Hz, 1H), 4.16 (m, 1H), 3.74 (m, 1H), 1.80 (m, 1H), 1.67-1.57 (m, 5H), 1.48 (s, 9H), 1.47 (s, 9H), 1.31 (s, 9H), 1.30 (s, 9H), 1.28-1.20 (m, 12H), 0.86 (s, 9H), 0.85 (s, 9H), 0.59 (d, J=6.4 Hz, 3H), 0.40 (d, J=6.6 Hz, 3H), −0.82 (s, 3H), −0.82 (s, 3H). $^{19}$F NMR (376 MHz, C$_6$D$_6$) δ −114.59, and −114.68.

Preparation of ethylene Based Polymers in a Single Reactor

All raw materials (ethylene, 1-octene) and the process solvent (a narrow boiling range high-purity isoparaffinic solvent trademarked ISOPAR E, commercially available from ExxonMobil Corporation) are purified with molecular sieves before introduction into the reaction environment. Hydrogen is supplied in pressurized cylinders as a high purity grade, and is not further purified. The reactor monomer feed (ethylene) stream is pressurized via mechanical compressor to above reaction pressure at 525 psig. The solvent and comonomer (1-octene) feed is pressurized via mechanical positive displacement pump to above reaction pressure at 525 psig. The individual catalyst components are manually batch diluted to specified component concentrations with purified solvent (ISOPAR E) and pressured to above reaction pressure at 525 psig. All reaction feed flows are measured with mass flow meters, and independently controlled with computer automated valve control systems.

The continuous solution polymerization reactor consists of a liquid full, non-adiabatic, isothermal, circulating, and independently controlled loop. The reactor has independent control of all fresh solvent, monomer, comonomer, hydrogen, and catalyst component feeds. The combined solvent, monomer, comonomer and hydrogen feed to the reactor is temperature controlled to anywhere from 5° C. to 50° C., and typically at 25° C., by passing the feed stream through a heat exchanger. The fresh comonomer feed to the polymerization reactor is fed in with the solvent feed. The total fresh feed to each polymerization reactor is injected into the reactor at two locations, with roughly equal reactor volumes between each injection location. The fresh feed is controlled typically with each injector receiving half of the total fresh feed mass flow. The catalyst components are injected into the polymerization reactor through specially designed injection stingers, and are each separately injected into the same relative location in the reactor with no contact time prior to the reactor. The primary catalyst component feed is computer controlled to maintain the reactor monomer concentration at a specified target. The cocatalyst components are fed, based on calculated specified molar ratios to the primary catalyst component. Immediately following each fresh injection location (either feed or catalyst), the feed streams are mixed with the circulating polymerization reactor contents with Kenics static mixing elements. The contents of each reactor are continuously circulated through heat exchangers responsible for removing much of the heat of reaction, and with the temperature of the coolant side responsible for maintaining isothermal reaction environment at the specified temperature. Circulation around each reactor loop is provided by a screw pump.

The effluent from the first polymerization reactor (containing solvent, monomer, comonomer, hydrogen, catalyst components, and molten polymer) exits the first reactor loop and passes through a control valve (responsible for maintaining the pressure of the first reactor at a specified target). As the stream exits the reactor, it is contacted with water to stop the reaction. In addition, various additives such as anti-oxidants, can be added at this point. The stream then goes through another set of Kenics static mixing elements to evenly disperse the catalyst kill and additives.

Following additive addition, the effluent (containing solvent, monomer, comonomer, hydrogen, catalyst components, and molten polymer) passes through a heat exchanger to raise the stream temperature in preparation for separation of the polymer from the other lower boiling reaction components. The stream then enters a two stage separation and devolatization system, where the polymer is removed from the solvent, hydrogen, and unreacted monomer and comonomer. The recycled stream is purified before entering the reactor again. The separated and devolatized polymer melt is pumped through a die specially designed for underwater pelletization, cut into uniform solid pellets, dried, and transferred into a hopper. After validation of initial polymer properties the solid polymer pellets are manually dumped into a box for storage. Each box typically holds approximately 1200 pounds of polymer pellets.

The non-polymer portions, removed in the devolatilization step, pass through various process steps, which separate most of the ethylene, which is removed from the system, to a vent destruction unit (it is recycled in manufacturing units). Most of the solvent is recycled back to the reactor, after passing through purification beds. This solvent can still have unreacted co-monomer in it, which is fortified with fresh co-monomer prior to re-entry to the reactor. This fortification of the co-monomer is an essential part of the product density control method. This recycle solvent can still have some hydrogen, which is then fortified with fresh hydrogen to achieve the polymer molecular weight target. A very small amount of solvent leaves the system as a co-product, due to solvent carrier in the catalyst streams and a small amount of solvent that is part of commercial grade co-monomers.

INVENTIVE EXAMPLES

I1

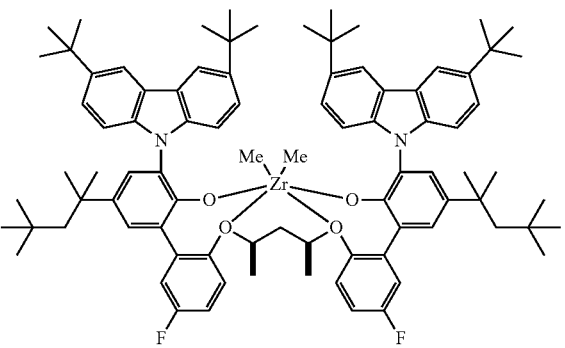

I2

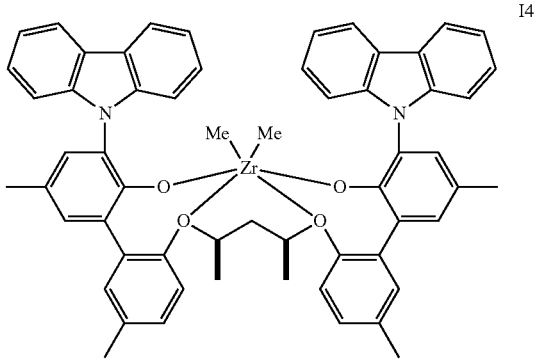

-continued

I3

I4

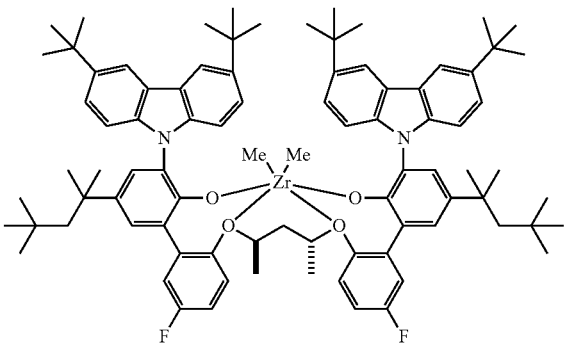

I5

I6

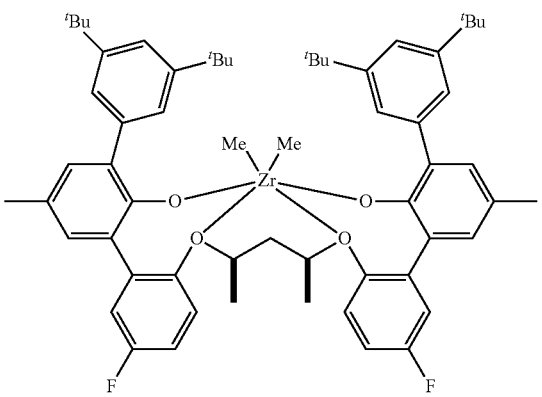

COMPARATIVE EXAMPLES
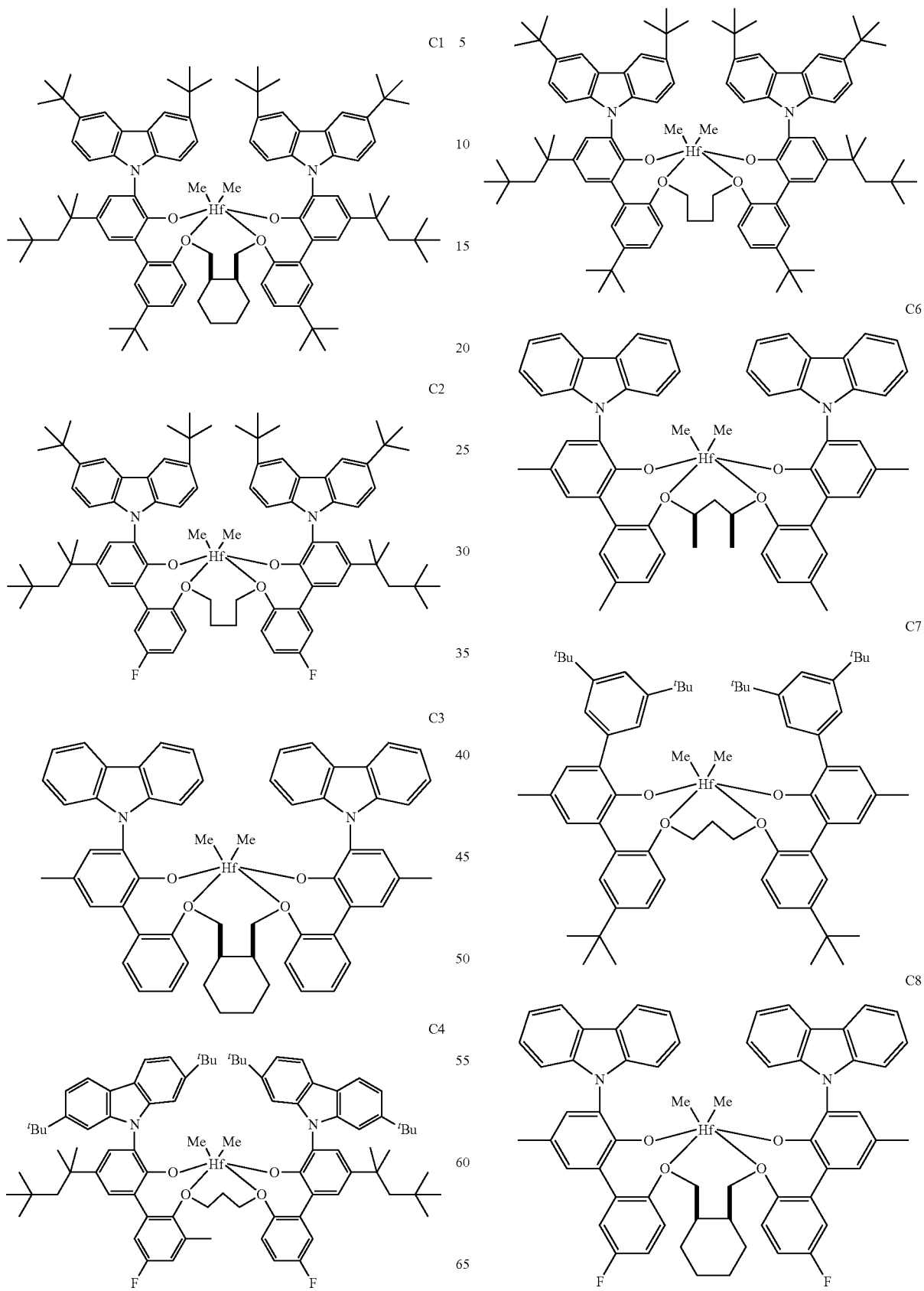

-continued
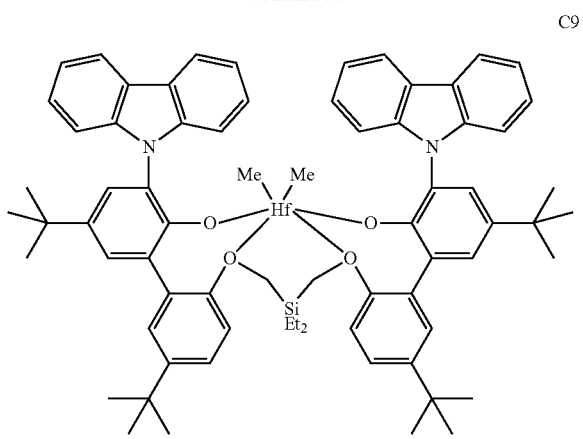
C9
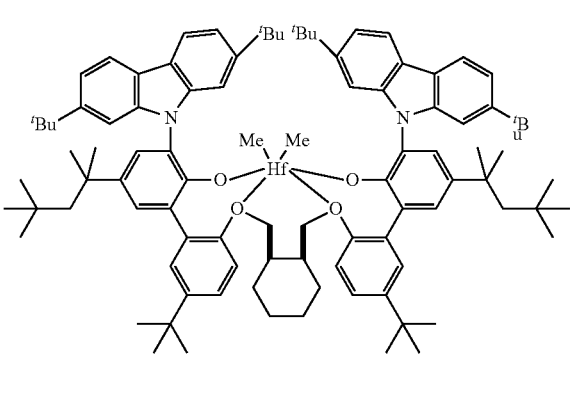
C13
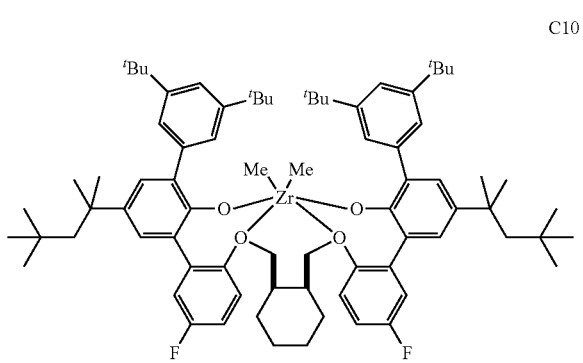
C10
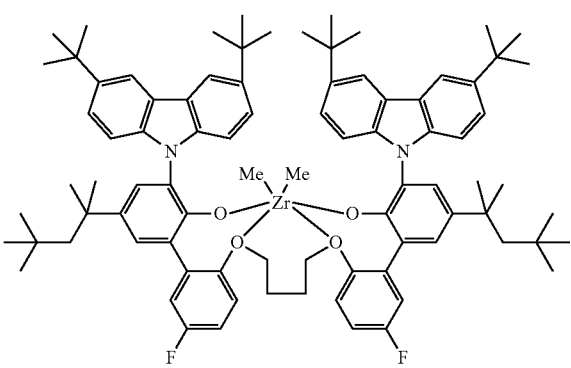
C14
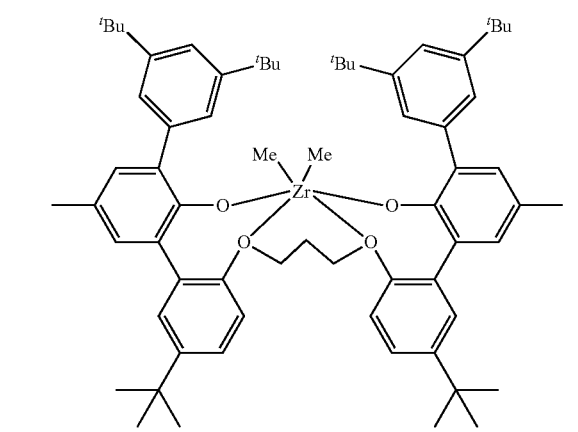
C11
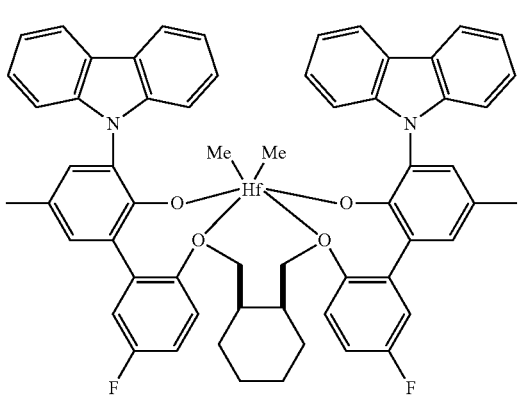
C15
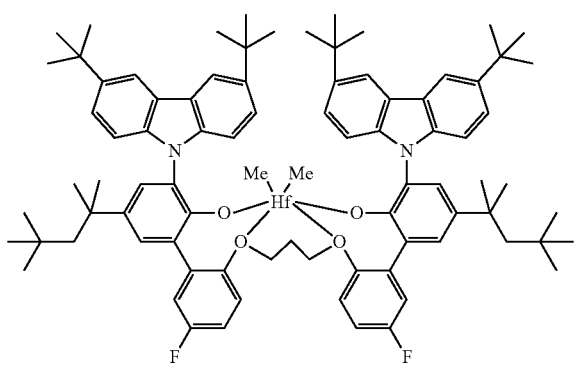
C12
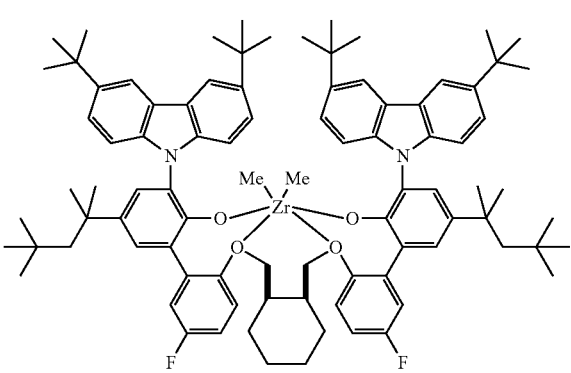
C16

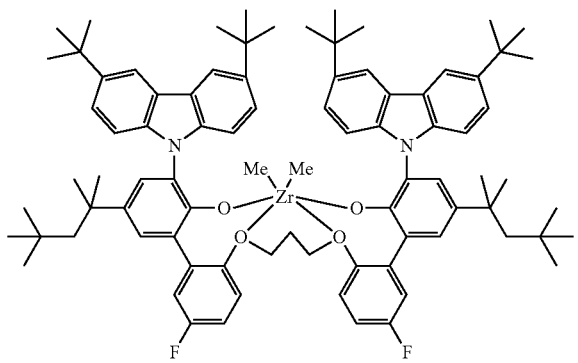

C17

Single Reactor

Batch Reactor Ethylene/Octene Copolymerizations

A one gallon (3.79 L), stirred autoclave reactor was charged with ca 1.35 kg of ISOPAR E mixed alkanes solvent and 1-octene (250 g). The reactor was then heated to the desired temperature (140° C. or 175° C.), and charged with hydrogen (if desired), followed by an amount of ethylene to bring the total pressure to ca 450 psig (2.95 MPa). The ethylene feed was passed through an additional purification column, prior to entering the reactor. The catalyst composition was prepared in a drybox, under inert atmosphere, by mixing the desired pro-catalyst and a cocatalyst (a mixture of 1.2 equiv of tetrakis(pentafluorophenyl)borate(1-) amine, and 50 equiv of triisobutylaluminum modified alumoxane (MMAO-3A)), with additional solvent, to give a total volume of about 17 mL. The activated catalyst mixture was then quick-injected into the reactor. The reactor pressure and temperature were kept constant, by feeding ethylene during the polymerization, and cooling the reactor as needed. After 10 minutes, the ethylene feed was shut off, and the solution transferred into a nitrogen-purged resin kettle. The polymer was thoroughly dried in a vacuum oven, and the reactor was thoroughly rinsed with hot ISOPAR E between polymerization runs.

TABLE 1

Batch reactor inventive examples at 140° C.

| Ex. | | Eff.[a] | $H_2$ (mmol) | Density (g/cm³) | MWD[b] | $M_w$ (g/mole) | $M_w$ red.[c] |
|---|---|---|---|---|---|---|---|
| Inv. | I1 | 1.09 | 0 | 0.8941 | 2.45 | 1,199,037 | 80 |
| | | 0.83 | 40 | 0.8982 | 2.06 | 243,394 | |
| | I2 | 2.25 | 0 | 0.8906 | 2.27 | 1,149,440 | 78 |
| | | 1.61 | 40 | 0.8938 | 1.88 | 248,793 | |
| | I3 | 2.11 | 0 | 0.8714 | 2.67 | 1,136,984 | 87 |
| | | 3.82 | 40 | 0.8920 | 2.60 | 152,066 | |
| | I4 | 2.09 | 0 | 0.8904 | 2.49 | 1,135,405 | 79 |
| | | 1.32 | 40 | 0.8965 | 1.88 | 241,028 | |
| | I5 | 2.95 | 0 | 0.8770 | 2.20 | 1,032,752 | 88 |
| | | 2.21 | 40 | 0.8890 | 2.48 | 123,443 | |
| | I6 | 1.98 | 0 | 0.8915 | 2.56 | 994,735 | 82 |
| | | 1.14 | 40 | 0.8974 | 2.25 | 175,423 | |

[a]Efficiency calculated in units of $10^6$ grams of polymer/gram of active metal (Hf or Zr).
[b]MWD is defined as the ratio of the weight average molecular weight to the number average molecular weight.
[c]$M_w$ red. is defined as the % decrease in the weight average molecular weight for the run with 40 mmol hydrogen added, versus the analogous run carried out without hydrogen. {[Mw(at zero hydrogen)—Mw(at 40 mmole H2)]/Mw(at zero hydrogen)} × 100.

TABLE 2

Batch reactor comparative examples at 140° C.

| Ex. | | Eff.[a] | $H_2$ (mmol) | Density (g/cm³) | MWD[b] | Mw (g/mole) | $M_w$ red.[c] |
|---|---|---|---|---|---|---|---|
| Comp. | C1 | 1.71 | 0 | 0.8818 | 3.66 | 1,147,480 | 51 |
| | | 0.99 | 40 | 0.8850 | 3.05 | 562,452 | |
| | C2 | 1.98 | 0 | 0.8824 | 2.43 | 1,071,483 | 44 |
| | | 0.65 | 40 | 0.8939 | 1.98 | 600,188 | |
| | C3 | 1.72 | 0 | 0.8764 | 2.65 | 1,059,523 | 65 |
| | | 1.55 | 40 | 0.8765 | 2.06 | 368,157 | |
| | C4 | 1.37 | 0 | 0.9090 | 2.29 | 929,764 | 38 |
| | | 0.99 | 40 | 0.9098 | 2.03 | 572,963 | |
| | C5 | 0.29 | 0 | 0.8904 | 2.15 | 869,055 | 44 |
| | | 0.27 | 40 | 0.8907 | 2.11 | 484,640 | |
| | C6 | 2.06 | 0 | 0.8863 | 2.23 | 801,664 | 54 |
| | | 1.72 | 40 | 0.8895 | 1.99 | 370,225 | |
| | C7 | 0.15 | 0 | 0.8886 | 2.15 | 734,147 | 22 |
| | | 0.36 | 40 | 0.8869 | 2.15 | 569,216 | |
| | C8 | 0.59 | 0 | 0.8696 | 2.40 | 700,687 | 67 |
| | | 0.61 | 40 | 0.8714 | 1.97 | 230,640 | |
| | C9 | 1.17 | 0 | 0.8853 | 2.33 | 653,132 | 33 |
| | | 1.20 | 40 | 0.8854 | 2.04 | 435,209 | |
| | C10 | 0.75 | 0 | 0.8868 | 2.39 | 487,032 | 69 |
| | | 0.68 | 40 | 0.8913 | 1.90 | 150,729 | |
| | C11 | 1.34 | 0 | 0.8912 | 1.98 | 473,396 | 52 |
| | | 1.11 | 40 | 0.8956 | 1.91 | 227,456 | |
| | C12 | 1.39 | 0 | 0.8776 | 1.92 | 459,271 | 25 |
| | | 0.90 | 40 | 0.8788 | 1.90 | 342,473 | |
| | C13 | 1.30 | 0 | 0.9021 | 2.43 | 400,539 | 44 |
| | | 0.88 | 40 | 0.9041 | 1.98 | 220,510 | |
| | C14 | 4.35 | 0 | 0.8898 | 2.13 | 262,402 | 50 |
| | | 2.06 | 40 | 0.8810 | 1.92 | 131,045 | |
| | C15 | 3.97 | 0 | 0.8838 | 2.13 | 212,857 | 65 |
| | | 2.97 | 40 | 0.8863 | 2.00 | 75,201 | |
| | C16 | 4.84 | 0 | 0.8909 | 1.97 | 205,252 | 46 |
| | | 3.43 | 40 | 0.8933 | 1.89 | 111,590 | |
| | C17 | 3.48 | 0 | 0.8939 | 1.98 | 86,594 | 17 |
| | | 3.48 | 40 | 0.8944 | 1.95 | 71,689 | |

[a]Efficiency calculated in units of $10^6$ grams of polymer/gram of active metal (Hf or Zr).
[b]MWD is defined as the ratio of the weight average molecular weight to the number average molecular weight.
[c]$M_w$ red. is defined as the % decrease in the weight average molecular weight for the run with 40 mmol hydrogen added, versus the analogous run carried out without hydrogen. {[Mw(at zero hydrogen)—Mw(at 40 mmole H2)]/Mw(at zero hydrogen)} × 100.

TABLE 3

Batch reactor inventive examples at 175° C.

| Ex. | | Eff.[a] | $H_2$ (mmol) | Density (g/cm³) | MWD[b] | $M_w$ (g/mole) | $M_w$ red.[c] |
|---|---|---|---|---|---|---|---|
| Inv. | I1 | 0.14 | 0 | 0.8948 | 2.25 | 636,796 | 75 |
| | | 0.14 | 40 | 0.8982 | 2.36 | 156,883 | |
| | I2 | 0.61 | 0 | 0.8876 | 2.17 | 498,188 | 72 |
| | | 0.50 | 40 | 0.8923 | 2.01 | 140,276 | |
| | I3 | 0.67 | 0 | 0.8826 | 2.09 | 725,982 | 82 |
| | | 0.65 | 40 | 0.8894 | 3.15 | 131,800 | |
| | I4 | 0.24 | 0 | 0.8977 | 2.28 | 621,637 | 83 |
| | | 0.38 | 40 | 0.9001 | 2.05 | 108,762 | |
| | I5 | 0.31 | 0 | 0.8850 | 1.87 | 551,755 | 83 |
| | | 0.50 | 40 | 0.8902 | 2.07 | 95,582 | |
| | I6 | 0.13 | 0 | 0.8891 | 2.26 | 257,305 | 73 |
| | | 0.21 | 40 | 0.8960 | 1.93 | 68,505 | |

[a]Efficiency calculated in units of $10^6$ grams of polymer/gram of active metal (Hf or Zr).
[b]MWD is defined as the ratio of the weight average molecular weight to the number average molecular weight.
[c]$M_w$ red. is defined as the % decrease in the weight average molecular weight for the run with 40 mmol hydrogen added, versus the analogous run carried out without hydrogen. {[Mw(at zero hydrogen)—Mw(at 40 mmole H2)]/Mw(at zero hydrogen)} × 100.

TABLE 4

Batch reactor comparative examples at 175° C.

| Ex. | | Eff.[a] | H$_2$ (mmol) | Density (g/cm$^3$) | MWD[b] | M$_w$ (g/mole) | M$_w$ red.[c] |
|---|---|---|---|---|---|---|---|
| omp. | C1 | 0.42 | 0 | 0.8833 | 2.61 | 453,963 | 41 |
| | | 0.35 | 40 | 0.8849 | 2.48 | 266,541 | |
| | C4 | 0.96 | 0 | 0.9068 | 2.23 | 526,468 | 46 |
| | | 0.61 | 40 | 0.9111 | 2.05 | 286,598 | |
| | C5 | 0.02 | 0 | 0.8936 | 2.60 | 255,665 | 40 |
| | | 0.02 | 40 | 0.8944 | 2.51 | 154,366 | |
| | C6 | 0.69 | 0 | 0.8889 | 1.95 | 415,885 | 50 |
| | | 0.49 | 40 | 0.8899 | 2.23 | 208,318 | |
| | C7 | 0.48 | 0 | 0.8848 | 1.94 | 349,518 | 42 |
| | | 1.20 | 40 | 0.8846 | 1.99 | 203,768 | |
| | C8 | 0.10 | 0 | 0.8720 | 1.96 | 273,129 | 50 |
| | | 0.13 | 40 | 0.8722 | 2.04 | 137,115 | |
| | C10 | 0.04 | 0 | 0.8834 | 2.02 | 190,743 | 62 |
| | | 0.04 | 40 | 0.8914 | 1.79 | 72,327 | |
| | C11 | 0.61 | 0 | 0.8898 | 1.97 | 272,971 | 62 |
| | | 0.91 | 40 | 0.8924 | 1.94 | 103,684 | |
| | C12 | 0.58 | 0 | 0.8783 | 2.00 | 273,763 | 29 |
| | | 0.73 | 40 | 0.8779 | 2.01 | 193,955 | |
| | C13 | 0.64 | 0 | 0.9053 | 2.28 | 185,525 | 45 |
| | | 0.50 | 40 | 0.9077 | 2.31 | 102,469 | |
| | C14 | 1.14 | 0 | 0.8906 | 1.88 | 172,400 | 56 |
| | | 1.09 | 40 | 0.8927 | 1.86 | 75,478 | |
| | C15 | 0.68 | 0 | 0.8868 | 2.04 | 121,378 | 61 |
| | | 0.62 | 40 | 0.8883 | 1.88 | 47,782 | |
| | C16 | 1.32 | 0 | 0.8916 | 2.13 | 139,532 | 48 |
| | | 1.52 | 40 | 0.8921 | 2.07 | 72,901 | |
| | C17 | 2.28 | 0 | 0.8923 | 1.88 | 65,390 | 26 |
| | | 3.57 | 40 | 0.8945 | 2.01 | 47,603 | |

[a]See footnote for Tables 1-3 above
[b]See footnote for Tables 1-3 above.
[c]See footnote for Tables 1-3 above.

Continuous Reactor Ethylene/Octene Copolymerizations

Raw materials (ethylene, 1-octene) and the process solvent (a narrow boiling range high-purity isoparaffinic solvent trademarked SBP 100/140, commercially available from SHELL) are purified with molecular sieves, before introduction into the reaction environment. Hydrogen is supplied at 1160 psig (80 bar), and reduced to about 580 psig (40 bar); and is supplied as a high purity grade, and is not further purified. The reactor monomer feed (ethylene) stream is pressurized, via mechanical compressor, to above reaction pressure at 525 psig. The solvent and comonomer (1-octene) feed is pressurized, via mechanical positive displacement pump, to above reaction pressure at 525 psig. Modified methylaluminoxane (MMAO), commercially available from AkzoNobel, is used as an impurity scavenger. The individual catalyst components (procatalyst cocatalyst) are manually batch diluted, to specified component concentrations, with purified solvent (ISOPAR E), and pressurized to 525 psig. The cocatalyst is [HNMe(C$_{18}$H$_{37}$)$_2$][B(C$_6$F$_5$)$_4$], commercially available from Boulder Scientific, and is used at a 1.2 molar ratio relative to the procatalyst. All reaction feed flows are measured with mass flow meters, and independently controlled with computer automated valve control systems.

The continuous solution polymerizations are carried out in a 5L, continuously stirred-tank reactor (CSTR). The reactor has independent control of all fresh solvent, monomer, comonomer, hydrogen, and catalyst component feeds. The combined solvent, monomer, comonomer and hydrogen feed to the reactor is temperature controlled, to anywhere from 5° C. to 50° C., and typically 25° C. The fresh comonomer feed to the polymerization reactor is fed in with the solvent feed. The cocatalyst is fed based on a calculated specified molar ratio (1.2 molar equivalents) to the procatalyst component. Immediately following each fresh injection location, the feed streams are mixed, with the circulating polymerization reactor contents, with static mixing elements. The effluent from the polymerization reactor (containing solvent, monomer, comonomer, hydrogen, catalyst components, and molten polymer) exits the first reactor loop, and passes through a control valve (responsible for maintaining the pressure of the first reactor at a specified target). As the stream exits the reactor, it is contacted with water to stop the reaction. In addition, various additives such as anti-oxidants, can be added at this point. The stream then goes through another set of static mixing elements, to evenly disperse the catalyst kill and additives.

Following additive addition, the effluent (containing solvent, monomer, comonomer, hydrogen, catalyst components, and molten polymer) passes through a heat exchanger, to raise the stream temperature, in preparation for separation of the polymer from the other lower boiling reaction components. The stream then enters a two stage separation and devolatization system, where the polymer is removed from the solvent, hydrogen, and unreacted monomer and comonomer. The separated and devolatized polymer melt is pumped through a die specially designed for underwater pelletization, cut into uniform solid pellets, dried, and transferred into a box for storage.

TABLE 5

Continuous process single reactor polymerization data for 0.5 g/10 min I$_2$, 0.911-0.913 g/cm$^3$ density resin produced at 150° C.

| Ex. | Cat Eff MM g polymer/ g Metal | H$_2$ Mol % | Density g/cm$^3$ | I$_2$ g/10 min | I$_{10}$/I$_2$ | Mw g/mole | MWD Mw/Mn | $\eta_0$ Pa·s | C2 feed kg/h | C8 feed kg/h | C2 Conv % | ZSVR |
|---|---|---|---|---|---|---|---|---|---|---|---|---|
| I1 | 1.40 | 0.39 | 0.912 | 0.48 | 5.8 | 126,978 | 2.1 | 15,313 | 3.9 | 1.88 | 79.0 | 1.57 |
| I3 | 2.70 | 0.34 | 0.913 | 0.51 | 5.6 | 119,457 | 2.0 | 15,325 | 3.9 | 1.35 | 78.6 | 1.97 |
| I4 | 2.90 | 0.34 | 0.912 | 0.49 | 5.6 | 124,951 | 2.1 | 15,015 | 3.9 | 1.88 | 78.5 | 1.64 |
| I5 | 9.80 | 0.33 | 0.912 | 0.47 | 6.6 | 131,790 | 2.3 | 19,589 | 3.9 | 1.70 | 78.6 | 1.76 |
| C1 | 2.20 | 2.40 | 0.913 | 0.51 | 6.7 | 128,928 | 2.8 | 18,957 | 3.2 | 1.34 | 75.6 | 1.84 |
| C2 | 0.70 | 2.11 | 0.913 | 0.46 | 5.7 | 132,043 | 2.0 | 16,077 | 4.0 | 1.24 | 77.0 | 1.43 |
| C3 | 0.99 | 1.25 | 0.912 | 0.45 | 6.4 | 123,924 | 2.3 | 18,814 | 3.9 | 1.02 | 78.5 | 2.11 |
| C7 | 0.58 | 1.30 | 0.911 | 0.52 | 5.8 | 126,135 | 2.1 | 14,993 | 4.0 | 1.80 | 76.5 | 1.58 |
| C9 | 2.50 | 2.43 | 0.913 | 0.52 | 6.0 | 126,416 | 2.0 | 20,779 | 3.2 | 1.20 | 75.0 | 2.17 |
| C11 | 3.10 | 0.41 | 0.913 | 0.53 | 6.6 | 114,319 | 2.1 | 19,493 | 3.9 | 1.86 | 78.4 | 2.94 |

TABLE 6

Continuous process single reactor polymerization data for 1 g/10 min I$_2$, 0.912-0.914 g/cm$^3$ density resin produced at 150° C.

| Ex. | Cat Eff MM g polymer/ g Metal | H$_2$ Mol % | Density g/cm3 | I$_2$ | I$_{10}$/I$_2$ | Mw g/mole | MWD Mw/Mn | η$_0$ Pa · s | C2 feed kg/h | C8 feed kg/h | C2 Conv % | ZSVR |
|---|---|---|---|---|---|---|---|---|---|---|---|---|
| I1 | 1.30 | 0.49 | 0.913 | 0.93 | 5.7 | 107,553 | 2.1 | 7,923 | 3.9 | 1.91 | 78.7 | 1.49 |
| I3 | 2.50 | 0.40 | 0.913 | 0.97 | 5.8 | 100,898 | 2.0 | 7,283 | 3.9 | 1.55 | 78.9 | 1.73 |
| I4 | 3.00 | 0.41 | 0.914 | 1.05 | 5.5 | 99,934 | 2.1 | 6,821 | 3.9 | 2.00 | 78.6 | 1.68 |
| C3 | 0.93 | 1.58 | 0.912 | 1.06 | 5.9 | 102,843 | 2.3 | 7,468 | 3.9 | 1.12 | 78.6 | 1.66 |
| C11 | 3.60 | 0.50 | 0.913 | 1.08 | 6.2 | 96,062 | 2.1 | 8,045 | 3.9 | 2.10 | 78.4 | 2.29 |

TABLE 7

Continuous process single reactor polymerization data for 0.3 g/10 min I$_2$, 0.894-0.897 g/cm$^3$ density resin.

| Ex. | Cat Eff MM g poly/g M | H$_2$ Mol % | Density g/cm$^3$ | I$_2$ g/10 min | I$_{10}$/I$_2$ | Mw g/mole | MWD Mw/Mn | η$_0$ Pa · s | C2 feed kg/h | C8 feed kg/h | C2 Conv % | ZRSV |
|---|---|---|---|---|---|---|---|---|---|---|---|---|
| I1 | 1.30 | 0.16 | 0.896 | 0.30 | 6.1 | 140,072 | 2.1 | 25,889 | 3.5 | 3.75 | 78.6 | 1.86 |
| I3 | 1.70 | 0.14 | 0.896 | 0.33 | 6.2 | 135,798 | 2.1 | 25,513 | 3.5 | 3.10 | 78.0 | 2.05 |
| I4 | 7.40 | 0.15 | 0.894 | 0.30 | 6.0 | 142,265 | 2.1 | 31,491 | 3.5 | 4.30 | 78.6 | 2.11 |
| I5 | 4.40 | 0.13 | 0.895 | 0.33 | 7.4 | 150,969 | 2.5 | 31,700 | 3.5 | 3.10 | 78.4 | 1.76 |
| C3 | 1.50 | 0.72 | 0.897 | 0.31 | 6.6 | 134,397 | 2.5 | 29,459 | 3.6 | 2.15 | 78.5 | 2.46 |
| C11 | 3.80 | 0.23 | 0.896 | 0.30 | 7.1 | 124,628 | 2.2 | 36,212 | 3.5 | 3.65 | 78.2 | 3.98 |

As seen in the above tables, the inventive procatalysts can be used to effectively polymerize high molecular weight polymers (most weight average molecular weights greater than 100K g/mole), at sufficiently high temperatures (≥140° C.). The inventive procatalyts show a good responsiveness to H$_2$ in the batch polymerizations and the continuous polymerizations. Ethylene conversions greater than 78% were seen in the continuous polymerizations. For both batch and continuous polymerizations, high catalytic efficiencies were observed.

Test Methods

Density

Samples that are measured for density are prepared according to ASTM D-1928. Measurements are made within one hour of sample pressing using ASTM D- 792, Method B.

Melt Index

Melt index (I$_2$) is measured in accordance with ASTM-D 1238, Condition 190° C/2.16 kg, and is reported in grams eluted per 10 minutes. Melt flow rate (I$_{10}$) is measured in accordance with ASTM-D 1238, Condition 190° C./10 kg, and is reported in grams eluted per 10 minutes.

Conventional Gel Permeation Chromatography (conv. GPC)

A GPC-IR high temperature chromatographic system from, PolymerChAR (Valencia, Spain), was equipped with a Precision Detectors (Amherst, Mass.), 2-angle laser light scattering detector Model 2040, an IR5 infra-red detector and a 4-capillary viscometer, both from PolymerChAR. Data collection was performed using PolymerChAR InstrumentControl software and data collection interface. The system was equipped with an on-line, solvent degas device and pumping system from Agilent Technologies (Santa Clara, Calif.).

Injection temperature was controlled at 150 degrees Celsius. The columns used were three 10-micron "Mixed-B" columns from Polymer Laboratories (Shropshire, UK). The solvent used was 1,2,4 trichlorobenzene. The samples were prepared at a concentration of "0.1 grams of polymer in 50 milliliters of solvent." The chromatographic solvent and the sample preparation solvent each contained "200 ppm of butylated hydroxytoluene (BHT)." Both solvent sources were nitrogen sparged. Ethylene-based polymer samples were stirred gently at 160 degrees Celsius for three hours. The injection volume was 200 microliters, and the flow rate was 1 milliliters/minute. The GPC column set was calibrated by running 21 "narrow molecular weight distribution" polystyrene standards. The molecular weight (MW) of the standards ranges from 580 to 8,400,000 g/mole, and the standards were contained in six "cocktail" mixtures. Each standard mixture had at least a decade of separation between individual molecular weights. The standard mixtures were purchased from Polymer Laboratories. The polystyrene standards were prepared at "0.025 g in 50 mL of solvent" for molecular weights equal to, or greater than, 1,000,000 g/mole, and at "0.050 g in 50 mL of solvent" for molecular weights less than 1,000,000 g/mole.

The polystyrene standards were dissolved at 80° C., with gentle agitation, for 30 minutes. The narrow standards mixtures were run first, and in order of decreasing "highest molecular weight component," to minimize degradation. The polystyrene standard peak molecular weights were converted to polyethylene molecular weight using Equation 1 (as described in Williams and Ward, *J. Polym. Sci.*, Polym. Letters, 6, 621 (1968)):

$$M_{polyethylene} = A \times (M_{polystyrene})^B \quad \text{(Eqn. 1)},$$

where M is the molecular weight, A is equal to 0.4316 and B is equal to 1.0.

Number-average molecular weight (Mn(conv gpc)), weight average molecular weight (Mw-conv gpc), and z-average molecular weight (Mz(conv gpc)) were calculated according to Equations 2-4 below:

$$Mn(conv\ gpc) = \frac{\sum_{i=RV_{integration\ start}}^{i=RV_{integration\ end}} (IR_{measurement\ channel_i})}{\sum_{i=RV_{integration\ start}}^{i=RV_{integration\ end}} \left(\frac{IR_{measurement\ channel_i}}{M_{PE_i}}\right)},$$ (Eqn. 2)

$$Mw(conv\ gpc) = \frac{\sum_{i=RV_{integration\ start}}^{i=RV_{integration\ end}} (M_{PE_i} IR_{measurement\ channel_i})}{\sum_{i=RV_{integration\ start}}^{i=RV_{integration\ end}} (IR_{measurement\ channel_i})},$$ (Eqn. 3)

$$Mz(conv\ gpc) = \frac{\sum_{i=RV_{integration\ start}}^{i=RV_{integration\ end}} (M_{PE_i}^2 IR_{measurement\ channel_i})}{\sum_{i=RV_{integration\ start}}^{i=RV_{integration\ end}} (M_{PE_i} IR_{measurement\ channel_i})}.$$ (Eqn. 4)

In Equations 2-4, the RV is column retention volume (linearly-spaced), collected at "1 point per second," the IR is the baseline-subtracted IR detector signal, in Volts, from the IR5 measurement channel of the GPC instrument, and $M_{PE}$ is the polyethylene-equivalent MW determined from Equation 1. Data calculation were performed using "GPC One software (version 2.013H)" from PolymerChAR.

Creep Zero Shear Viscosity Measurement Method

Zero-shear viscosities were obtained via creep tests, which were conducted on an AR-G2 stress controlled rheometer (TA Instruments; New Castle, Del.), using 25-mm-diameter parallel plates, at 190° C. The rheometer oven was set to test temperature for at least 30 minutes, prior to zeroing the fixtures. At the testing temperature, a compression molded sample disk was inserted between the plates, and allowed to come to equilibrium for 5 minutes. The upper plate was then lowered down to 50 μm (instrument setting) above the desired testing gap (1.5 mm). Any superfluous material was trimmed off, and the upper plate was lowered to the desired gap. Measurements were done under nitrogen purging at a flow rate of 5 L/min. The default creep time was set for 2 hours.

Each sample was compression-molded into "2 mm thick ×25 mm diameter" circular plaque, at 177° C., for 5 minutes, under 10 MPa pressure, in air. The sample was then taken out of the press and placed on a counter top to cool.

A constant low shear stress of 20 Pa was applied for all of the samples, to ensure that the steady state shear rate was low enough to be in the Newtonian region. The resulting steady state shear rates were in the range of $10^{-3}$ to $10^{-4}$ s$^{-1}$ for the samples in this study. Steady state was determined by taking a linear regression for all the data, in the last 10% time window of the plot of "log (J(t)) vs. log(t)," where J(t) was creep compliance and t was creep time. If the slope of the linear regression was greater than 0.97, steady state was considered to be reached, then the creep test was stopped. In all cases in this study, the slope meets the criterion within two hours. The steady state shear rate was determined from the slope of the linear regression of all of the data points, in the last 10% time window of the plot of "ε vs. t," where ε was strain. The zero-shear viscosity was determined from the ratio of the applied stress to the steady state shear rate.

In order to determine if the sample was degraded during the creep test, a small amplitude oscillatory shear test was conducted before, and after, the creep test, on the same specimen from 0.1 to 100 rad/s. The complex viscosity values of the two tests were compared. If the difference of the viscosity values, at 0.1 rad/s, was greater than 5%, the sample was considered to have degraded during the creep test, and the result was discarded.

Zero-Shear Viscosity Ratio (ZSVR) is defined as the ratio of the zero-shear viscosity (ZSV) of the branched polyethylene material to the ZSV of a linear polyethylene material (see ANTEC proceeding below) at the equivalent weight average molecular weight (Mw(conv gpc)), according to the following Equation 5:

$$ZSVR = \frac{\eta_{0B}}{\eta_{0L}} = \frac{\eta_{0B}}{2.29^{-15} M_{w(conv\cdot gpc)}^{3.65}}.$$ (Eqn. 5)

The ZSV value was obtained from creep test, at 190° C., via the method described above. The Mw(conv gpc) value was determined by the conventional GPC method (Equation 3), as discussed above. The correlation between ZSV of linear polyethylene and its Mw(conv gpc) was established, based on a series of linear polyethylene reference materials. A description for the ZSV-Mw relationship can be found in the ANTEC proceeding: Karjala et al., *Detection of Low Levels of Long-chain Branching in Polyolefins*, Annual Technical Conference—Society of Plastics Engineers (2008), 66th 887-891.

The present invention may be embodied in other forms, without departing from the spirit and the essential attributes thereof, and, accordingly, reference should be made to the appended claims, rather than to the foregoing specification, as indicating the scope of the invention.

The invention claimed is:

1. A procatalyst selected from the group consisting of:

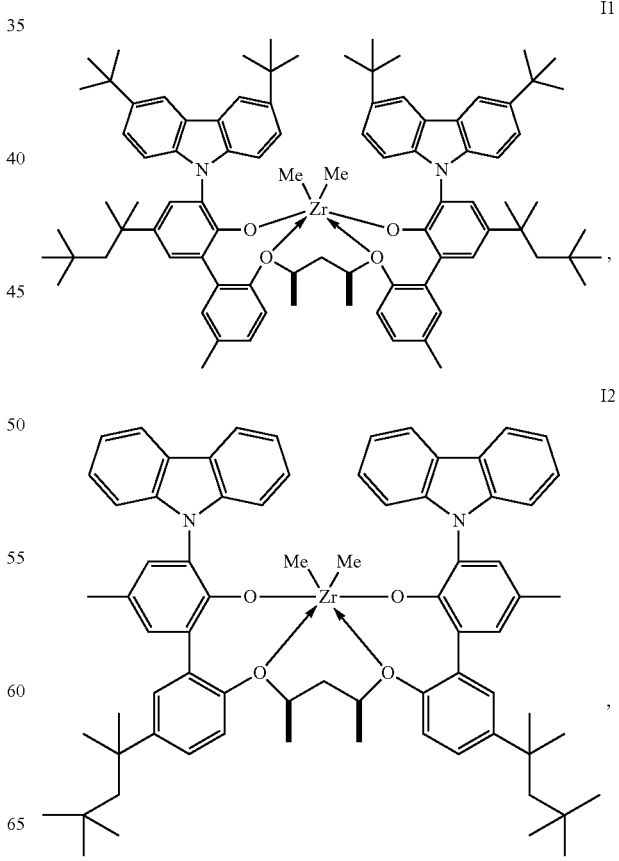

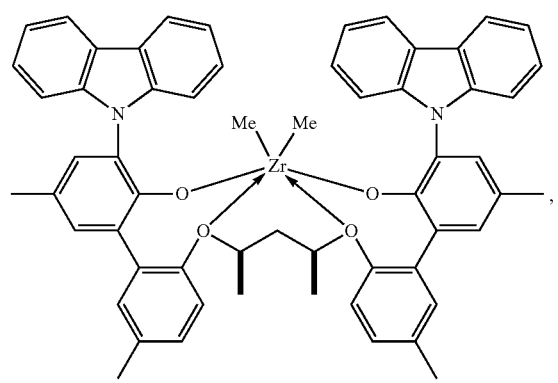
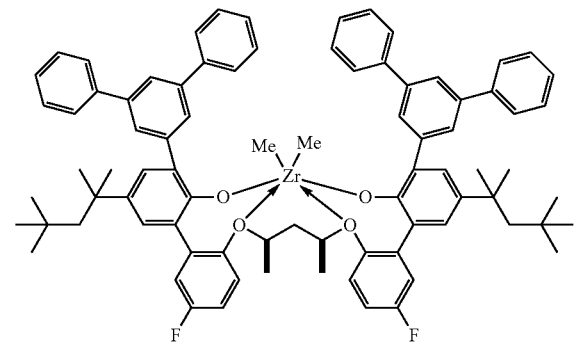
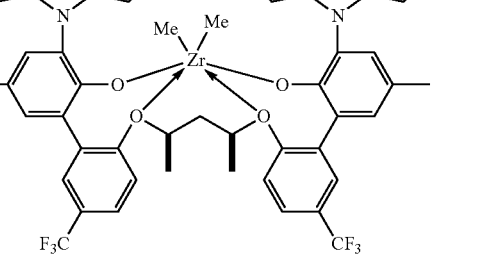

-continued
I12
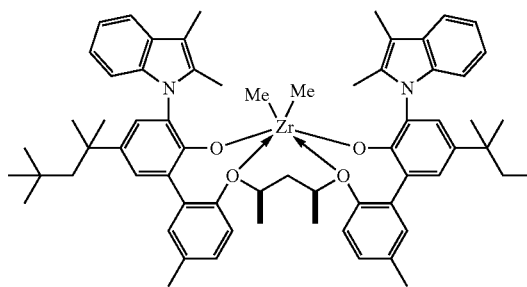
I13
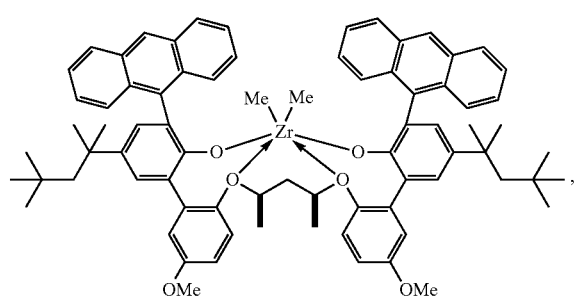
I15
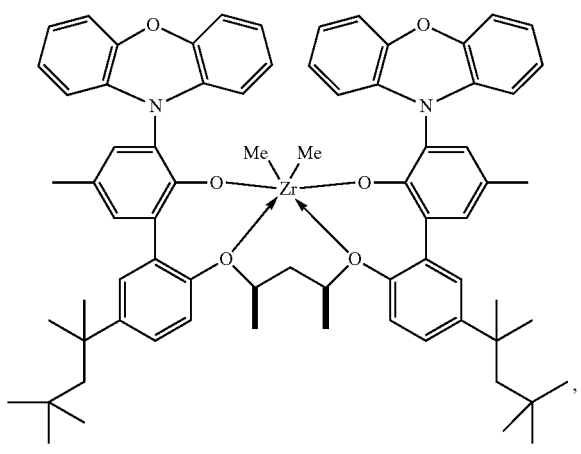
I16
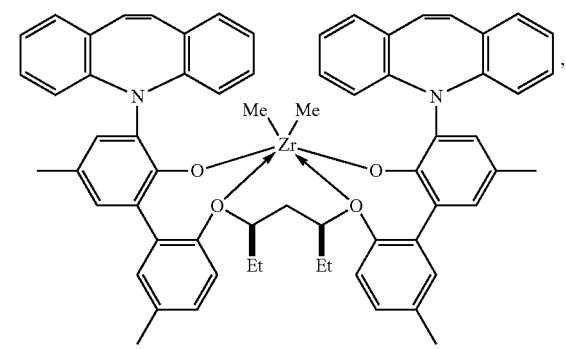
-continued
I20
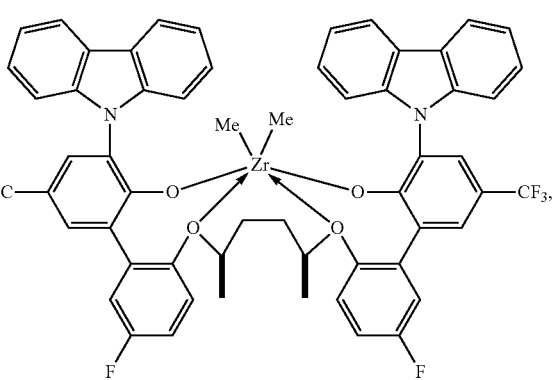
I21
I22
I23
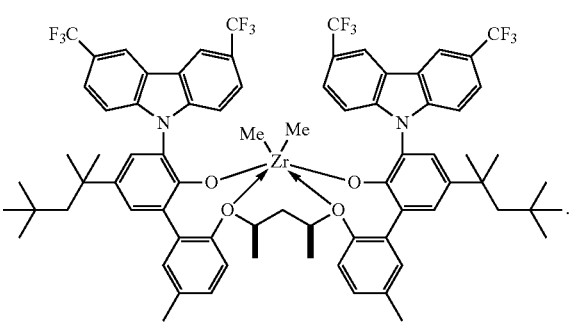

2. A procatalyst having the structure 15:
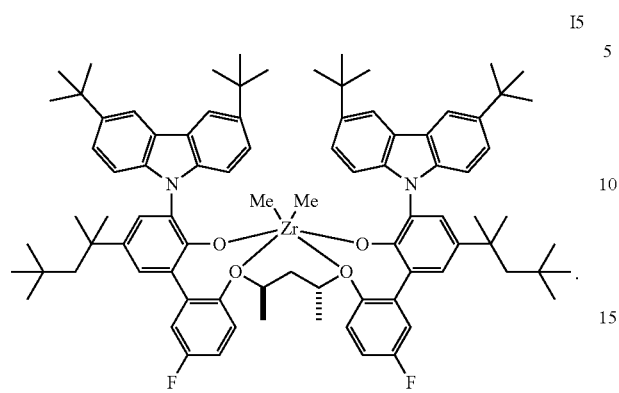
3. A catalyst system comprising the reaction product of the following:
   A) one or two procatalysts of claim 1; and
   B) one or two cocatalysts selected from the group consisting of: polymeric or oligomeric aluminoxanes, or strong Lewis Acid.
* * * * *